(12) United States Patent
Voronina et al.

(10) Patent No.: US 11,326,184 B2
(45) Date of Patent: May 10, 2022

(54) METHODS AND COMPOSITIONS FOR TARGETED GENETIC MODIFICATION THROUGH SINGLE-STEP MULTIPLE TARGETING

(71) Applicant: Regeneron Pharmaceuticals, Inc., Tarrytown, NY (US)

(72) Inventors: Vera Voronina, Sleepy Hollow, NY (US); Lynn Macdonald, Harrison, NY (US); Brian Zambrowicz, Sleepy Hollow, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 63 days.

(21) Appl. No.: 14/974,623

(22) Filed: Dec. 18, 2015

(65) Prior Publication Data

US 2016/0177339 A1    Jun. 23, 2016

Related U.S. Application Data

(60) Provisional application No. 62/094,104, filed on Dec. 19, 2014, provisional application No. 62/167,408, filed on May 28, 2015, provisional application No. 62/205,524, filed on Aug. 14, 2015.

(51) Int. Cl.
*C12N 15/90* (2006.01)
*A01K 67/027* (2006.01)
*C12N 9/22* (2006.01)
*C12N 15/85* (2006.01)

(52) U.S. Cl.
CPC ........ *C12N 15/907* (2013.01); *A01K 67/0276* (2013.01); *A01K 67/0278* (2013.01); *A01K 2217/072* (2013.01); *A01K 2217/075* (2013.01); *A01K 2227/105* (2013.01); *C12N 9/22* (2013.01); *C12N 15/8509* (2013.01)

(58) Field of Classification Search
None
See application file for complete search history.

(56) References Cited

U.S. PATENT DOCUMENTS

| | | | |
|---|---|---|---|
| 5,612,205 A | 3/1997 | Kay et al. | |
| 6,372,956 B1 | 4/2002 | Goldsmith et al. | |
| 6,566,579 B1 | 5/2003 | Jaisser et al. | |
| 6,586,251 B2 | 7/2003 | Economides et al. | |
| 7,105,348 B2 * | 9/2006 | Murphy | A01K 67/0275 435/440 |
| 7,294,754 B2 | 11/2007 | Poueymirou et al. | |
| 7,771,967 B2 | 8/2010 | Huang et al. | |
| 8,502,018 B2 | 8/2013 | Murphy et al. | |
| 8,697,359 B1 | 4/2014 | Zhang | |
| 9,228,208 B2 | 1/2016 | Frendewey et al. | |
| 9,476,065 B2 | 10/2016 | Horwitz et al. | |
| 10,362,771 B2 | 7/2019 | Mashimo et al. | |
| 2003/0134318 A1 | 7/2003 | Case et al. | |
| 2003/0175968 A1 | 9/2003 | Golic et al. | |
| 2004/0018626 A1 | 1/2004 | Murphy et al. | |
| 2004/0197317 A1 | 10/2004 | Rao et al. | |
| 2005/0144655 A1 | 6/2005 | Economides et al. | |
| 2008/0066197 A1 | 3/2008 | Ying et al. | |
| 2008/0113437 A1 | 5/2008 | Joly et al. | |
| 2008/0299580 A1 | 12/2008 | DeKelver et al. | |
| 2009/0055943 A1 | 2/2009 | Economides et al. | |
| 2010/0218264 A1 | 8/2010 | Cui et al. | |
| 2011/0207221 A1 | 8/2011 | Cost et al. | |
| 2011/0307968 A1 | 12/2011 | Auerbach et al. | |
| 2012/0272349 A1 | 10/2012 | Ochiya et al. | |
| 2012/0315670 A1 | 12/2012 | Jacobson et al. | |
| 2013/0210681 A1 * | 8/2013 | Zhang | C12N 9/22 506/26 |
| 2013/0309670 A1 | 11/2013 | Frendewey et al. | |
| 2014/0068797 A1 | 3/2014 | Doudna et al. | |
| 2014/0273226 A1 | 9/2014 | Wu | |

(Continued)

FOREIGN PATENT DOCUMENTS

| | | |
|---|---|---|
| CN | 1484707 A | 3/2004 |
| EP | 1360287 B1 | 9/2012 |

(Continued)

OTHER PUBLICATIONS

Jiang et al. RNA-Guided Editing of Bacterial Genomes Using CRISPR-Cas Systems. Nature Biotechnology, 2013. 31(3): 233-239.*
Rong et al, Homologous Recombination in Human Embryonic Stem Cells Using CRISPR/Cas9 Nickase and a Long DNA Donor Template. Protein Cell, 2014. 5(4):258-260.*
Houdebine, Louis-Marie. Transgenic Animal Models in Biomedical Research. Methods in Molecular Biology, 2007. 360: 163-202.*
"Stem Cells: Scientific Progress and Future Research Directions," National Institute of Health, Department of Health and Human Services, (2001).

(Continued)

*Primary Examiner* — James D Schultz
*Assistant Examiner* — Kimberly A Aron
(74) *Attorney, Agent, or Firm* — Margarita Zippin; Yongjin Choi; Alston & Bird LLP

(57) ABSTRACT

Methods and compositions are provided for making one or more targeted genetic modifications at a target genomic locus within a cell and for producing non-human animals comprising the modified genomic locus. The methods employ two or more large targeting vectors which are capable of recombining with each other and with the target genomic locus in a single genomic targeting step. The methods may also be employed in combination with a nuclease agent. Methods and compositions are also provided for enhancing homologous recombination at a target genomic locus in a cell. The methods employ two or more nucleic acids comprising one or more overlapping sequences. The methods may be employed in combination with a nuclease agent or without a nuclease agent.

32 Claims, 4 Drawing Sheets
Specification includes a Sequence Listing.

(56) References Cited

U.S. PATENT DOCUMENTS

| | | | |
|---|---|---|---|
| 2014/0273234 | A1 | 9/2014 | Zhang et al. |
| 2014/0301990 | A1 | 10/2014 | Gregory et al. |
| 2014/0309487 | A1 | 10/2014 | Lee et al. |
| 2014/0310828 | A1 | 10/2014 | Lee et al. |
| 2014/0342456 | A1 | 11/2014 | Mali et al. |
| 2015/0079680 | A1 | 3/2015 | Bradley et al. |
| 2015/0140664 | A1 | 5/2015 | Byrne et al. |
| 2015/0159174 | A1 | 6/2015 | Frendewey et al. |
| 2015/0159175 | A1 | 6/2015 | Frendewey et al. |
| 2015/0184199 | A1 | 7/2015 | Horwitz et al. |
| 2015/0376650 | A1 | 12/2015 | Auerbach et al. |
| 2015/0376651 | A1 | 12/2015 | Frendewey et al. |
| 2016/0024529 | A1 | 1/2016 | Carstens |
| 2016/0046960 | A1 | 2/2016 | Frendewey et al. |
| 2016/0060657 | A1 | 3/2016 | Frendewey et al. |
| 2016/0081314 | A1* | 3/2016 | Thurston ............ C07K 14/7051 800/6 |
| 2016/0108369 | A1 | 4/2016 | Kuno et al. |
| 2016/0145646 | A1 | 5/2016 | Frendewey et al. |
| 2017/0251647 | A1 | 9/2017 | Mashimo et al. |
| 2019/0338274 | A1 | 11/2019 | Bradley et al. |

FOREIGN PATENT DOCUMENTS

| | | |
|---|---|---|
| EP | 3009511 A2 | 4/2016 |
| EP | 2596101 B1 | 12/2018 |
| WO | WO 2002/066630 A1 | 8/2002 |
| WO | WO 2003/087341 A2 | 10/2003 |
| WO | WO 2006/044962 A1 | 4/2006 |
| WO | WO 2007/117410 A2 | 10/2007 |
| WO | WO 2008/151081 A1 | 12/2008 |
| WO | WO 2009/104094 A2 | 8/2009 |
| WO | WO 2011/051390 A1 | 5/2011 |
| WO | WO 2011/078665 A1 | 6/2011 |
| WO | WO 2011/154927 A2 | 12/2011 |
| WO | WO 2012/012667 A2 | 1/2012 |
| WO | WO 2012/018726 A1 | 9/2012 |
| WO | WO 2012/129198 A1 | 9/2012 |
| WO | WO 2013/063361 A1 | 5/2013 |
| WO | WO 2013/163394 A1 | 10/2013 |
| WO | WO 2013/169802 A1 | 11/2013 |
| WO | WO 2013/176772 A1 | 11/2013 |
| WO | WO-2014093908 A2 * 6/2014 ......... A01K 67/0275 |
| WO | WO 2014/104878 A1 | 7/2014 |
| WO | WO 2014/143381 A1 | 9/2014 |
| WO | WO 2014/172489 A2 | 10/2014 |
| WO | WO 2015/040402 A1 | 3/2015 |
| WO | WO 2015/077290 A2 | 5/2015 |
| WO | WO 2015/088643 A1 | 6/2015 |
| WO | WO 2015/095804 A1 | 6/2015 |
| WO | WO 2015/163733 A1 | 10/2015 |
| WO | WO 2015/166272 A2 | 11/2015 |
| WO | WO 2015/188109 A1 | 12/2015 |
| WO | WO 2015/200805 A2 | 12/2015 |
| WO | WO 2016/061073 A1 | 4/2016 |
| WO | WO 2016/061374 A1 | 4/2016 |
| WO | WO 2016/081923 A2 | 5/2016 |
| WO | WO 2016/089866 A1 | 6/2016 |
| WO | WO 2016/100819 A1 | 6/2016 |

OTHER PUBLICATIONS

Berdien, et al., "TALEN-mediated editing of endogenous T-cell receptors facilitates efficient reprogramming of T lymphocytes by lentiviral gene transfer," Gene Therapy, 21, 539-548 (2014).
Byrne et al., "Multi-kilobase homozygous targeted gene replacement in human induced pluripotent stem cells," Nucleic Acids Research, Vo. 43(3), p. e21, 2014 (epub Nov. 20, 2014).
Chen et al., "High-frequency genome editing using ssDNA oligonucleotides with zinc-finger nucleases," Nature Methods, vol. 8(9), pp. 753-755, 2011. (Jul. 17, 2011).
Choulika et al., "Induction of Homologous Recombination in Mammalian Chromosomes by Using the I-Scel System of *Saccharomyces cerevisiae*," Mol. Cell. Biol., vol. 15(4), pp. 1968-1973, 1995.
Cobb and Zhao, "Direct cloning of large genomic sequences," Nature Biotechnology, 2012, vol. 30(5), pp. 405-406.
Cong et al., "Multiplex Genome Engineering Using CRISPR/Cas Systems," Science, vol. 339(6121), pp. 819-823 plus Supplemental Materials, Jan. 3, 2013.
Cong, et al., "Multiplex genome engineering using CRISPR/Cas systems," Science, 2013, vol. 339(6121), pp. 819-823.
Cui, et al., "Targeted integration in rat and mouse embryos with zinc-fnger nucleases," Nature Biotechnology, vol. 29, No. 1, 64-68 (Jan. 2011).
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.
Doudna et al., "The new frontier of genome engineering with CRISPR-Cas9," Science, vol. 346(6213), pp. 1258096-1-1258096-9, Nov. 28, 2014.
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Flisikowska, et al., "Efficient Immunoglobulin Gene Disruption and Targeted Replacement in Rabbit Using Zinc Finger Nucleases," Plos one, vol. 6 Issue 6 (Jun. 2011).
Frendewey ,"VelociGene: Large-scale Modification of Rodent Genomes," Wellcome Trust Advanced Course: Genetic Engineering of Mammalian Stem Cells, Mar. 13, 2014.
Frendewey, "VelociGene: Large-scale Modification of Rodent Genomes," Wellcome Trust Advanced Course: Genetic Engineering of Mammalian Stem Cells, Feb. 20, 2015.
Gennequin, et al., "CRISPR/Cas-induced double-strand breaks boost the frequency of gene replacements for humanizing the mouse Cnr2 gene," Biochem. Biophys. Res. Commun., (2013), http://dx.doi.org/10.1016/j.bbrc.2013.10.138.
Gibson, D., et al., "Enzymatic assembly of DNA molecules up to several hundred kilobases," Nature Methods, 2009, vol. 6(5), pp. 343-345.
Gibson, Daniel G., "Enzymatic Assembly of Overlapping DNA Fragments," Methods in Enzymology, 2011, vol. 498, pp. 349-361.
Johnson, et al., "A rapid assay to quantify the cleavage efficiency of custom-designed nucleases in planta," Plant Mol Biol, 82:207-221 (2013).
Kashimada et al., "Sry: the master switch in mammalian sex determination," Development, vol. 137(23), pp. 3921-3930, Dec. 2, 2010.
Kato et al., "Production of Sry knockout mouse using TALEN via oocyte injection," Scientific Reports, vol. 3, p. 3136, 2013 (published Nov. 5, 2013).
Kuno et al., "Generation of fertile and fecund F0 XY female mice from XY ES cells," Transgenic Research, vol. 24(1), pp. 19-29, 2014 (epub Aug. 3, 2014).
Kuroiwa, et al., "Sequential targeting of the genes encloding immunoglobulin-μ and prion protein in cattle," Nature Genetics, vol. 36, No. 7, (Jul. 2004).
Li et al., "Germline Competent Embryonic Stem Cells Derived from Rat Blastocysts," Cell, vol. 135, pp. 1299-1310, 2008.
Lin, S.-C., et al., "Strategies for gene disruption in *Drosophila*," Cell & Bioscience (2014), vol. 4(1), p. 63.
Lombardo, et al., "Gene editing in human stem cells using zinc finger nucleases and integrase-defective lentiviral vector delivery," Nature Biotechnology, 2007, vol. 25(11), pp. 1298-1306.
MacDonald, et al., "Precise and in situ genetic humanization of 6 Mb of mouse immunoglobulin genes," PNAS, vol. 111, No. 14: 5147-5152, (Apr. 8, 2014).
Mali et al., "RNA-Guided Human Genome Engineering via Cas9," Science, vol. 339(6121), pp. 823-826 plus Supplemental Materials, Jan. 3, 2013.

(56) References Cited

OTHER PUBLICATIONS

Mali, et al., "RNA-guided human genome engineering via Cas9," Science, 2013, vol. 339(6121), pp. 823-826.
Mashimo et al., "Generation of knockout rats with X-linked severe combined immunodeficiency (X-SCID) using zinc finger nucleases," PLoS One, vol. 5(1), p. e8870, 2010.
Narsinh et al., "Gene Correction in Human Embryonic and Induced Pluripotent Stem Cells: Promise and Challenges Ahead", Molecular Therapy, vol. 18, No. 6, pp. 1061-1063, (Jun. 2010).
PCT International Preliminary Report on Patentability for application PCT/US2013/038165 dated Oct. 28, 2014.
PCT International Preliminary Report on Patentability for application PCT/US2014/034412 dated Oct. 30, 2015.
PCT International Search Report and Written Opinion of the International Searching Authority for application PCT/US2014/060788 dated Jan. 26, 2015.
PCT International Search Report for application PCT/US2015/034503 dated Sep. 8, 2015.
PCT Written Opinion of the International Searching Authority for application PCT/US2015/034503 dated Sep. 8, 2015.
PCT/US2013/038165 International Search Report and Written Opinion dated Jul. 12, 2013.
PCT/US2014/034412 International Search Report and Written Opinion of the Searching Authority dated Oct. 9, 2014.
PCT US2015/038001 Invitation of Pay Additional Fees dated Nov. 13, 2015.
Peng, Y., et al., "Making designer mutants in model organisms," Development (2014), vol. 141, pp. 4042-4054.
Porteus, et al,, "Gene targeting using zinc finger nucleases," Nature Biotechnology, vol. 23(8), pp. 967-973, 2005.
Poueymirou et al., "F0 generation mice fully derived from gene-targeted embryonic stem cells allowing immediate analysis," Nature Biotechnology, Epub Dec. 24, 2006, vol. 25(1):91-99.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Stemgent Product Specification Sheet, PD0325901, pp. 1-2 (2012).
Tong et al., "Generating gene knockout rats by homologous recombination in embryonic stem cells," Nature Protocols, vol. 6(6), pp. 827-844, 2011 (epub May 26, 2011).
U.S. Appl. No. 13/870,280 Final Rejection dated Oct. 15, 2015.
U.S. Appl. No. 13/870,280, Requirement for Restriction/Election dated Jul. 22, 2014.00000000.
U.S. Appl. No. 14/254,715 Final Office Action dated Nov. 30, 2015.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/314,866, Final Office Action dated Jun. 4, 2015.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 14/731,914 , Requirement for Restriction/Election dated Dec. 31, 2015.
U.S. Appl. No. 14/926,773, Requirement for Restriction/Election dated Feb. 16, 2016.
U.S. Appl. No. 13/870,280 , Advisory Action dated Jan. 5, 2016.
U.S. Appl. No. 13/870,280, Non-Final Office Action dated Mar. 13, 2015.
U.S. Appl. No. 14/254,715, Requirement for Restriction/Election dated Jun. 4, 2015.
U.S. Appl. No. 14/928,180, Non-Final Office Action dated Jan. 5, 2016.

Wang et al., "TALEN-mediated editing of the mouse Y chromosome," Nature Biotechnology, vol. 31(6), p. 530-532, 2013 (epub May 12, 2013).
Wen et al., "Completely ES Cell-Derived Mice Produced by Tetraploid Complementation Using Inner Cell Mass (ICM) Deficient Blastocysts," PLoS One, vol. 9(4), e94730, Apr. 14, 2014.
Zhou, H., et al., "Large chromosomal deletions and heritable small genetic changes induced by CRISPR/Cas9 in rice," Nucleic Acids Research (2014), vol. 42(17), pp. 10903-10914.
Zhang et al., "The CRISPR/Cas9 system produces specific and homozygous targeted gene editing in rice in one generation," Plant Biotechnol. J., vol. 12(6), pp. 797-807, May 23, 2014.
Abudayyeh et al., "C2c2 is a single-component programmable RNA-guided RNA-targeting CRISPR effector," Science, vol. 353(6299), Jun. 2, 2016.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Benders et al., "Cloning whole bacterial genomes in yeast," Nucleic Acids Res., vol. 38(8), pp. 2558-2569, Mar. 7, 2010.
Bernardini et al., "Site-specific genetic engineering of the Anopheles gambiae Y chromosome," Proc. Natl. Acad. Sci. USA, vol. 111(21), pp. 7600-7605, May 12, 2014.
EP Application No. 14784879.0, Extended European Search Report dated Sep. 19, 2016.
Evers et al., "CRISPR knockout screening outperforms shRNA and CRISPRi in identifying essential genes," Nature Biotechnology, vol. 24(6), pp. 631-633, Apr. 25, 2016.
Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.
Gao et al., "DNA-guided genome editing using the Natronobacterium gregoryi Argonuate," Nature Biotechnology, vol. 34(7), pp. 768-773, May 2, 2016.
Gratz et al., "Genome Engineering of *Drosophila* with the CRISPR RNA-Guided Cas9 Nuclease," Genetics, vol. 194, pp. 1029-1035, 2013. (published May 2013).
Gratz et al., "Highly Specific and Efficient CRISPR/Cas9-Catalyzed Homology-Directed Repair in *Drosophila*," Genetics, vol. 196(4), pp. 961-971 plus Supporting Information, Jan. 29, 2014.
Jallepalli et al., "Securin is required for chromosomal stability in human cells," Cell, vol. 105(4), pp. 445-457, May 18, 2001.
Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.
Jasin, et al., "Repair of Strand Breaks by Homologous Recombination," Cold Spring Harb. Perspect. Biol., vol. 5(11), p. a012740, Nov. 1, 2013.
Komor et al, "Programmable editing of a target base in genomic DNA without double-stranded cleavage," Nature, vol. 533(7603), pp. 420-424, Apr. 20, 2016.
Konermann et al., "Genome-scale transcriptional activation by an engineered CRISPR-Cas9 complex," Nature, vol. 517(7536), pp. 583-588, published online Dec. 10, 2014.
Kuijpers et al., "One-step assembly and targeted integration of multigene constructs assisted by the I-SceI meganuclease in *Saccharomyces cerevisiae*," FEMS Yeast Res., vol. 13(8), pp. 769-781, Oct. 7, 2013.
Li et al., "Optimization of Genome Engineering Approaches with the CRISPR/Cas9 System," PLoS One, vol. 9(8), p. e105779, Aug. 28, 2014.
Liu et al., "A one-step cloning method for the construction of somatic cell gene targeting vectors: application to production of human knockout cell lines," BMC Biotechnol., vol. 12, p. 71, Oct. 9, 2012.
Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.
Mali, et al., "Cas9 as a versatile tool for engineering biology," Nature Methods, vol. 10(10), pp. 957-963, 2013.

(56) References Cited

OTHER PUBLICATIONS

Mashiko et al., "Generation of mutant mice by pronuclear injection of circular plasmid expressing Cas9 and single guided RNA," Sci. Rep., vol. 3, p. 3355, Nov. 27, 2013.
Morgens et al., "Systematic comparison of CRISPR/Cas9 and RNAi screens for essential genes," Nature Biotechnology, vol. 34(6), pp. 634-636, May 9, 2016.
Musser, "Rodent," Brittanica. Retrieved from the Internet May 31, 2016: http://www.brittanica.com/animal/rodent.
Parikh et al., "Detailed Phenotypic and Molecular Analyses of Genetically Modified Mice Generated by CRISPR-Cas9-Mediated Editing," PLoS One, vol. 10(1), p. e0116484, Jan. 14, 2015.
PCT International Preliminary Report on Patentability for application PCT/US2014/060788 dated Jun. 23, 2016.
PCT International Search Report and Written Opinion of the International Searching Authority for application PCT/US2015/038001 dated Feb. 25, 2016.
PCT International Search Report and Written Opinion of the International Searching Authority for application PCT/US2015/062023 dated May 13, 2016.
PCT International Search Report and Written Opinion of the International Searching Authority for application PCT/US2015/066681 dated Mar. 29, 2016.
PCT/US2015/062023 Invitation of Pay Additional Fees dated Feb. 8, 2016.
Port et al., "Optimized CRISPR/Cas tools for efficient germline and somatic genome engineering in *Drosophila*," Proc. Natl. Acad. Sci. U.S.A., vol. 111(29), pp. E2967-E2976 plus Supporting Information, Jul. 7, 2014.
Quinn et al., "A Site-Specific, Single-Copy Transgenesis Strategy to Identify 5' Regulatory Sequences of the Mouse Testis-Determining Gene Sry," PLoS One, vol. 9(4), p. e94813, Apr. 2014.
Ran et al., "Double nicking by RNA-guided CRISPR Cas9 for enhanced genome editing specificity," Cell, vol. 154, pp. 1380-1389, 2013.
Ran et al., "Genome engineering using the CRISPR-Cas9 system," Nature Protocols, vol. 8(11), pp. 2281-2308, Oct. 24, 2013.
Ran et al., "In vivo genome editing using *Staphylococcus aureus* Cas9," Nature, vol. 520(7546), pp. 186-191, Apr. 1, 2015.
Shan et al., "Targeted genome modification of crop plants using a CRISPR-Cas system," Nature Biotechnology, vol. 31(8), pp. 686-688, Aug. 1, 2013.
Siao et al., "Single-step homozygous humanization induced by dual CRISPR/Cas9 cleavage," Oct. 28, 2015.
U.S. Appl. No. 14/254,715, Final Office Action dated Sep. 19, 2016.
U.S. Appl. No. 14/254,715, Non-Final Office Action dated Apr. 21, 2016.
U.S. Appl. No. 14/314,866, Advisory Action dated Aug. 15, 2016.
U.S. Appl. No. 14/314,866, Final Office Action dated Apr. 26, 2016.
U.S. Appl. No. 14/314,866, Non-Final Office Action dated Sep. 19, 2016.
U.S. Appl. No. 14/515,503, Non-Final Office Action dated May 20, 2016.
U.S. Appl. No. 14/515,503, Notice of Allowance dated Sep. 23, 2016.
U.S. Appl. No. 14/515,503, Requirement for Restriction/Election dated Mar. 4, 2016.
U.S. Appl. No. 14/731,914, Non-Final Office Action dated Jun. 17, 2016.
U.S. Appl. No. 14/751,807, Requirement for Restriction/Election dated Aug. 26, 2016.
U.S. Appl. No. 14/926,773, Non-Final Office Action dated May 6, 2016.
U.S. Appl. No. 14/928,180, Advisory Action dated Aug. 22, 2016.
U.S. Appl. No. 14/928,180, Final Office Action dated Jun. 6, 2016.
U.S. Appl. No. 14/974,623, Non-Final Office Action dated Dec. 16, 2016.
Wang et al., "One-Step Generation of Mice Carrying Mutations in Multiple Genes by CRISPR/Cas-Mediated Genome Engineering," Cell, vol. 153, pp. 910-918 plus supplemental materials, 2013. (published May 2013).
Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.
Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.
Yoshimi et al., "ssODN-mediated knock-in with CRISPR-Cas for large genomic regions in zygotes," Nat. Commun., vol. 7, p. 10431, Jan. 20, 2016.
Yu et al., "Highly Efficient Genome Modifications Mediated by CRISPR/Cas9 in *Drosophila*," Genetics, vol. 195, pp. 289-291 plus supporting information, Sep. 2013.
Zhang et al., "Biallelic targeting of expressed genes in mouse embryonic stem cells using the Cas9 system," Methods, vol. 69(2), pp. 171-178, Jun. 12, 2014.
Kosicki et al., "Repair of double-strand breaks induced by CRISPR-Cas9 leads to large deletions and complex rearrangements," Nat. Biotechnol., 36(8): 765-771, (Jul. 16, 2018).
EP Application No. 19201384.5 Extended European Search Report dated Feb. 19, 2020.
Guo, et al., "Asymmetric DNA bending in the Cre-loxP site-specific recombination synapse," Proc. Natl. Acad. Sci. U.S.A., 96(13):7143-7148, (Jun. 1999).

\* cited by examiner

SEQUENCE LISTING

<160> NUMBER OF SEQ ID NOS: 86

<210> SEQ ID NO 1
<211> LENGTH: 23
<212> TYPE: DNA
<213> ORGANISM: Artificial Sequence
<220> FEATURE:
<223> OTHER INFORMATION: a genomic target sequence that is linked to a
      guide RNA (gRNA)
<220> FEATURE:
<221> NAME/KEY: misc_feature
<222> LOCATION: (2)...(21)
<223> OTHER INFORMATION: n = A,T,C or G

<400> SEQUENCE: 1
gnnnnnnnnn nnnnnnnnnn ngg                                            23

<210> SEQ ID NO 2
<211> LENGTH: 42
<212> TYPE: DNA
<213> ORGANISM: Artificial Sequence
<220> FEATURE:
<223> OTHER INFORMATION: ZFN1/2 recognition site

<400> SEQUENCE: 2
tgcgatcgct gcggccgatc ttagccagac gagcgggttc gg                       42

<210> SEQ ID NO 3
<211> LENGTH: 36
<212> TYPE: DNA
<213> ORGANISM: Artificial Sequence
<220> FEATURE:
<223> OTHER INFORMATION: ZFN3/4 recognition site

<400> SEQUENCE: 3
cgctgcggcc gatcttagcc agacgagcgg gttcgg                              36

<210> SEQ ID NO 4
<211> LENGTH: 39
<212> TYPE: DNA
<213> ORGANISM: Artificial Sequence
<220> FEATURE:
<223> OTHER INFORMATION: ZFN5/6 recognition site

<400> SEQUENCE: 4
agcgtgtccg acctgatgca gctctcggag ggcgaagaa                           39

<210> SEQ ID NO 5
<211> LENGTH: 18
<212> TYPE: DNA
<213> ORGANISM: Artificial Sequence
<220> FEATURE:

```
<223> OTHER INFORMATION: ZFN1 Binding sequence

<400> SEQUENCE: 5
tgcgatcgct gcggccga                                                 18

<210> SEQ ID NO 6
<211> LENGTH: 18
<212> TYPE: DNA
<213> ORGANISM: Artificial Sequence
<220> FEATURE:
<223> OTHER INFORMATION: ZFN2 Binding sequence

<400> SEQUENCE: 6
ccgaacccgc tcgtctgg                                                 18

<210> SEQ ID NO 7
<211> LENGTH: 15
<212> TYPE: DNA
<213> ORGANISM: Artificial Sequence
<220> FEATURE:
<223> OTHER INFORMATION: ZFN3 Binding sequence

<400> SEQUENCE: 7
cgctgcggcc gatct                                                    15

<210> SEQ ID NO 8
<211> LENGTH: 15
<212> TYPE: DNA
<213> ORGANISM: Artificial Sequence
<220> FEATURE:
<223> OTHER INFORMATION: ZFN4 Binding sequence

<400> SEQUENCE: 8
ccgaacccgc tcgtc                                                    15

<210> SEQ ID NO 9
<211> LENGTH: 18
<212> TYPE: DNA
<213> ORGANISM: Artificial Sequence
<220> FEATURE:
<223> OTHER INFORMATION: ZFN5 Binding sequence

<400> SEQUENCE: 9
agcgtgtccg acctgatg                                                 18

<210> SEQ ID NO 10
<211> LENGTH: 15
<212> TYPE: DNA
<213> ORGANISM: Artificial Sequence
<220> FEATURE:
<223> OTHER INFORMATION: ZFN6 Binding sequence

<400> SEQUENCE: 10
ttcttcgccc tccga                                                    15

<210> SEQ ID NO 11
<211> LENGTH: 6
<212> TYPE: DNA
<213> ORGANISM: Artificial Sequence
<220> FEATURE:
<223> OTHER INFORMATION: ZFN1/2 cleavage site

<400> SEQUENCE: 11 tcttag                                                              6
```

```
<210> SEQ ID NO 12
<211> LENGTH: 6
<212> TYPE: DNA
<213> ORGANISM: Artificial Sequence
<220> FEATURE:
<223> OTHER INFORMATION: ZFN3/4cleavage site

<400> SEQUENCE: 12 tagcca                                                                     6

<210> SEQ ID NO 13
<211> LENGTH: 6
<212> TYPE: DNA
<213> ORGANISM: Artificial Sequence
<220> FEATURE:
<223> OTHER INFORMATION: ZFN5/6 cleavage site

<400> SEQUENCE: 13 cagctc                                                                     6

<210> SEQ ID NO 14
<211> LENGTH: 17
<212> TYPE: DNA
<213> ORGANISM: Artificial Sequence
<220> FEATURE:
<223> OTHER INFORMATION: HYG forward primer

<400> SEQUENCE: 14
tgcggccgat cttagcc                                                        17

<210> SEQ ID NO 15
<211> LENGTH: 21
<212> TYPE: DNA
<213> ORGANISM: Artificial Sequence
<220> FEATURE:
<223> OTHER INFORMATION: HYG probe

<400> SEQUENCE: 15
acgagcgggt tcggcccatt c                                                   21

<210> SEQ ID NO 16
<211> LENGTH: 18
<212> TYPE: DNA
<213> ORGANISM: Artificial Sequence
<220> FEATURE:
<223> OTHER INFORMATION: HYG reverse primer

<400> SEQUENCE: 16
ttgaccgatt ccttgcgg                                                       18

<210> SEQ ID NO 17
<211> LENGTH: 23
<212> TYPE: DNA
<213> ORGANISM: Artificial Sequence
<220> FEATURE:
<223> OTHER INFORMATION: HYG-U forward primer

<400> SEQUENCE: 17
cgacgtctgt cgagaagttt ctg                                                 23

<210> SEQ ID NO 18
<211> LENGTH: 24
<212> TYPE: DNA
<213> ORGANISM: Artificial Sequence
<220> FEATURE:
<223> OTHER INFORMATION: HYG-U probe
```

```
<400> SEQUENCE: 18
agttcgacag cgtgtccgac ctga                                            24

<210> SEQ ID NO 19
<211> LENGTH: 19
<212> TYPE: DNA
<213> ORGANISM: Artificial Sequence
<220> FEATURE:
<223> OTHER INFORMATION: HYG-U reverse primer

<400> SEQUENCE: 19
cacgccctcc tacatcgaa                                                  19

<210> SEQ ID NO 20
<211> LENGTH: 20
<212> TYPE: DNA
<213> ORGANISM: Artificial Sequence
<220> FEATURE:
<223> OTHER INFORMATION: HYG-D forward primer

<400> SEQUENCE: 20
tgtcgggcgt acacaaatcg                                                 20

<210> SEQ ID NO 21
<211> LENGTH: 22
<212> TYPE: DNA
<213> ORGANISM: Artificial Sequence
<220> FEATURE:
<223> OTHER INFORMATION: HYG-D probe

<400> SEQUENCE: 21
ccgtctggac cgatggctgt gt                                              22

<210> SEQ ID NO 22
<211> LENGTH: 20
<212> TYPE: DNA
<213> ORGANISM: Artificial Sequence
<220> FEATURE:
<223> OTHER INFORMATION: HYG-D reverse primer

<400> SEQUENCE: 22
gggcgtcggt ttccactatc                                                 20

<210> SEQ ID NO 23
<211> LENGTH: 24
<212> TYPE: DNA
<213> ORGANISM: Artificial Sequence
<220> FEATURE:
<223> OTHER INFORMATION: PGKp1 (Hyg Promoter) forward primer

<400> SEQUENCE: 23
caaatggaag tagcacgtct cact                                            24

<210> SEQ ID NO 24
<211> LENGTH: 23
<212> TYPE: DNA
<213> ORGANISM: Artificial Sequence
<220> FEATURE:
<223> OTHER INFORMATION: PGKp1 (Hyg Promoter) probe

<400> SEQUENCE: 24
ctcgtgcaga tggacagcac cgc                                             23

<210> SEQ ID NO 25
<211> LENGTH: 15
```

```
<212> TYPE: DNA
<213> ORGANISM: Artificial Sequence
<220> FEATURE:
<223> OTHER INFORMATION: PGKp1 (Hyg Promoter) reverse primer

<400> SEQUENCE: 25
ccgctgcccc aaagg                                                      15

<210> SEQ ID NO 26
<211> LENGTH: 20
<212> TYPE: DNA
<213> ORGANISM: Artificial Sequence
<220> FEATURE:
<223> OTHER INFORMATION: hIgK6 forward primer

<400> SEQUENCE: 26
gtcaagcact gctggcacac                                                 20

<210> SEQ ID NO 27
<211> LENGTH: 33
<212> TYPE: DNA
<213> ORGANISM: Artificial Sequence
<220> FEATURE:
<223> OTHER INFORMATION: hIgK6 probe

<400> SEQUENCE: 27
aacccttgtg ctattgaatt gctatgctgt cag                                  33

<210> SEQ ID NO 28
<211> LENGTH: 20
<212> TYPE: DNA
<213> ORGANISM: Artificial Sequence
<220> FEATURE:
<223> OTHER INFORMATION: hIgK6 reverse primer

<400> SEQUENCE: 28
tgttgtagac cctccgccac                                                 20

<210> SEQ ID NO 29
<211> LENGTH: 21
<212> TYPE: DNA
<213> ORGANISM: Artificial Sequence
<220> FEATURE:
<223> OTHER INFORMATION: hIgK12 (MAID 1710 insert) forward primer

<400> SEQUENCE: 29
ttgcctttct cacacctgca g                                               21

<210> SEQ ID NO 30
<211> LENGTH: 25
<212> TYPE: DNA
<213> ORGANISM: Artificial Sequence
<220> FEATURE:
<223> OTHER INFORMATION: hIgK12 (MAID 1710 insert) probe

<400> SEQUENCE: 30
cagcccatcc tgtcacttcg ctgga                                           25

<210> SEQ ID NO 31
<211> LENGTH: 21
<212> TYPE: DNA
<213> ORGANISM: Artificial Sequence
<220> FEATURE:
<223> OTHER INFORMATION: hIgK12 (MAID 1710 insert) reverse primer

<400> SEQUENCE: 31
```
tggcccaaca gtacagctca g                                         21

<210> SEQ ID NO 32
<211> LENGTH: 22
<212> TYPE: DNA
<213> ORGANISM: Artificial Sequence
<220> FEATURE:
<223> OTHER INFORMATION: hIgK13 forward primer

<400> SEQUENCE: 32
tcagtcaatc acctttccca gc                                        22

<210> SEQ ID NO 33
<211> LENGTH: 28
<212> TYPE: DNA
<213> ORGANISM: Artificial Sequence
<220> FEATURE:
<223> OTHER INFORMATION: hIgK13 probe

<400> SEQUENCE: 33
tccccaggta gcctcatgaa ccaatgtt                                  28

<210> SEQ ID NO 34
<211> LENGTH: 23
<212> TYPE: DNA
<213> ORGANISM: Artificial Sequence
<220> FEATURE:
<223> OTHER INFORMATION: hIgK13 reverse primer

<400> SEQUENCE: 34
cacattactg agtccccaca ggg                                       23

<210> SEQ ID NO 35
<211> LENGTH: 25
<212> TYPE: DNA
<213> ORGANISM: Artificial Sequence
<220> FEATURE:
<223> OTHER INFORMATION: hIgK14 forward primer

<400> SEQUENCE: 35
cattgtcaaa gaagcactgg aaatg                                     25

<210> SEQ ID NO 36
<211> LENGTH: 32
<212> TYPE: DNA
<213> ORGANISM: Artificial Sequence
<220> FEATURE:
<223> OTHER INFORMATION: hIgK14 probe

<400> SEQUENCE: 36
accattgcag tttacccacg gttaggattt tt                             32

<210> SEQ ID NO 37
<211> LENGTH: 23
<212> TYPE: DNA
<213> ORGANISM: Artificial Sequence
<220> FEATURE:
<223> OTHER INFORMATION: hIgK14 reverse primer

<400> SEQUENCE: 37
tcttgcaatg ggatcatcag atg                                       23

<210> SEQ ID NO 38
<211> LENGTH: 19
<212> TYPE: DNA
<213> ORGANISM: Artificial Sequence

```
<220> FEATURE:
<223> OTHER INFORMATION: Neo forward primer

<400> SEQUENCE: 38
ggtggagagg ctattcggc                                                 19

<210> SEQ ID NO 39
<211> LENGTH: 23
<212> TYPE: DNA
<213> ORGANISM: Artificial Sequence
<220> FEATURE:
<223> OTHER INFORMATION: Neo probe

<400> SEQUENCE: 39
tgggcacaac agacaatcgg ctg                                            23

<210> SEQ ID NO 40
<211> LENGTH: 17
<212> TYPE: DNA
<213> ORGANISM: Artificial Sequence
<220> FEATURE:
<223> OTHER INFORMATION: Neo reverse primer

<400> SEQUENCE: 40
gaacacggcg gcatcag                                                   17

<210> SEQ ID NO 41
<211> LENGTH: 21
<212> TYPE: DNA
<213> ORGANISM: Artificial Sequence
<220> FEATURE:
<223> OTHER INFORMATION: hIgK15 forward primer

<400> SEQUENCE: 41
caggtgcaaa ggtgaccaca g                                              21

<210> SEQ ID NO 42
<211> LENGTH: 21
<212> TYPE: DNA
<213> ORGANISM: Artificial Sequence
<220> FEATURE:
<223> OTHER INFORMATION: hIgK15 probe

<400> SEQUENCE: 42
tgggtcctgc ccatccatgc a                                              21

<210> SEQ ID NO 43
<211> LENGTH: 20
<212> TYPE: DNA
<213> ORGANISM: Artificial Sequence
<220> FEATURE:
<223> OTHER INFORMATION: hIgK15 reverse primer

<400> SEQUENCE: 43
ggcagcctga gtgtcagagc                                                20

<210> SEQ ID NO 44
<211> LENGTH: 21
<212> TYPE: DNA
<213> ORGANISM: Artificial Sequence
<220> FEATURE:
<223> OTHER INFORMATION: hIgK25 forward primer

<400> SEQUENCE: 44
gttcaggccc cacagactct c                                              21
```

<210> SEQ ID NO 45
<211> LENGTH: 29
<212> TYPE: DNA
<213> ORGANISM: Artificial Sequence
<220> FEATURE:
<223> OTHER INFORMATION: hIgK25 probe

<400> SEQUENCE: 45
tcctctctgg agcaaccatg aagttccct                              29

<210> SEQ ID NO 46
<211> LENGTH: 19
<212> TYPE: DNA
<213> ORGANISM: Artificial Sequence
<220> FEATURE:
<223> OTHER INFORMATION: hIgK25 reverse primer

<400> SEQUENCE: 46
cctgaagcca tgagggcag                                         19

<210> SEQ ID NO 47
<211> LENGTH: 21
<212> TYPE: DNA
<213> ORGANISM: Artificial Sequence
<220> FEATURE:
<223> OTHER INFORMATION: hUbC-D (Neo Promoter) forward primer

<400> SEQUENCE: 47
agggtaggct ctcctgaatc g                                      21

<210> SEQ ID NO 48
<211> LENGTH: 20
<212> TYPE: DNA
<213> ORGANISM: Artificial Sequence
<220> FEATURE:
<223> OTHER INFORMATION: hUbC-D (Neo Promoter) probe

<400> SEQUENCE: 48
acaggcgccg gacctctggt                                        20

<210> SEQ ID NO 49
<211> LENGTH: 21
<212> TYPE: DNA
<213> ORGANISM: Artificial Sequence
<220> FEATURE:
<223> OTHER INFORMATION: hUbC-D (Neo Promoter) reverse primer

<400> SEQUENCE: 49
ccaaagaaac tgacgcctca c                                      21

<210> SEQ ID NO 50
<211> LENGTH: 21
<212> TYPE: DNA
<213> ORGANISM: Artificial Sequence
<220> FEATURE:
<223> OTHER INFORMATION: TCRA Arm4 forward primer

<400> SEQUENCE: 50
gcgccacatg aatttgacca g                                      21

<210> SEQ ID NO 51
<211> LENGTH: 28
<212> TYPE: DNA
<213> ORGANISM: Artificial Sequence
<220> FEATURE:
<223> OTHER INFORMATION: TCRA Arm4 probe

```
<400> SEQUENCE: 51
tgtacccaat cttccaaaga aagagctg                                          28

<210> SEQ ID NO 52
<211> LENGTH: 19
<212> TYPE: DNA
<213> ORGANISM: Artificial Sequence
<220> FEATURE:
<223> OTHER INFORMATION: TCRA Arm4 reverse primer

<400> SEQUENCE: 52
ggcatcctgt cctcccttc                                                    19

<210> SEQ ID NO 53
<211> LENGTH: 27
<212> TYPE: DNA
<213> ORGANISM: Artificial Sequence
<220> FEATURE:
<223> OTHER INFORMATION: Parental 1540m1 forward primer

<400> SEQUENCE: 53
cagtaaggga agagactaca acagcat                                           27

<210> SEQ ID NO 54
<211> LENGTH: 27
<212> TYPE: DNA
<213> ORGANISM: Artificial Sequence
<220> FEATURE:
<223> OTHER INFORMATION: Parental 1540m1 probe

<400> SEQUENCE: 54
tgcacactgc tcaccactgc aagctat                                           27

<210> SEQ ID NO 55
<211> LENGTH: 17
<212> TYPE: DNA
<213> ORGANISM: Artificial Sequence
<220> FEATURE:
<223> OTHER INFORMATION: Parental 1540m1 reverse primer

<400> SEQUENCE: 55
tgctggtggc cccatct                                                      17

<210> SEQ ID NO 56
<211> LENGTH: 28
<212> TYPE: DNA
<213> ORGANISM: Artificial Sequence
<220> FEATURE:
<223> OTHER INFORMATION: Parental 1540m3 forward primer

<400> SEQUENCE: 56
gaactcagct atgatagtgt cgaatgta                                          28

<210> SEQ ID NO 57
<211> LENGTH: 23
<212> TYPE: DNA
<213> ORGANISM: Artificial Sequence
<220> FEATURE:
<223> OTHER INFORMATION: Parental 1540m3 probe

<400> SEQUENCE: 57
cagcccagca gctgtgggtt ctc                                               23

<210> SEQ ID NO 58
```

```
<211> LENGTH: 25
<212> TYPE: DNA
<213> ORGANISM: Artificial Sequence
<220> FEATURE:
<223> OTHER INFORMATION: Parental 1540m3 reverse primer

<400> SEQUENCE: 58
gctcagggag aacacagaac ttaga                                              25

<210> SEQ ID NO 59
<211> LENGTH: 20
<212> TYPE: DNA
<213> ORGANISM: Artificial Sequence
<220> FEATURE:
<223> OTHER INFORMATION: hIgK5 forward primer

<400> SEQUENCE: 59
ccccgtcctc ctccttttc                                                     20

<210> SEQ ID NO 60
<211> LENGTH: 32
<212> TYPE: DNA
<213> ORGANISM: Artificial Sequence
<220> FEATURE:
<223> OTHER INFORMATION: hIgK5 probe

<400> SEQUENCE: 60
tcatgtccat taacccattt accttttgcc ca                                      32

<210> SEQ ID NO 61
<211> LENGTH: 19
<212> TYPE: DNA
<213> ORGANISM: Artificial Sequence
<220> FEATURE:
<223> OTHER INFORMATION: hIgK5 reverse primer

<400> SEQUENCE: 61
tgcaagtgct gccagcaag                                                     19

<210> SEQ ID NO 62
<211> LENGTH: 156
<212> TYPE: DNA
<213> ORGANISM: Artificial Sequence
<220> FEATURE:
<223> OTHER INFORMATION: mouse Tcra/5' Frt junction sequence

<400> SEQUENCE: 62
gtcttttttg ttcttcacag ttgagcttca tcaaagtcac atgggttaaa ctctatggag        60
tagtcagaac acactcttca gaagggactc ctgatttcaa agggtaccga agttcctatt       120
ccgaagttcc tattctctag aaagtatagg aacttc                                 156

<210> SEQ ID NO 63
<211> LENGTH: 132
<212> TYPE: DNA
<213> ORGANISM: Artificial Sequence
<220> FEATURE:
<223> OTHER INFORMATION: 3' Frt/human IgK junction sequence

<400> SEQUENCE: 63
gaagttccta ttccgaagtt cctattctct agaaagtata ggaacttcct agggtttcac        60
cggtggcgcg cctaacagag aggaaagtca aattataaag aatatgagat tcagaattct       120
gattaactgt gg                                                           132
```

```
<210> SEQ ID NO 64
<211> LENGTH: 124
<212> TYPE: DNA
<213> ORGANISM: Artificial Sequence
<220> FEATURE:
<223> OTHER INFORMATION: Human IgK/mouse Tcra junction sequence

<400> SEQUENCE: 64
gataaattat tttgtcagac aacaataaaa atcaatagca cgccctaaga gcggccgcca      60
ccgcggtgga gctcaggttt ccggtactta acaacagagc acagatttag tggtgaggga     120
ctct                                                                  124

<210> SEQ ID NO 65
<211> LENGTH: 28
<212> TYPE: DNA
<213> ORGANISM: Artificial Sequence
<220> FEATURE:
<223> OTHER INFORMATION: hIgK10 forward primer

<400> SEQUENCE: 65
cgattatgac tggttaggta gaaaggtg                                         28

<210> SEQ ID NO 66
<211> LENGTH: 32
<212> TYPE: DNA
<213> ORGANISM: Artificial Sequence
<220> FEATURE:
<223> OTHER INFORMATION: hIgK10 probe

<400> SEQUENCE: 66
gccactggtt tctccaaatg ttttcaatcc at                                    32

<210> SEQ ID NO 67
<211> LENGTH: 24
<212> TYPE: DNA
<213> ORGANISM: Artificial Sequence
<220> FEATURE:
<223> OTHER INFORMATION: hIgK10 reverse primer

<400> SEQUENCE: 67
gggagtactt ggagatccct aagc                                             24

<210> SEQ ID NO 68
<211> LENGTH: 136
<212> TYPE: DNA
<213> ORGANISM: Artificial Sequence
<220> FEATURE:
<223> OTHER INFORMATION: mouse Tcra/5' Frt junction sequence

<400> SEQUENCE: 68
ttgagcttca tcaaagtcac atgggttaaa ctctatggag tagtcagaac acactcttca      60
gaagggactc ctgatttcaa agggtaccga agttcctatt ccgaagttcc tattctctag     120
aaagtatagg aacttc                                                     136

<210> SEQ ID NO 69
<211> LENGTH: 132
<212> TYPE: DNA
<213> ORGANISM: Artificial Sequence
<220> FEATURE:
<223> OTHER INFORMATION: 3' Frt/human IgK junction sequence

<400> SEQUENCE: 69
gaagttccta ttccgaagtt cctattctct agaaagtata ggaacttcct agggtttcac      60
```

```
cggtggcgcg ccaggaccca ggctctgaca ctcaggctgc aatacaatt gccatgaaga      120 cagatgttga tg                                                         132
```

<210> SEQ ID NO 70
<211> LENGTH: 23
<212> TYPE: DNA
<213> ORGANISM: Artificial Sequence
<220> FEATURE:
<223> OTHER INFORMATION: gRNA#1 CRISPR recognition sequence

<400> SEQUENCE: 70

```
acgagcgggt tcggcccatt cgg                                             23
```

<210> SEQ ID NO 71
<211> LENGTH: 23
<212> TYPE: DNA
<213> ORGANISM: Artificial Sequence
<220> FEATURE:
<223> OTHER INFORMATION: gRNA#6 CRISPR recognition sequence

<400> SEQUENCE: 71

```
cttagccaga cgagcgggtt cgg                                             23
```

<210> SEQ ID NO 72
<211> LENGTH: 23
<212> TYPE: DNA
<213> ORGANISM: Artificial Sequence
<220> FEATURE:
<223> OTHER INFORMATION: gRNA#10 CRISPR recognition sequence

<400> SEQUENCE: 72

```
gccgatctta gccagacgag cgg                                             23
```

<210> SEQ ID NO 73
<211> LENGTH: 23
<212> TYPE: DNA
<213> ORGANISM: Artificial Sequence
<220> FEATURE:
<223> OTHER INFORMATION: gRNA#16 CRISPR recognition sequence

<400> SEQUENCE: 73

```
cgacctgatg cagctctcgg agg                                             23
```

<210> SEQ ID NO 74
<211> LENGTH: 21
<212> TYPE: DNA
<213> ORGANISM: Artificial Sequence
<220> FEATURE:
<223> OTHER INFORMATION: hIgK22 forward primer

<400> SEQUENCE: 74

```
tggctccaag aacagtttgc c                                               21
```

<210> SEQ ID NO 75
<211> LENGTH: 28
<212> TYPE: DNA
<213> ORGANISM: Artificial Sequence
<220> FEATURE:
<223> OTHER INFORMATION: hIgK22 probe

<400> SEQUENCE: 75

```
ccctgacttt gctgctcaac tcacagcc                                        28
```

<210> SEQ ID NO 76
<211> LENGTH: 21

```
<212> TYPE: DNA
<213> ORGANISM: Artificial Sequence
<220> FEATURE:
<223> OTHER INFORMATION: hIgK22 reverse primer

<400> SEQUENCE: 76
ggtccagtgg aatctgccat g                                              21

<210> SEQ ID NO 77
<211> LENGTH: 23
<212> TYPE: DNA
<213> ORGANISM: Artificial Sequence
<220> FEATURE:
<223> OTHER INFORMATION: hIgK21 forward primer

<400> SEQUENCE: 77
catttggcta catatcaaag ccg                                            23

<210> SEQ ID NO 78
<211> LENGTH: 27
<212> TYPE: DNA
<213> ORGANISM: Artificial Sequence
<220> FEATURE:
<223> OTHER INFORMATION: hIgK21 probe

<400> SEQUENCE: 78
cctgagccag ggaacagccc actgata                                        27

<210> SEQ ID NO 79
<211> LENGTH: 20
<212> TYPE: DNA
<213> ORGANISM: Artificial Sequence
<220> FEATURE:
<223> OTHER INFORMATION: hIgK21 reverse primer

<400> SEQUENCE: 79
acatggctga ggcagacacc                                                20

<210> SEQ ID NO 80
<211> LENGTH: 21
<212> TYPE: DNA
<213> ORGANISM: Artificial Sequence
<220> FEATURE:
<223> OTHER INFORMATION: hIgK26 forward primer

<400> SEQUENCE: 80
tgggccgtta tgctagtacc a                                              21

<210> SEQ ID NO 81
<211> LENGTH: 25
<212> TYPE: DNA
<213> ORGANISM: Artificial Sequence
<220> FEATURE:
<223> OTHER INFORMATION: hIgK26 probe

<400> SEQUENCE: 81
tggctttacc cctttgaag ggccc                                           25

<210> SEQ ID NO 82
<211> LENGTH: 21
<212> TYPE: DNA
<213> ORGANISM: Artificial Sequence
<220> FEATURE:
<223> OTHER INFORMATION: hIgK26 reverse primer

<400> SEQUENCE: 82
```
cacagctgaa gcaggatgag c 21

<210> SEQ ID NO 83
<211> LENGTH: 19
<212> TYPE: DNA
<213> ORGANISM: Artificial Sequence
<220> FEATURE:
<223> OTHER INFORMATION: hIgK30 forward primer

<400> SEQUENCE: 83
tctctgagca gccatcccc 19

<210> SEQ ID NO 84
<211> LENGTH: 27
<212> TYPE: DNA
<213> ORGANISM: Artificial Sequence
<220> FEATURE:
<223> OTHER INFORMATION: hIgK30 probe

<400> SEQUENCE: 84
ttctcctttg gtgtagaggg caccagc 27

<210> SEQ ID NO 85
<211> LENGTH: 19
<212> TYPE: DNA
<213> ORGANISM: Artificial Sequence
<220> FEATURE:
<223> OTHER INFORMATION: hIgK30 reverse primer

<400> SEQUENCE: 85
accaggcatg gcagaaagg 19

<210> SEQ ID NO 86
<211> LENGTH: 130
<212> TYPE: DNA
<213> ORGANISM: Artificial Sequence
<220> FEATURE:
<223> OTHER INFORMATION: 3' Frt/human IgK junction

<400> SEQUENCE: 86
gaagttccta ttccgaagtt cctattctct agaaagtata ggaacttcct agggtttcac 60
cggtggcgcg cctgagtagt gctttaggtg tgtaatcacc aaagatttag tgaagtccct 120
gtgcaaggag 130

METHODS AND COMPOSITIONS FOR TARGETED GENETIC MODIFICATION THROUGH SINGLE-STEP MULTIPLE TARGETING

CROSS-REFERENCE TO RELATED APPLICATIONS

This application is related to U.S. Application No. 62/094,104, filed Dec. 19, 2014, U.S. Application No. 62/167,408, filed May 28, 2015, and U.S. Application No. 62/205,524, filed Aug. 14, 2015, each of which is incorporated herein by reference in its entirety for all purposes.

REFERENCE TO A SEQUENCE LISTING SUBMITTED AS A TEXT FILE VIA EFS WEB

The Sequence Listing written in file 467864SEQLIST.txt is 16.7 kb, was created on Dec. 16, 2015, and is hereby incorporated by reference.

BACKGROUND

Homologous recombination using targeting vectors designed to add, delete, or replace a particular nucleic acid sequence at a genomic locus is a popular approach to achieving a desired genomic modification in non-human animals.

Although the art of genome modification through homologous recombination has advanced considerably over the last two decades, difficulties still remain with achieving an acceptable targeting frequency using very large targeting vectors, LTVECs, in many circumstances, for example, when a large portion of a rodent genome is replaced with a large human genomic fragment, or targeting certain cell types, e.g., fibroblasts or other somatic cells.

SUMMARY

Methods and compositions are provided for modifying a target genomic locus within a cell via a targeting system that utilizes two or more targeting vectors that are capable of recombining with one another to form a single contiguous nucleic acid segment. Optionally, the targeting vectors are large targeting vectors (LTVECs). Optionally, the LTVECs are each at least 10 kb in size.

The invention provides methods for modifying a target genomic locus in a cell, comprising: (a) introducing into the cell a nuclease agent that makes a single or double-strand break within a target genomic locus; (b) introducing into the cell a first large targeting vector (LTVEC) comprising a first nucleic acid insert flanked by a first 5' homology arm and a first 3' homology arm, and a second LTVEC comprising a second nucleic acid insert flanked by a second 5' homology arm and a second 3' homology arm, wherein the first 5' homology arm of the first LTVEC and the second 3' homology arm of the second LTVEC are homologous to corresponding genomic segments within the target genomic locus and the first 3' homology arm of the first LTVEC and the second 5' arm of the second LTVEC are homologous to each other or respectively to further 5' and 3' homology arms of one or more further LTVECs, each comprising a further nucleic acid insert flanked by a further 5' homology arm and a further 3' homology arm, wherein the target genomic locus is modified by integration of the first nucleic acid insert, the one or more further nucleic acid inserts of the one or more further LTVECs if present, and the second nucleic acid insert between the corresponding genomic segments; and (c) selecting a targeted cell comprising the first nucleic acid insert, the one or more further nucleic acid inserts if present, and the second nucleic acid insert integrated in the target genomic locus. Optionally, the first LTVEC, the second LTVEC, and the one or more further LTVECs are each at least 10 kb in size. In some such methods, the further LTVECs are one or more other LTVECs that, when present, are inserted between the first LTVEC and the second LTVEC.

The invention also provides double targeting methods for modifying a target genomic locus in a cell, comprising (a) introducing into the cell a nuclease agent that makes a single or double-strand break within the target genomic locus; (b) introducing into the cell a first large targeting vector (LTVEC) that is at least 10 kb in size and comprises a first nucleic acid insert flanked by a first 5' homology arm and a first 3' homology arm, and a second LTVEC that is at least 10 kb in length and comprises a second nucleic acid insert flanked by a second 5' homology arm and a second 3' homology arm, wherein the first 3' homology arm of the first LTVEC has a first overlapping sequence homologous to the second 5' homology arm of the second LTVEC, and the first 5' homology arm of the first LTVEC and the second 3' homology arm of the second LTVEC are homologous to corresponding genomic segments within the target genomic locus, wherein the target genomic locus is modified by integration of the first nucleic acid insert and the second nucleic acid insert between the corresponding genomic segments; and (c) selecting a targeted cell comprising the first nucleic acid insert and the second nucleic acid insert integrated into the target genomic locus.

Optionally, the first nucleic insert and the first 3' homology arm and the second nucleic acid insert and second 5' homology arm are overlapping fragments of a contiguous nucleic acid, which is reformed by integration of the first nucleic acid insert and the second nucleic acid insert into the target genomic locus.

In some such methods, the cell is a human cell. In other such methods, the cell is a non-human cell. In some such methods, the cell is a pluripotent cell, a hematopoietic stem cell, a neuronal stem cell, or a fibroblast cell. Optionally, the pluripotent cell is an embryonic stem (ES) cell or an induced pluripotent stem (iPS) cell. In some such methods, the cell is a mammalian cell. Optionally, the mammalian cell is a rodent cell. Optionally, the rodent cell is a mouse cell or a rat cell.

In some of the above methods, the nuclease agent is a zinc finger nuclease (ZFN), a Transcription Activator-Like Effector Nuclease (TALEN), or a meganuclease. In some of the above methods, the nuclease agent comprises a Clustered Regularly Interspaced Short Palindromic Repeats (CRISPR)-associated (Cas) protein and a guide RNA (gRNA). Optionally, the Cas protein is Cas9.

In some methods, the first nucleic acid insert, the second nucleic acid insert, or both are from a species that is different from the species of the cell. In some methods, the first nucleic acid insert, the second nucleic acid insert, or both are human nucleic acids.

In some methods, the combined size of the first nucleic acid insert and the second nucleic acid insert is from about 50 kb to about 500 kb, from about 50 kb to about 300 kb, from about 50 kb to about 75 kb, from about 75 kb to about 100 kb, from about 100 kb to about 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb, from about 275 kb to about 300 kb, from about 300 kb to about 350 kb, from about 350 kb to about 400 kb, from about 400 kb to about 450 kb, or from about 450 kb to about 500 kb. Optionally, the combined size of the first nucleic acid insert and the second nucleic acid insert is from about 100 kb to about 500 kb. Optionally, the combined size of the first nucleic acid insert and the second nucleic acid insert is about 300 kb.

In some methods, the targeted cell comprises genomic DNA comprising the first nucleic acid insert and the second nucleic acid insert together, which have a combined size ranging from about 5 kb to about 500 kb.

In some methods, the first overlapping sequence of the first LTVEC is at least 70%, 75%, 80%, 85%, 90%, 95%, 96%, 97%, 98%, 99%, 99.5%, or 99.9% identical to the first overlapping sequence of the second LTVEC. In some methods, the size of the first overlapping sequence is from about 1 kb to about 70 kb. In some methods, the size of the first overlapping sequence is at least 10 kb or at least 20 kb.

In some methods, integration of the first nucleic acid insert, the second nucleic acid insert, or both into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof. Optionally, the deletion of the endogenous sequence at the target genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb.

In some methods, combined use of the first LTVEC and the second LTVEC results in an increased targeting efficiency compared to use of a single LTVEC. Optionally, the increase in targeting efficiency is at least 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold.

In some methods, the sum total of the 5' and the 3' homology arms of the first LTVEC or the second LTVEC is from about 10 kb to about 150 kb. In some methods, the sum total of the 5' and the 3' homology arms of the first LTVEC is from about 10 kb to about 150 kb, and the sum total of the 5' and the 3' homology arms of the second LTVEC is from about 10 kb to about 150 kb. In some methods, the sum total of the 5' and the 3' homology arms of the first LTVEC or the second LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb. In some methods, the sum total of the 5' and the 3' homology arms of the first LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb, and the sum total of the 5' and the 3' homology arms of the second LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb.

The invention also provides methods for producing an F0 generation non-human animal, comprising: (a) introducing a non-human ES cell into a non-human host embryo, wherein the non-human ES cell was produced by any of the above methods; and (b) gestating the non-human host embryo in a surrogate mother, wherein the surrogate mother produces the F0 generation non-human animal comprising the modification. Optionally, the non-human animal is a mouse or a rat.

The invention also provides triple targeting methods for modifying a target genomic locus in a cell, comprising: (a) introducing into the cell a nuclease agent that makes a single or double-strand break within the target genomic locus; (b) introducing into the cell a first large targeting vector (LTVEC) that is at least 10 kb in length and comprises a first nucleic acid insert flanked by a first 5' homology arm and a first 3' homology arm, a second LTVEC that is at least 10 kb in length and comprises a second nucleic acid insert flanked by a second 5' homology arm and a second 3' homology arm, and a third LTVEC that is at least 10 kb in length and comprises a third nucleic acid insert flanked by a third 5' homology arm and a third 3' homology arm, wherein the first 3' homology arm of the first LTVEC has a first overlapping sequence homologous to the second 5' homology arm of the second LTVEC, the second 3' homology arm of the second LTVEC has a second overlapping sequence homologous to the third 5' homology arm of the third LTVEC, and the first 5' homology arm of the first LTVEC and the third 3' homology arm of the third LTVEC are homologous to corresponding genomic segments within the target genomic locus, wherein the target genomic locus is modified by integration of the first nucleic acid insert, the second nucleic acid insert, and the third nucleic acid insert between the corresponding genomic segments; and (c) selecting a targeted cell comprising the first nucleic acid insert, the second nucleic acid insert, and the third nucleic acid insert integrated into the target genomic locus.

Optionally, the first nucleic insert and the first 3' homology arm and the second nucleic acid insert and second 5' homology arm are overlapping fragments of a contiguous nucleic acid, and the second nucleic insert and the second 3' homology arm and the third nucleic acid insert and third 5' homology arm are overlapping fragments of the contiguous nucleic acid, which is reformed by integration of the first nucleic acid insert, the second nucleic acid insert, and the third nucleic acid insert into the target genomic locus.

In some such methods, the cell is a human cell. In other such methods, the cell is a non-human cell. In some such methods, the cell is a pluripotent cell, a hematopoietic stem cell, a neuronal stem cell, or a fibroblast cell. Optionally, the pluripotent cell is an embryonic stem (ES) cell or an induced pluripotent stem (iPS) cell. In some such methods, the cell is a mammalian cell. Optionally, the mammalian cell is a rodent cell. Optionally, the rodent cell is a mouse cell or a rat cell.

In some such methods, the nuclease agent is a zinc finger nuclease (ZFN), a Transcription Activator-Like Effector Nuclease (TALEN), or a meganuclease. In some such methods, the nuclease agent comprises a Clustered Regularly Interspaced Short Palindromic Repeats (CRISPR)-associated (Cas) protein and a guide RNA (gRNA). Optionally, the Cas protein is Cas9.

In some such methods, one or more of the first nucleic acid insert, the second nucleic acid insert, and the third nucleic acid insert are from a species that is different from the species of the cell. In some such methods, the first nucleic acid insert, the second nucleic acid insert, and the third nucleic acid insert are human nucleic acids.

In some such methods, the combined size of the first nucleic acid insert, the second nucleic acid insert, and the third nucleic acid insert is from about 50 kb to about 700 kb, from about 50 kb to about 500 kb, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb, from about 275 kb to about 300 kb, from about 300 kb to about 350 kb, from about 350 kb to about 400 kb, from about 400 kb to about 450 kb, from about 450 kb to about 500 kb, from about 500 kb to about 550 kb, from about 550 kb to about 600 kb, from about 600 kb to about 650 kb, or from about 650 kb to about 700 kb. Optionally, the combined size of the first nucleic acid insert, the second nucleic acid insert, and the third nucleic acid insert is from about 100 kb to about 700 kb. Optionally, the combined size of the first nucleic acid insert, the second nucleic acid insert, and the third nucleic acid insert is about 400 kb.

In some such methods, the targeted cell comprises genomic DNA comprising the first nucleic acid insert, the second nucleic acid insert, and the third nucleic acid insert together, which have a combined size ranging from about 5 kb to about 700 kb.

In some such methods, the first overlapping sequence of the first LTVEC is at least 70%, 75%, 80%, 85%, 90%, 95%, 96%, 97%, 98%, 99%, 99.5%, or 99.9% identical to the first overlapping sequence of the second LTVEC, and/or the second overlapping sequence of the second LTVEC is at least 70%, 75%, 80%, 85%, 90%, 95%, 96%, 97%, 98%, 99%, 99.5%, or 99.9% identical to the second overlapping sequence of the third LTVEC. In some such methods, the size of the first overlapping sequence is from about 1 kb to about 70 kb, and/or the size of the second overlapping sequence is from about 1 kb to about 70 kb. In some such methods, the size of the first overlapping sequence is at least 10 kb or at least 20 kb, and/or the size of the second overlapping sequence is at least 10 kb or at least 20 kb.

In some such methods, integration of one or more of the first nucleic acid insert, the second nucleic acid insert, and the third nucleic acid insert into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof. Optionally, the deletion of the endogenous sequence at the target genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb.

In some methods, the sum total of the 5' and the 3' homology arms of the first LTVEC, the second LTVEC, or the third LTVEC is from about 10 kb to about 150 kb. In some methods, the sum total of the 5' and the 3' homology arms of the first LTVEC is from about 10 kb to about 150 kb, the sum total of the 5' and the 3' homology arms of the second LTVEC is from about 10 kb to about 150 kb, and the sum total of the 5' and the 3' homology arms of the third LTVEC is from about 10 kb to about 150 kb. In some such methods, the sum total of the 5' and the 3' homology arms of the first LTVEC, the second LTVEC, or the third LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb. In some methods, the sum total of the 5' and the 3' homology arms of the first LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb; the sum total of the 5' and the 3' homology arms of the second LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb; and the sum total of the 5' and the 3' homology arms of the third LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb.

The invention also provides methods for producing an F0 generation non-human animal, comprising: (a) introducing a non-human ES cell into a non-human host embryo, wherein the non-human ES cell was produced by any of the above methods; and (b) gestating the non-human host embryo in a surrogate mother; wherein the surrogate mother produces the F0 generation non-human animal comprising the modification. Optionally, the non-human animal is a mouse or a rat.

The invention also provides methods for enhancing homologous recombination at a target genomic locus in a cell, comprising introducing into the cell a first nucleic acid and a second nucleic acid, wherein the first and the second nucleic acids comprise an overlapping nucleotide sequence. In some such methods, homologous recombination is enhanced compared to methods in which only a single nucleic acid is introduced into the cell.

In some such methods, homologous recombination is enhanced at the target genomic locus without using a nuclease agent. Some such methods further comprise introducing into the cell a nuclease agent that makes a single or double-strand break at or near the target genomic locus. In some such methods, the nuclease agent is a zinc finger nuclease (ZFN), a Transcription Activator-Like Effector Nuclease (TALEN), or a meganuclease. In some such methods, the nuclease agent comprises a Clustered Regularly Interspaced Short Palindromic Repeats (CRISPR)-associated (Cas) protein and a guide RNA (gRNA). Optionally, the Cas protein is Cas9.

In some such methods, the method enhances the homologous recombination of the first nucleic acid, the second nucleic acid, or both at the target genomic locus. Some such methods enhance the homologous recombination of the first nucleic acid at the target genomic locus compared to methods in which the first nucleic acid is introduced without the second nucleic acid. Some such methods enhance the homologous recombination of the second nucleic acid at the target genomic locus compared to methods in which the second nucleic acid is introduced without the first nucleic acid. Optionally, the enhancement of the homologous recombination is at least 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold.

In some such methods, the overlapping sequence of the first nucleic acid is at least 70%, 75%, 80%, 85%, 90%, 95%, 96%, 97%, 98%, 99%, 99.5%, or 99.9% identical to the overlapping sequence of the second nucleic acid. In some such methods, the overlapping sequence is from about 1 kb to about 70 kb. Optionally, the overlapping sequence is from about 1 kb to about 5 kb, from about 5 kb to about 10 kb, from about 10 kb to about 15 kb, from about 15 kb to about 20 kb, from about 20 kb to about 25 kb, from about 25 kb to about 30 kb, from about 30 kb to about 35 kb, from about 35 kb to about 40 kb, from about 40 kb to about 45 kb, from about 45 kb to about 50 kb, from about 50 kb to about 55 kb, from about 55 kb to about 60 kb, from about 60 kb to about 65 kb, or from about 65 kb to about 70 kb. In some such methods, the overlapping sequence is at least 5 kb, at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, or at least 70 kb. Optionally, the overlapping sequence is at least 20 kb.

In some such methods, the first nucleic acid is a targeting vector comprising a first nucleic acid insert flanked by a first 5' homology arm and a first 3' homology arm, and the second nucleic acid does not comprise a nucleotide sequence that is homologous to the target genomic locus except the overlapping sequence. Optionally, the first targeting vector is from about 1 kb to about 2 kb, from about 2 kb to about 5 kb, or about 5 kb to about 10 kb. Optionally, the first targeting vector is a first large targeting vector (LTVEC). Optionally, the first LTVEC is at least 10 kb in length. Optionally, the first targeting vector is a first large targeting vector (LTVEC) ranging from about 20 kb to about 200 kb. Optionally, the sum total of the 5' and the 3' homology arms of the first LTVEC is from 10 kb to about 200 kb.

In some such methods, the first nucleic acid is a first targeting vector comprising a first nucleic acid insert flanked by a first 5' homology arm and a first 3' homology arm, and the second nucleic acid is a second targeting vector comprising a second nucleic acid insert flanked by a second 5' homology arm and a second 3' homology arm. Optionally, the first targeting vector is from about 1 kb to about 2 kb, from about 2 kb to about 5 kb, or 5 kb to about 10 kb, and/or the second targeting vector is from about 1 kb to about 2 kb, from about 2 kb to about 5 kb, or about 5 kb to about 10 kb. Optionally, the first targeting vector is a first large targeting vector (LTVEC) and/or the second targeting vector is a second large targeting vector (LTVEC). Optionally, the first LTVEC is at least 10 kb in length and/or the second LTVEC is at least 10 kb in length. Optionally, the first targeting vector is a first large targeting vector (LTVEC) ranging from about 20 kb to about 200 kb, and/or the second targeting vector is a second large targeting vector (LTVEC) ranging from about 20 kb to about 200 kb. Optionally, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb, and/or the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. Optionally, the sum total of the 5' and the 3' homology arms of the first LTVEC or the second LTVEC is from 10 kb to about 200 kb. Optionally, the sum total of the 5' and the 3' homology arms of the first LTVEC is from 10 kb to about 200 kb, and the sum total of the 5' and the 3' homology arms of the second LTVEC is from 10 kb to about 200 kb.

In some methods, the overlapping sequence is located at the 3' end of the first nucleic acid and the 5' end of the second nucleic acid sequence. In some methods, the overlapping nucleotide sequence facilitates recruitment of recombination machinery to the target genomic locus.

In some such methods, the cell is a human cell. In other such methods, the cell is a non-human cell. In some such methods, the cell is a pluripotent cell, a hematopoietic stem cell, a neuronal stem cell, or a fibroblast cell. Optionally, the pluripotent cell is an embryonic stem (ES) cell or an induced pluripotent stem (iPS) cell. In some such methods, the cell is a mammalian cell. Optionally, the mammalian cell is a rodent cell. Optionally, the rodent cell is a mouse cell or a rat cell.

The invention also provides methods for producing an F0 generation non-human animal, comprising: (a) introducing a non-human ES cell into a non-human host embryo, wherein the non-human ES cell was produced by any of the above methods; and (b) gestating the non-human host embryo in a surrogate mother; wherein the surrogate mother produces the F0 generation non-human animal comprising the modification. Optionally, the non-human animal is a mouse or a rat.

Methods and compositions are provided for modifying a target genomic locus within a cell via a targeting system that utilizes two or more targeting vectors that are capable of recombining with one another to form a single contiguous nucleic acid segment. In various embodiments, the targeting vectors are large targeting vectors (LTVECs). Optionally, the LTVECs are each at least 10 kb in size.

In one embodiment, a method for modifying a target genomic locus in a cell is provided. Such a method comprises introducing into a cell a nuclease agent that makes a single or double-strand break within a target genomic locus, introducing a first large targeting vector (LTVEC) comprising a first nucleic acid insert flanked by a first 5' homology arm and a first 3' homology arm, and a second LTVEC comprising a second nucleic acid insert flanked by a second 5' homology arm and a second 3' homology arm, wherein the first 5' homology arm of the first LTVEC and the second 3' homology arm of the second LTVEC are homologous to corresponding segments within the target locus and the first 3' homology arm of the first LTVEC and the second 5' arm of the second LTVEC are homologous to each other or respectively to further 5' and 3' homology arms of one or more further LTVECs, each comprising a further insert flanked by a further 5' homology arm and a further 3' homology arm; wherein the target genomic locus is modified by integration of the first insert, the one or more further inserts of the one or more further LTVECs if present, and the second nucleic acid insert between the corresponding genomic segments. Optionally, the first LTVEC, the second LTVEC, and the one or more further LTVECs are each at least 10 kb in size. The method further comprises selecting a targeted cell comprising the first nucleic acid insert, the one or more further nucleic acid inserts if present, and the second nucleic acid insert integrated in the target genomic locus. In such methods, the further LTVECs are one or more other LTVECs that, when present, are inserted between the first LTVEC and the second LTVEC.

In another embodiment, a double targeting method for modifying a target genomic locus in a cell is provided. Such a method comprises introducing into a cell a nuclease agent that makes a single or double-strand break within a target genomic locus, introducing a first large targeting vector (LTVEC) comprising a first nucleic acid insert flanked by a first 5' homology arm and a first 3' homology arm, and a second LTVEC comprising a second nucleic acid insert flanked by a second 5' homology arm and a second 3' homology arm. Optionally, the first LTVEC is at least 10 kb in size and the second LTVEC is at least 10 kb in size. In such a method, the first 3' homology arm of the first LTVEC has a first overlapping sequence homologous to the second 5' homology arm of the second LTVEC and the first 5' homology arm of the first LTVEC and the second 3' homology arm of the second LTVEC are homologous to corresponding segments within the target locus, such that the target genomic locus is modified by integration of the first and second nucleic acid inserts between the corresponding genomic segments. The method further comprises selecting a targeted cell comprising the first nucleic acid insert and the second nucleic acid insert integrated in the target genomic locus.

In some such methods, the first nucleic insert and the first 3' homology arm and the second nucleic acid insert and second 5' homology arm are overlapping fragments of a contiguous nucleic acid, which is reformed by integration of the first nucleic acid insert and the second nucleic acid insert into the target genomic locus.

In another embodiment, a triple targeting method for modifying a target genomic locus in a cell is provided. Such a method comprises introducing into a cell a nuclease agent that makes a single or double-strand break within a target genomic locus, introducing a first large targeting vector (LTVEC) comprising a first nucleic acid insert flanked by a first 5' homology arm and a first 3' homology arm, a second LTVEC comprising a second nucleic acid insert flanked by a second 5' homology arm and a second 3' homology arm, and a third LTVEC comprising a third nucleic acid insert flanked by a third 5' homology arm and a third 3' homology arm. Optionally, the first LTVEC is at least 10 kb in size, the second LTVEC is at least 10 kb in size, and the third LTVEC is at least 10 kb in size. In such a method, the first 3' homology arm of the first LTVEC has a first overlapping sequence homologous to the second 5' homology arm of the second LTVEC, the second 3' homology arm of the second LTVEC has a second overlapping sequence homologous to the third 5' homology arm of the third LTVEC, and the first 5' homology arm of the first LTVEC and the third 3' homology arm of the third LTVEC are homologous to corresponding segments within the target locus, such that the target genomic locus is modified by integration of the first, the second, and the third nucleic acid inserts between the corresponding genomic segments. The method further comprises selecting a targeted cell comprising the first nucleic acid insert, the second nucleic acid insert, and the third nucleic acid insert integrated in the target genomic locus.

In some such methods, the first nucleic insert and the first 3' homology arm and the second nucleic acid insert and second 5' homology arm are overlapping fragments of a contiguous nucleic acid, and the second nucleic insert and the second 3' homology arm and the third nucleic acid insert and third 5' homology arm are overlapping fragments of a contiguous nucleic acid, which is reformed by integration of the first nucleic acid insert, the second nucleic acid insert, and the third nucleic acid insert into the target genomic locus.

In one embodiment, the cell is a pluripotent cell. In another embodiment, the pluripotent cell is an embryonic stem (ES) cell. In some embodiments, the pluripotent cell is a hematopoietic stem cell or a neuronal stem cell. In another embodiment, the cell is an induced pluripotent stem (iPS) cell.

In one embodiment the target genomic locus is in the genome of the cell. In another embodiment, the target genomic locus is on extrachromosomal DNA within the cell.

In one embodiment, the cell is a fibroblast cell.

In some methods, the cell is a non-human cell. In other methods, the cell is from a human. In some embodiments the cell is a mammalian cell. In another embodiment, the mammalian cell is from a rodent. In some cases, the rodent is a mouse, a rat, or a hamster.

In some of the above methods, the nuclease agent is expressed from an expression construct comprising a nucleic acid sequence encoding a nuclease, and wherein the nucleic acid is operably linked to a promoter active in the cell. In other methods, the nuclease agent is expressed from an mRNA encoding the nuclease. In some such methods, the nuclease is a zinc finger nuclease (ZFN). In other such methods, the nuclease is a Transcription Activator-Like Effector Nuclease (TALEN). In yet other methods, the nuclease is a meganuclease.

In some of the above methods, the nuclease agent comprises a Clustered Regularly Interspaced Short Palindromic Repeats (CRISPR)-associated (Cas) protein and a guide RNA (gRNA). In some such methods, the Cas protein is Cas9.

In some of the above methods, the first nucleic acid insert, the second nucleic acid insert, or both are from a species that is different from the species of the cell. In one embodiment, the first nucleic acid insert, the second nucleic acid insert, and/or the third nucleic acid insert are from a different species. In some methods, one of more of the first nucleic acid insert, the second nucleic acid insert, and the third nucleic acid insert are from a species different from the species of the cell. In some methods, the first nucleic acid insert, the second nucleic acid insert, or both are human nucleic acids. In another embodiment, the first nucleic acid insert, the second nucleic acid insert, and/or the third nucleic acid insert are human nucleic acids. In some methods, one of more of the first nucleic acid insert, the second nucleic acid insert, and the third nucleic acid insert are human nucleic acids.

In one embodiment, the combined size of the first and the second nucleic acid inserts is from about 50 kb to about 500 kb, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb, from about 275 kb to about 300 kb, from about 300 kb to about 350 kb, from about 350 kb to about 400 kb, from about 400 kb to about 450 kb, or from about 450 kb to about 500 kb. In another embodiment, the combined size of the first and the second nucleic acid inserts is from about 100 kb to about 500 kb. In yet another embodiment, the combined size of the first and the second nucleic acid inserts is about 300 kb.

In some embodiments, the targeted cell comprises a genomic DNA comprising the first and the second nucleic acid inserts together ranging from about 5 kb to about 500 kb.

In one embodiment, the combined size of the first, the second, and the third nucleic acid inserts is from about 50 kb to about 700 kb, from about 50 kb to about 500 kb, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb, from about 275 kb to about 300 kb, from about 300 kb to about 350 kb, from about 350 kb to about 400 kb, from about 400 kb to about 450 kb, from about 450 kb to about 500 kb, from about 500 kb to about 550 kb, from about 550 kb to about 600 kb, from about 600 kb to about 650 kb, or from about 650 kb to about 700 kb.

In some embodiments, the targeted cell comprises a genomic DNA comprising the first, the second, and the third nucleic acid inserts together ranging from about 5 kb to about 700 kb. Optionally, the combined size of the first nucleic acid insert, the second nucleic acid insert, and the third nucleic acid insert is from about 100 kb to about 700 kb. In some embodiments, the combined size of the first, the second, and the third nucleic acid inserts is about 400 kb.

In some of the above methods, the first overlapping sequence of the first LTVEC is at least 70%, 75%, 80%, 85%, 90%, 95%, 96%, 97%, 98%, 99%, 99.5%, or 99.9% identical to the first overlapping sequence of the second LTVEC. In some of the above methods, the second overlapping sequence of the second LTVEC is at least 70%, 75%, 80%, 85%, 90%, 95%, 96%, 97%, 98%, 99%, 99.5%, or 99.9% identical to the second overlapping sequence of the third LTVEC. In any of the above methods, the overlapping sequence is from about 1 kb to about 70 kb. In a specific embodiment, the overlapping sequence is at least 10 kb. In another specific embodiment, the overlapping sequence is at least 20 kb. In some of the above methods, the first overlapping sequence and/or the second overlapping sequence is from about 1 kb to about 70 kb. In some methods, the first overlapping sequence and/or the second overlapping sequence is at least 10 kb or at least 20 kb.

In some methods, integration of the first nucleic acid insert, the second nucleic acid insert, or both into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof. In some methods, integration of one or more of the first, the second and the third nucleic acid inserts into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof.

In some methods, integration of the first nucleic acid insert, the second nucleic acid insert, or both into the target genomic locus results in an addition of an exogenous sequence at the target genomic locus. In one embodiment, integration of the first, the second and/or the third nucleic acid inserts into the target genomic locus results in an addition of an exogenous sequence at the target genomic locus.

In some methods, integration of the first nucleic acid insert, the second nucleic acid insert, or both into the target genomic locus results in a deletion of an endogenous sequence at the target genomic locus. In another embodiment, integration of the first, the second, and/or the third nucleic acid inserts into the target genomic locus results in a deletion of an endogenous sequence at the target genomic locus. In some such methods the deletion of the endogenous sequence at the target genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb.

In some methods, integration of the first nucleic acid insert, the second nucleic acid insert, or both insert into the target genomic locus results in a knock-in, a knockout, a point mutation, a domain swap, an exon swap, an intron swap, a regulatory sequence swap, a gene swap, or a combination thereof. In yet another embodiment, integration of the first, the second, and/or the third nucleic acid inserts into the target genomic locus results in a knock-in, a knockout, a point mutation, a domain swap, an exon swap, an intron swap, a regulatory sequence swap, a gene swap, or a combination thereof.

In some of the above methods, combined use of the first LTVEC and the second LTVEC results in an increased targeting efficiency compared to use of a single LTVEC. Optionally, the increase in targeting efficiency is at least 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold.

In some methods, the sum total of the 5' and the 3' homology arms of the first LTVEC or the second LTVEC is from about 10 kb to about 150 kb. In some methods, the sum total of the 5' and the 3' homology arms of the first LTVEC is from about 10 kb to about 150 kb and the sum total of the 5' and the 3' homology arms of the second LTVEC is from about 10 kb to about 150 kb. In some embodiments, the sum total of the 5' and the 3' homology arms of the first LTVEC, the second LTVEC, or the third LTVEC is from about 10 kb to about 150 kb. In some methods, the sum total of the 5' and the 3' homology arms of the first LTVEC is from about 10 kb to about 150 kb, the sum total of the 5' and the 3' homology arms of the second LTVEC is from about 10 kb to about 150 kb, and the sum total of the 5' and the 3' homology arms of the third LTVEC is from about 10 kb to about 150 kb. In other embodiments, the sum total of the 5' and the 3' homology arms of the first LTVEC, the second LTVEC, or the third LTVEC is from about 1 kb to about 5 kb, from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb. In some methods, the sum total of the 5' and the 3' homology arms of the first LTVEC is from about 1 kb to about 5 kb, from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb; the sum total of the 5' and the 3' homology arms of the second LTVEC is from about 1 kb to about 5 kb, from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to about 150 kb; and the sum total of the 5' and the 3' homology arms of the third LTVEC is from about 1 kb to about 5 kb, from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

Further provided is a method for producing an F0 generation non-human animal. Such a method comprises introducing a non-human ES cell into a non-human host embryo, wherein the non-human ES cell was produced by any of the above methods, and gestating the non-human host embryo in a surrogate mother such that the surrogate mother produces the F0 generation non-human animal comprising the modification. Optionally, the non-human animal is a mouse or a rat.

The invention also provides methods for enhancing homologous recombination at a target genomic locus in a cell, comprising introducing into the cell a first nucleic acid and a second nucleic acid, wherein the first and the second nucleic acids comprise an overlapping nucleotide sequence. In some such methods, homologous recombination is enhanced compared to methods in which only a single nucleic acid is introduced into the cell. In some such methods, homologous recombination is enhanced at the target genomic locus without using a nuclease agent. Other such methods further comprise introducing into the cell a nuclease agent that makes a single or double-strand break at or near the target genomic locus.

In one aspect, a method is provided for enhancing homologous recombination at a genomic locus in a cell without using a nuclease agent, comprising introducing into the cell a first nucleic acid and a second nucleic acid, wherein the first and the second nucleic acids comprise an overlapping nucleotide sequence.

In one embodiment, the method enhances the homologous recombination of the first nucleic acid at the target genomic locus. Some such methods enhance the homologous recombination of the first nucleic acid at the target genomic locus compared to methods in which the first nucleic acid is introduced without the second nucleic acid. In one embodiment, the method enhances the homologous recombination of the second nucleic acid at the target genomic locus. Some such methods enhance the homologous recombination of the second nucleic acid at the target genomic locus compared to methods in which the second nucleic acid is introduced without the first nucleic acid. In one embodiment, the method increases the homologous recombination of the first and the second nucleic acids at the target genomic locus.

In one embodiment, the enhancement of the homologous recombination is at least 0.5-fold, 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold.

In one embodiment, the overlapping sequence of the first nucleic acid is homologous to the overlapping sequence of the second nucleic acid. In one embodiment, the overlapping sequence of the first nucleic acid is at least 70%, 75%, 80%, 85%, 90%, 95%, 96%, 97%, 98%, 99%, 99.5%, or 99.9% identical to the overlapping sequence of the second nucleic acid. In one embodiment, the overlapping sequence of the first nucleic acid is 100% identical to that overlapping sequence of the second nucleic acid.

In one embodiment, the overlapping sequence is from about 1 kb to about 70 kb. In some methods, the overlapping sequence is at least 20 kb. In one embodiment, the overlapping sequence is from about 1 kb to about 5 kb. In one embodiment, the overlapping sequence is from about 5 kb to about 10 kb. In one embodiment, the overlapping sequence is from about 10 kb to about 15 kb. In one embodiment, the overlapping sequence is from about 15 kb to about 20 kb. In one embodiment, the overlapping sequence is from about 20 kb to about 25 kb. In one embodiment, the overlapping sequence is from about 25 kb to about 30 kb. In one embodiment, the overlapping sequence is from about 30 kb to about 35 kb. In one embodiment, the overlapping sequence is from about 35 kb to about 40 kb. In one embodiment, the overlapping sequence is from about 40 kb to about 45 kb. In one embodiment, the overlapping sequence is from about 45 kb to about 50 kb. In one embodiment, the overlapping sequence is from about 50 kb to about 55 kb. In one embodiment, the overlapping sequence is from about 55 kb to about 60 kb. In one embodiment, the overlapping sequence is from about 60 kb to about 65 kb. In one embodiment, the overlapping sequence is from about 65 kb to about 70 kb.

In one embodiment, the overlapping sequence is at least 5 kb. In one embodiment, the overlapping sequence is at least 10 kb. In one embodiment the overlapping sequence is at least 15 kb. In one embodiment, the overlapping sequence is at least 20 kb. In one embodiment, the overlapping sequence is at least 25 kb. In one embodiment the overlapping sequence is at least 30 kb. In one embodiment, the overlapping sequence is at least 35 kb. In one embodiment the overlapping sequence is at least 40 kb. In one embodiment, the overlapping sequence is at least 45 kb. In one embodiment, the overlapping sequence is at least 50 kb. In one embodiment, the overlapping sequence is at least 55 kb. In one embodiment, the overlapping sequence is at least 60 kb. In one embodiment, the overlapping sequence is at least 65 kb. In one embodiment, the overlapping sequence is at least 70 kb.

In one embodiment, the first nucleic acid is a targeting vector comprising a first nucleic acid insert flanked by a first 5' homology arm and a first 3' homology arm, and the second nucleic acid does not comprise a nucleotide sequence that is homologous to the genomic locus except the overlapping sequence.

In one embodiment, the second nucleic acid is a second targeting vector comprising a second nucleic acid insert flanked by a second 5' homology arm and a second 3' homology arm, and the first nucleic acid does not comprise a nucleotide sequence that is homologous to the genomic locus except the overlapping sequence.

In one embodiment, the first nucleic acid is a first targeting vector comprising a first nucleic acid insert flanked by a first 5' homology arm and a first 3' homology arm, and the second nucleic acid is a second targeting vector comprising a second nucleic acid insert flanked by a second 5' homology arm and a second 3' homology arm. In one embodiment, the first nucleic acid insert and the second nucleic acid insert are overlapping fragments of a contiguous nucleic acid.

In one embodiment, the targeting vector is from about 1 kb to about 2 kb. In one embodiment, the targeting vector is from about 2 kb to about 5 kb. In one embodiment, the targeting vector is from about 5 kb to about 10 kb.

In one embodiment, the targeting vector is a large targeting vector (LTVEC). In some methods, the targeting vector is an LTVEC ranging from about 20 kb to about 200 kb. In some methods, the first targeting vector is a first LTVEC ranging from about 20 kb to about 200 kb, and/or the second targeting vector is a second LTVEC ranging from about 20 kb to about 200 kb. In one embodiment, the LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. In some methods, the first targeting vector is a first LTVEC and/or the second targeting vector is a second LTVEC. In some methods, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. In some methods, the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. In some methods, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb, and the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb.

In one embodiment, the sum total of the 5' and the 3' homology arms of the LTVEC is from 10 kb to about 200 kb. In some methods, the sum total of the 5' and the 3' homology arms of the first LTVEC is from 10 kb to about 200 kb. In some methods, the sum total of the 5' and the 3' homology arms of the second LTVEC is from 10 kb to about 200 kb. In some methods, the sum total of the 5' and the 3' homology arms of the first LTVEC is from 10 kb to about 200 kb, and the sum total of the 5' and the 3' homology arms of the second LTVEC is from 10 kb to about 200 kb.

In one embodiment, the overlapping sequence is located at the 3' end of the first nucleic acid and the 5' end of the second nucleic acid sequence. In one embodiment, the overlapping sequence is located at the 5' end of the first nucleic acid sequence and the 3' end of the second nucleic acid sequence.

In one embodiment, the first nucleic acid insert and/or the second nucleic acid insert are from a different species. In another embodiment, the first nucleic acid insert and/or the second nucleic acid insert are human nucleic acids. In some methods, the first nucleic acid insert, the second nucleic acid insert, or both are from a species different from the species of the cell. In some methods, the first nucleic acid insert, the second nucleic acid insert, or both are human nucleic acids.

In some methods, integration of the first nucleic acid insert, the second nucleic acid insert, or both into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof. In some methods, integration of one or more of the first, the second and the third nucleic acid inserts into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof.

In one embodiment, integration of the first and/or the second inserts into the genomic locus results in an addition of an exogenous sequence at the genomic locus.

In some embodiments, the targeted cell comprises a genomic DNA comprising the first and the second nucleic acid inserts together ranging from about 5 kb to about 500 kb. In some methods, the targeted cell comprises genomic DNA comprising the first and the second nucleic acid inserts together, which have a combined size ranging from about 5 kb to about 500 kb.

In another embodiment, integration of the first and/or the second nucleic acid inserts into the genomic locus results in a deletion of an endogenous sequence at the target genomic locus. In one embodiment, the deletion of the endogenous sequence at the target genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb.

In some methods, the cell is a human cell. In other methods, the cell is a non-human cell. In some methods, the cell is a pluripotent cell, a hematopoietic stem cell, a neuronal stem cell, or a fibroblast cell. Optionally, the pluripotent cell is an embryonic stem (ES) cell or an induced pluripotent stem (iPS) cell. In some methods, the cell is a mammalian cell. Optionally, the mammalian cell is a rodent cell. Optionally, the rodent cell is a mouse cell or a rat cell.

In one embodiment, the cell is a pluripotent cell. In another embodiment, the pluripotent cell is an embryonic stem (ES) cell. In some embodiments, the pluripotent cell is a hematopoietic stem cell or a neuronal stem cell. In another embodiment, the cell is an induced pluripotent stem (iPS) cell.

In one embodiment the target genomic locus is in the genome of the cell. In another embodiment, the target genomic locus is on extrachromosomal DNA within the cell.

In one embodiment, the cell is a fibroblast cell.

In some methods, the cell is a non-human cell. In other methods, the cell is from a human. In some embodiments the cell is a mammalian cell. In another embodiment, the mammalian cell is from a rodent. In some cases, the rodent is a mouse, a rat, or a hamster.

In some of the above methods, the overlapping nucleotide sequence facilitates recruitment of recombination machinery to the target genomic locus.

The invention also provides methods for producing an F0 generation non-human animal, comprising: (a) introducing a non-human ES cell into a non-human host embryo, wherein the non-human ES cell was produced by the above methods; and (b) gestating the non-human host embryo in a surrogate mother, wherein the surrogate mother produces the F0 generation non-human animal comprising the modification. Optionally, the non-human animal is a mouse or a rat.

In another aspect, a method is provided for enhancing homologous recombination at a target genomic locus in a cell with a nuclease agent, comprising introducing into the cell: (i) a first nucleic acid and a second nucleic acid, wherein the first and the second nucleic acids comprise an overlapping nucleotide sequence; and (ii) a nuclease agent that makes a single or double-strand break at or near the genomic locus.

In one embodiment, the method enhances the homologous recombination of the first nucleic acid at the target genomic locus. Some such methods enhance the homologous recombination of the first nucleic acid at the target genomic locus compared to methods in which the first nucleic acid is introduced without the second nucleic acid. In one embodiment, the method enhances the homologous recombination of the second nucleic acid at the target genomic locus. Some such methods enhance the homologous recombination of the second nucleic acid at the target genomic locus compared to methods in which the second nucleic acid is introduced without the first nucleic acid. In one embodiment, the method increases the homologous recombination of the first and the second nucleic acids at the target genomic locus. In one embodiment, the enhancement of the homologous recombination is at least 0.5-fold, 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold.

In one embodiment, the overlapping sequence of the first nucleic acid is homologous to the overlapping sequence of the second nucleic acid. In one embodiment, the overlapping sequence of the first nucleic acid is at least 70%, 75%, 80%, 85%, 90%, 95%, 96%, 97%, 98%, 99%, 99.5%, or 99.9% identical to the overlapping sequence of the second nucleic acid. In one embodiment, the overlapping sequence of the first nucleic acid is 100% identical to the overlapping sequence of the second nucleic acid.

In one embodiment, the overlapping sequence is from about 1 kb to about 70 kb. In one embodiment, the overlapping sequence is from about 1 kb to about 5 kb. In one embodiment, the overlapping sequence is from about 5 kb to about 10 kb. In one embodiment, the overlapping sequence is from about 10 kb to about 15 kb. In one embodiment, the overlapping sequence is from about 15 kb to about 20 kb. In one embodiment, the overlapping sequence is from about 20 kb to about 25 kb. In one embodiment, the overlapping sequence is from about 25 kb to about 30 kb. In one embodiment, the overlapping sequence is from about 30 kb to about 35 kb. In one embodiment, the overlapping sequence is from about 35 kb to about 40 kb. In one embodiment, the overlapping sequence is from about 40 kb to about 45 kb. In one embodiment, the overlapping sequence is from about 45 kb to about 50 kb. In one embodiment, the overlapping sequence is from about 50 kb to about 55 kb. In one embodiment, the overlapping sequence is from about 55 kb to about 60 kb. In one embodiment, the overlapping sequence is from about 60 kb to about 65 kb. In one embodiment, the overlapping sequence is from about 65 kb to about 70 kb.

In one embodiment, the overlapping sequence is at least 5 kb. In one embodiment, the overlapping sequence is at least 10 kb. In one embodiment the overlapping sequence is at least 15 kb. In one embodiment, the overlapping sequence is at least 20 kb. In one embodiment, the overlapping sequence is at least 25 kb. In one embodiment the overlapping sequence is at least 30 kb. In one embodiment, the overlapping sequence is at least 35 kb. In one embodiment the overlapping sequence is at least 40 kb. In one embodiment, the overlapping sequence is at least 45 kb. In one embodiment, the overlapping sequence is at least 50 kb. In one embodiment, the overlapping sequence is at least 55 kb. In one embodiment, the overlapping sequence is at least 60 kb. In one embodiment, the overlapping sequence is at least 65 kb. In one embodiment, the overlapping sequence is at least 70 kb.

In one embodiment, the first nucleic acid is a targeting vector comprising a first nucleic acid insert flanked by a first 5' homology arm and a first 3' homology arm, and the second nucleic acid does not comprise a nucleotide sequence that is homologous to the genomic locus except the overlapping sequence.

In one embodiment, the second nucleic acid is a second targeting vector comprising a second nucleic acid insert flanked by a second 5' homology arm and a second 3' homology arm, and the first nucleic acid does not comprise a nucleotide sequence that is homologous to the target genomic locus except the overlapping sequence.

In one embodiment, the first nucleic acid is a first targeting vector comprising a first nucleic acid insert flanked by a first 5' homology arm and a first 3' homology arm, and the second nucleic acid is a second targeting vector comprising a second nucleic acid insert flanked by a second 5' homology arm and a second 3' homology arm. In one embodiment, the first nucleic acid insert and the second nucleic acid insert are overlapping fragments of a contiguous nucleic acid.

In one embodiment, the targeting vector is from about 1 kb to about 2 kb. In one embodiment, the targeting vector is from about 2 kb to about 5 kb. In one embodiment, the targeting vector is from about 5 kb to about 10 kb.

In one embodiment, the targeting vector is a large targeting vector (LTVEC). In some methods, the targeting vector is a large targeting vector ranging from about 10 kb to about 200 kb. In some methods, the first targeting vector is a first LTVEC and/or the second targeting vector is a second LTVEC. In some methods, the first targeting vector is a first large targeting vector ranging from about 10 kb to about 200 kb, and/or the second targeting vector is a second large targeting vector ranging from about 10 kb to about 200 kb. In one embodiment, the LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. Optionally, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. Optionally, the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. In some methods, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb, and the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb.

In one embodiment, the sum total of the 5' and the 3' homology arms of the LTVEC is from 10 kb to about 200 kb. In some methods, the sum total of the 5' and 3' homology arms of the first LTVEC is from 10 kb to about 200 kb. In some methods, the sum total of the 5' and 3' homology arms of the second LTVEC is from 10 kb to about 200 kb. In some methods, the sum total of the 5' and 3' homology arms of the first LTVEC is from 10 kb to about 200 kb, and the sum total of the 5' and 3' homology arms of the second LTVEC is from 10 kb to about 200 kb.

In one embodiment, the overlapping sequence is located at the 3' end of the first nucleic acid and the 5' end of the second nucleic acid sequence. In one embodiment, the overlapping sequence is located at the 5' end of the first nucleic acid sequence and the 3' end of the second nucleic acid sequence.

In one embodiment, the nuclease agent is expressed from an expression construct comprising a nucleic acid sequence encoding a nuclease, and wherein the nucleic acid is operably linked to a promoter active in the cell. In one embodiment, the nuclease agent is expressed from an mRNA encoding the nuclease. In one embodiment, the nuclease is a zinc finger nuclease (ZFN). In one embodiment, the nuclease is a Transcription Activator-Like Effector Nuclease (TALEN). In one embodiment, the nuclease is a meganuclease.

In one embodiment, the nuclease agent comprises a Clustered Regularly Interspaced Short Palindromic Repeats (CRISPR)-associated (Cas) protein and a guide RNA (gRNA). In one embodiment, the Cas protein is Cas9.

In one embodiment, the first nucleic acid insert and/or the second nucleic acid insert are from a different species. In another embodiment, the first nucleic acid insert and/or the second nucleic acid insert are human nucleic acids. In some methods, the first nucleic acid insert, the second nucleic acid insert, or both are from a species different from the species of the cell. In some methods, the first nucleic acid insert, the second nucleic acid insert, or both are human nucleic acids.

In some methods, integration of the first nucleic acid insert, the second nucleic acid insert, or both into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof. In some methods, integration of one or more of the first, the second and the third nucleic acid inserts into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof.

In one embodiment, integration of the first and/or the second inserts into the genomic locus results in an addition of an exogenous sequence at the genomic locus.

In some embodiments, the targeted cell comprises a genomic DNA comprising the first and the second nucleic acid inserts together ranging from about 5 kb to about 500 kb. In some methods, the targeted cell comprises genomic DNA comprising the first and the second nucleic acid inserts together, which have a combined size ranging from about 5 kb to about 500 kb.

In another embodiment, integration of the first and/or the second nucleic acid inserts into the genomic locus results in a deletion of an endogenous sequence at the target genomic locus. In one embodiment, the deletion of the endogenous sequence at the target genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb.

In some methods, the cell is a human cell. In other methods, the cell is a non-human cell. In some methods, the cell is a pluripotent cell, a hematopoietic stem cell, a neuronal stem cell, or a fibroblast cell. Optionally, the pluripotent cell is an embryonic stem (ES) cell or an induced pluripotent stem (iPS) cell. In some methods, the cell is a mammalian cell. Optionally, the mammalian cell is a rodent cell. Optionally, the rodent cell is a mouse cell or a rat cell.

In one embodiment, the cell is a pluripotent cell. In another embodiment, the pluripotent cell is an embryonic stem (ES) cell. In some embodiments, the pluripotent cell is a hematopoietic stem cell or a neuronal stem cell. In another embodiment, the cell is an induced pluripotent stem (iPS) cell.

In one embodiment the target genomic locus is in the genome of the cell. In another embodiment, the target genomic locus is on extrachromosomal DNA within the cell.

In one embodiment, the cell is a fibroblast cell.

In some methods, the cell is a non-human cell. In other methods, the cell is from a human. In some embodiments the cell is a mammalian cell. In another embodiment, the mammalian cell is from a rodent. In some cases, the rodent is a mouse, a rat, or a hamster.

In some of the above methods, the overlapping nucleotide sequence facilitates recruitment of recombination machinery to the target genomic locus.

The invention also provides methods for producing an F0 generation non-human animal, comprising: (a) introducing a non-human ES cell into a non-human host embryo, wherein the non-human ES cell was produced by the above methods; and (b) gestating the non-human host embryo in a surrogate mother, wherein the surrogate mother produces the F0 generation non-human animal comprising the modification. Optionally, the non-human animal is a mouse or a rat.

In another aspect, a method is provided for enhancing homologous recombination at a target genomic locus in a cell by loading a recombination machinery onto a targeting vector, comprising introducing into the cell a first nucleic acid and a second nucleic acid, wherein the first and the second nucleic acids comprise an overlapping nucleotide sequence, and wherein the overlapping nucleotide sequence facilitates recruitment of the recombination machinery to the target genomic locus.

In one embodiment, the method enhances the homologous recombination of the first nucleic acid at the target genomic locus. Some such methods enhance the homologous recombination of the first nucleic acid at the target genomic locus compared to methods in which the first nucleic acid is introduced without the second nucleic acid. In one embodiment, the method enhances the homologous recombination of the second nucleic acid at the target genomic locus. Some such methods enhance the homologous recombination of the second nucleic acid at the target genomic locus compared to methods in which the second nucleic acid is introduced without the first nucleic acid. Some such methods enhance the homologous recombination of the first and the second nucleic acids at the target genomic locus. In one embodiment, the enhancement of the homologous recombination is at least 0.5-fold, 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold.

In one embodiment, the overlapping sequence of the first nucleic acid is homologous to the overlapping sequence of the second nucleic acid. In one embodiment, the overlapping sequence of the first nucleic acid is at least 70%, 75%, 80%, 85%, 90%, 95%, 96%, 97%, 98%, 99%, 99.5%, or 99.9% identical to the overlapping sequence of the second nucleic acid. In one embodiment, the overlapping sequence of the first nucleic acid is 100% identical to that overlapping sequence of the second nucleic acid.

In one embodiment, the overlapping sequence is from about 1 kb to about 70 kb. In one embodiment, the overlapping sequence is from about 1 kb to about 5 kb. In one embodiment, the overlapping sequence is from about 5 kb to about 10 kb. In one embodiment, the overlapping sequence is from about 10 kb to about 15 kb. In one embodiment, the overlapping sequence is from about 15 kb to about 20 kb. In one embodiment, the overlapping sequence is from about 20 kb to about 25 kb. In one embodiment, the overlapping sequence is from about 25 kb to about 30 kb. In one embodiment, the overlapping sequence is from about 30 kb to about 35 kb. In one embodiment, the overlapping sequence is from about 35 kb to about 40 kb. In one embodiment, the overlapping sequence is from about 40 kb to about 45 kb. In one embodiment, the overlapping sequence is from about 45 kb to about 50 kb. In one embodiment, the overlapping sequence is from about 50 kb to about 55 kb. In one embodiment, the overlapping sequence is from about 55 kb to about 60 kb. In one embodiment, the overlapping sequence is from about 60 kb to about 65 kb. In one embodiment, the overlapping sequence is from about 65 kb to about 70 kb.

In one embodiment, the overlapping sequence is at least 5 kb. In one embodiment, the overlapping sequence is at least 10 kb. In one embodiment the overlapping sequence is at least 15 kb. In one embodiment, the overlapping sequence is at least 20 kb. In one embodiment, the overlapping sequence is at least 25 kb. In one embodiment the overlapping sequence is at least 30 kb. In one embodiment, the overlapping sequence is at least 35 kb. In one embodiment the overlapping sequence is at least 40 kb. In one embodiment, the overlapping sequence is at least 45 kb. In one embodiment, the overlapping sequence is at least 50 kb. In one embodiment, the overlapping sequence is at least 55 kb. In one embodiment, the overlapping sequence is at least 60 kb. In one embodiment, the overlapping sequence is at least 65 kb. In one embodiment, the overlapping sequence is at least 70 kb.

In one embodiment, the first nucleic acid is a targeting vector comprising a first nucleic acid insert flanked by a first 5' homology arm and a first 3' homology arm, and the second nucleic acid does not comprise a nucleotide sequence that is homologous to the genomic locus except the overlapping sequence.

In one embodiment, the second nucleic acid is a second targeting vector comprising a second nucleic acid insert flanked by a second 5' homology arm and a second 3' homology arm, and the first nucleic acid does not comprise a nucleotide sequence that is homologous to the genomic locus except the overlapping sequence.

In one embodiment, the first nucleic acid is a first targeting vector comprising a first nucleic acid insert flanked by a first 5' homology arm and a first 3' homology arm, and the second nucleic acid is a second targeting vector comprising a second nucleic acid insert flanked by a second 5' homology arm and a second 3' homology arm. In one embodiment, the first nucleic acid insert and the second nucleic acid insert are overlapping fragments of a contiguous nucleic acid.

In one embodiment, the targeting vector is from about 1 kb to about 2 kb. In one embodiment, the targeting vector is from about 2 kb to about 5 kb. In one embodiment, the targeting vector is from about 5 kb to about 10 kb.

In one embodiment, the targeting vector is a large targeting vector (LTVEC). In some methods, the targeting vector is an LTVEC ranging from about 10 kb to about 200 kb. In some methods, the first targeting vector is a first LTVEC and/or the second targeting vector is a second LTVEC. In some methods, the first targeting vector is a first LTVEC ranging from about 10 kb to about 200 kb, and/or the second targeting vector is a second LTVEC ranging from about 10 kb to about 200 kb. In one embodiment, the LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. Optionally, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. Optionally, the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb. In some methods, the first LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb, and the second LTVEC is from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, or from about 150 kb to about 200 kb.

In one embodiment, the sum total of the 5' and the 3' homology arms of the LTVEC is from 10 kb to about 200 kb. In some methods, the sum total of the 5' and the 3' homology arms of the first LTVEC is from 10 kb to about 200 kb. In some methods, the sum total of the 5' and the 3' homology arms of the second LTVEC is from 10 kb to about 200 kb. In some methods, the sum total of the 5' and the 3' homology arms of the first LTVEC is from 10 kb to about 200 kb, and the sum total of the 5' and the 3' homology arms of the second LTVEC is from 10 kb to about 200 kb.

In one embodiment, the overlapping sequence is located at the 3' end of the first nucleic acid and the 5' end of the second nucleic acid sequence. In one embodiment, the overlapping sequence is located at the 5' end of the first nucleic acid sequence and the 3' end of the second nucleic acid sequence.

In one embodiment, the first nucleic acid insert and/or the second nucleic acid insert are from a different species. In another embodiment, the first nucleic acid insert and/or the second nucleic acid insert are human nucleic acids. In some methods, the first nucleic acid insert, the second nucleic acid insert, or both are from a species different from the species of the cell. In some methods, the first nucleic acid insert, the second nucleic acid insert, or both are human nucleic acids.

In some methods, integration of the first nucleic acid insert, the second nucleic acid insert, or both into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof. In some methods, integration of one or more of the first, the second and the third nucleic acid inserts into the target genomic locus results in one or more of: (a) an addition of an exogenous sequence at the target genomic locus; (b) a deletion of an endogenous sequence at the target genomic locus; or (c) a knock-in, a knockout, a point mutation, a domain swap, an exon swap, an intron swap, a regulatory sequence swap, a gene swap, or a combination thereof.

In one embodiment, integration of the first and/or the second inserts into the genomic locus results in an addition of an exogenous sequence at the genomic locus.

In some embodiments, the targeted cell comprises a genomic DNA comprising the first and the second nucleic acid inserts together ranging from about 5 kb to about 500 kb. In some methods, the targeted cell comprises genomic DNA comprising the first nucleic acid insert and the second nucleic acid insert together, which have a combined size ranging from about 5 kb to about 500 kb.

In another embodiment, integration of the first and/or the second nucleic acid inserts into the genomic locus results in a deletion of an endogenous sequence at the target genomic locus. In one embodiment, the deletion of the endogenous sequence at the target genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb.

In some methods, the cell is a human cell. In other methods, the cell is a non-human cell. In some methods, the cell is a pluripotent cell, a hematopoietic stem cell, a neuronal stem cell, or a fibroblast cell. Optionally, the pluripotent cell is an embryonic stem (ES) cell or an induced pluripotent stem (iPS) cell. In some methods, the cell is a mammalian cell. Optionally, the mammalian cell is a rodent cell. Optionally, the rodent cell is a mouse cell or a rat cell.

In one embodiment, the cell is a pluripotent cell. In another embodiment, the pluripotent cell is an embryonic stem (ES) cell. In some embodiments, the pluripotent cell is a hematopoietic stem cell or a neuronal stem cell. In another embodiment, the cell is an induced pluripotent stem (iPS) cell.

In one embodiment the target genomic locus is in the genome of the cell. In another embodiment, the target genomic locus is on extrachromosomal DNA within the cell.

In one embodiment, the cell is a fibroblast cell.

In one embodiment, the cell is a non-human cell. In other embodiment, the cell is from a human. In other embodiment, the cell is a mammalian cell. In another embodiment, the mammalian cell is from a rodent. In another embodiment, the rodent is a mouse, a rat, or a hamster.

The invention also provides methods for producing an F0 generation non-human animal, comprising: (a) introducing a non-human ES cell into a non-human host embryo, wherein the non-human ES cell was produced by the above methods; and (b) gestating the non-human host embryo in a surrogate mother, wherein the surrogate mother produces the F0 generation non-human animal comprising the modification. Optionally, the non-human animal is a mouse or a rat.

DEFINITIONS

Figure 1:
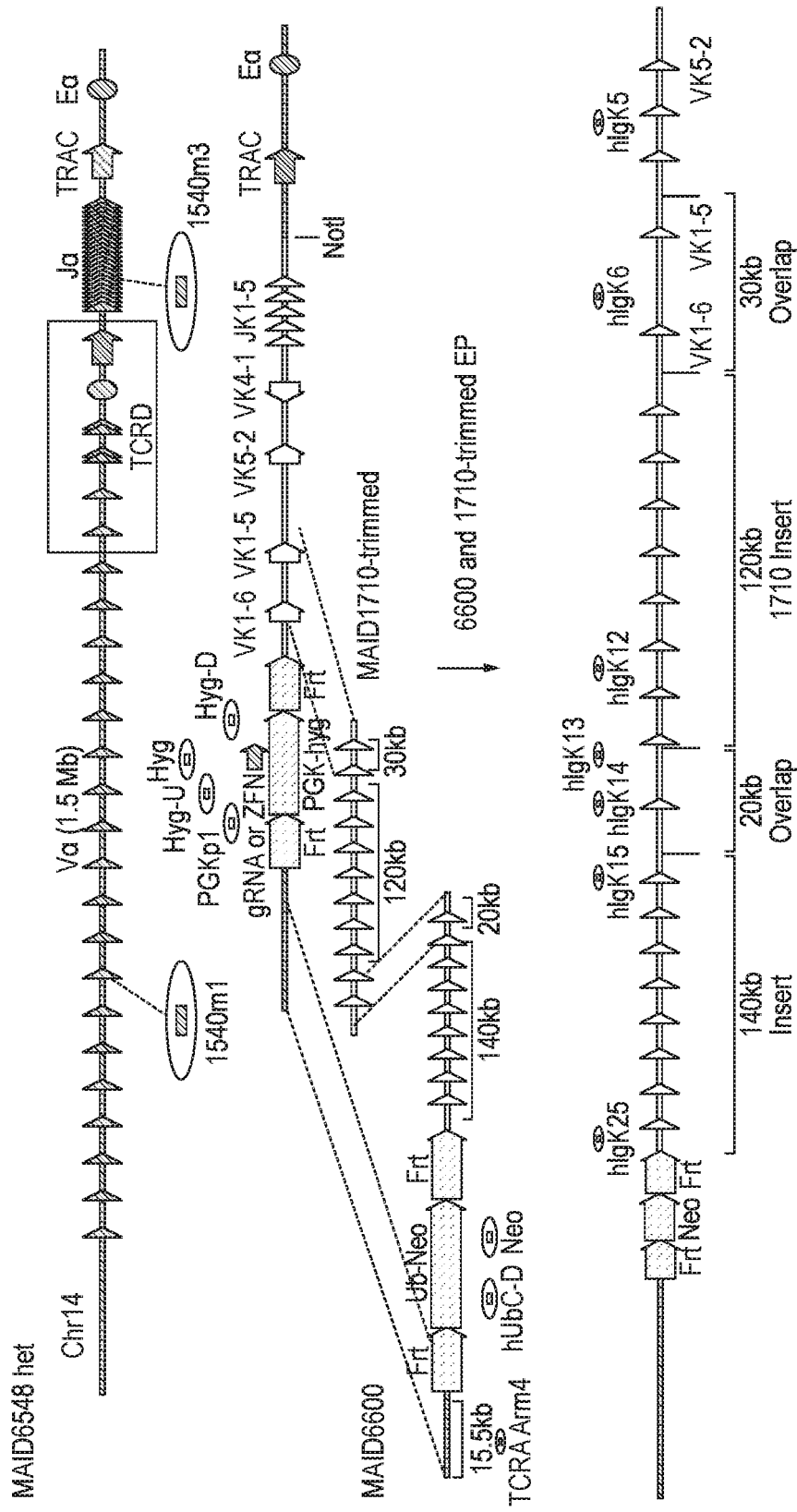
FIG. 1 provides a schematic for a genomic double targeting event in which a cell having a heterozygous modification of the TCR alpha locus on mouse chromosome 14 comprising a hygromycin selection cassette is targeted. The hygromycin selection cassette is cleaved by a zinc finger nuclease (ZFN) or by a CRISPR/Cas complex and is targeted with two large targeting vectors comprising a neomycin selection cassette and over 280 kb of human immunoglobulin kappa chain variable gene segments. The large targeting vectors each comprise an overlapping sequence of approximately 20 kb, which allows for homologous recombination between the large targeting vectors. The targeting event precisely inserted the human immunoglobulin kappa chain variable gene segments from both targeting vectors in a single targeting step. The locations of the various probes used to confirm the targeting event are shown as encircled rectangles. Mouse sequence is represented by upward, diagonal hatching, human sequence is represented by no hatching, and recombination sites and selection cassettes are represented by downward, dashed, diagonal hatching. The schematic is not to scale and does not, for example, reflect the actual number of variable gene segments.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

A target genomic locus means a region of a genome to be modified by a targeted modification with a targeting vector. The region can be defined as the region within the outer borders of segments of genomic DNA corresponding to homology arms within the targeting vector. A target genomic locus can include any or all of a gene or grouping of genes, one or more introns, one or more exons, one or more regulatory sequences, and the like.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292. Computer algorithms for codon optimization of a particular sequence for expression in a particular host are also available (see, e.g., Gene Forge).

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors.

The term "pluripotent cell" or "pluripotent stem cell" includes an undifferentiated cell that possesses the ability to develop into more than one differentiated cell type. Such pluripotent cells can be, for example, a mammalian embryonic stem (ES cell) cell or a mammalian induced pluripotent stem cell (iPS cell).

The term "embryonic stem cell" or "ES cell" includes an embryo-derived totipotent or pluripotent cell that is capable of undifferentiated proliferation in vitro, and is capable of contributing to any tissue of the developing embryo upon introduction into an embryo.

The term "induced pluripotent stem cell" or "iPS cell" includes a pluripotent stem cell that can be derived directly from a differentiated adult cell. Human iPS cells can be generated by introducing specific sets of reprogramming factors into a non-pluripotent cell which can include, for example, Oct3/4, Sox family transcription factors (e.g., Sox1, Sox2, Sox3, Sox15), Myc family transcription factors (e.g., c-Myc, 1-Myc, n-Myc), Krüppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, for example, Takahashi and Yamanaka (Cell (2006) Vol. 126(4), pp. 663-676).

The term "germline" in reference to an immunoglobulin nucleic acid sequence includes a nucleic acid sequence that can be passed to progeny.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989).

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, nuclease agents, Cas proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

A "homologous" sequence includes a nucleic acid sequence that is either identical or substantially similar to a known reference sequence, such that it is at least 70%, at least 75%, at least 80%, at least 85%, at least 90%, at least 95%, at least 96%, at least 97%, at least 98%, at least 99%, or 100% identical to the known reference sequence. An "orthologous" sequence includes a nucleic acid sequence from one species that is functionally equivalent to a known reference sequence in another species.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas protein" or "at least one Cas protein" can include a plurality of Cas proteins, including mixtures thereof.

DETAILED DESCRIPTION

I. Modification of Genomic Loci Using Multiple Targeting Vectors

Methods and compositions are provided for modifying a target genomic locus within a cell. Such methods employ multiple large targeting vectors (LTVECs) that are capable of recombining with one another to form a single contiguous nucleic acid segment. Such methods can utilize 1, 2, 3, 4, 5, 6, or more LTVECs in a single targeting step. Methods and compositions are also provided for enhancing homologous recombination at a target genomic locus in a cell. Such methods employ two or more nucleic acids comprising one or more overlapping sequences. Any of the methods disclosed herein can occur in vitro, ex vivo, or in vivo.

A. Double-Targeting

Methods and compositions for modifying a target genomic locus within a cell via a double targeting method are provided. The methods and compositions employ two large targeting vectors (LTVECs) (i.e., a first LTVEC and a second LTVEC) that are capable of recombining with one another to form a single contiguous nucleic acid segment. The first LTVEC comprises a first nucleic acid insert and the second LTVEC comprises a second nucleic acid insert. The nucleic acid inserts are flanked by 5' and 3' homology arms. The first nucleic acid insert and its 3' homology arm and the second nucleic acid insert and its 5' homology arm can be overlapping fragments of the same contiguous nucleic acid. The 3' homology arm of the first LTVEC and the 5' homology arm of the second LTVEC overlap (i.e., are complementary to one another) and the first and second inserts flank the overlapping homology arms. Such methods involve three recombination events that can occur in any order: (1) recombination between the 3' homology arm of the first LTVEC and the 5' homology arm of the second LTVEC; (2) recombination between the 5' homology arm of the first LTVEC and the corresponding segment in the target locus; and (3) recombination between the 3' homology arm of the second LTVEC and the corresponding segment in the target locus. This three-way recombination reconstructs the contiguous nucleic acid in the target locus with the overlapping sequence of the homology arms positioned in between the first and the second nucleic acid inserts.

Each of the LTVECs also comprises either a 5' or a 3' homology arm that is homologous to a region of DNA within or near a target genomic locus which allows recombination and integration of the single contiguous nucleic acid segment. Thus, by means of a three-way recombination event, a large nucleic acid modification (i.e., deletion, insertion, and/or replacement) can be made at a target locus in a single targeting step.

The three recombination events can occur in any order. In one embodiment, the recombination event between the overlapping sequences of the two LTVECs occurs before the homologous recombination with the target locus. In another embodiment, the recombination with the target locus occurs before the recombination between the two LTVECs. In yet another embodiment, the three recombination events can occur simultaneously.

In one embodiment, a method for modifying a target genomic locus in a cell is provided. Such a method comprises introducing a first large targeting vector (LTVEC) comprising a first nucleic acid insert flanked by a first 5' homology arm and a first 3' homology arm, and a second LTVEC comprising a second nucleic acid insert flanked by a second 5' homology arm and a second 3' homology arm, wherein the first 3' homology arm of the first LTVEC has an overlapping sequence homologous to the second 5' homology arm of the second LTVEC, and the first 5' homology arm of the first LTVEC and the second 3' homology arm of the second LTVEC are homologous to corresponding genomic segments within the target genomic locus; wherein the target genomic locus is modified by integration of the first and second nucleic acid inserts between the corresponding genomic segments. The method further comprises selecting a targeted cell comprising the first nucleic acid insert and the second nucleic acid insert integrated in the target genomic locus.

B. Triple Targeting

Methods and compositions for modifying a target genomic locus within a cell via triple targeting methods are also provided. The methods and compositions employ three large targeting vectors (LTVECs) (i.e., a first LTVEC, a second LTVEC and a third LTVEC) that are capable of recombining with one another to form a single contiguous nucleic acid segment. The first LTVEC comprises a first nucleic acid insert, the second LTVEC comprises a second nucleic acid insert, and the third LTVEC comprises a third nucleic acid insert. The nucleic acid inserts are flanked by 5' and 3' homology arms. The first nucleic acid insert and its 3' homology arm and the second nucleic acid insert and its 5' homology arm can be overlapping fragments of the same contiguous nucleic acid. The second nucleic acid insert and its 3' homology arm and the third nucleic acid insert and its 5' homology arm can be overlapping fragments of the same contiguous nucleic acid. The 3' homology arm of the first LTVEC and the 5' homology arm of the second LTVEC overlap (i.e., are complementary to one another) and the first and second inserts flank the overlapping homology arms. The 3' homology arm of the second LTVEC and the 5' homology arm of the third LTVEC overlap (i.e., are complementary to one another) and the second and third inserts flank the overlapping homology arms.

Such methods involve four recombination events that can occur in any order: (1) recombination between the 3' homology arm of the first LTVEC and the 5' homology arm of the second LTVEC; (2) recombination between the 3' homology arm of the second LTVEC and the 5' homology arm of the third LTVEC; (3) recombination between the 5' homology arm of the first LTVEC and the corresponding segment in the target locus; and (4) recombination between the 3' homology arm of the third LTVEC and the corresponding segment in the target locus. This four-way recombination reconstructs the contiguous nucleic acid in the target locus with the overlapping sequence of the homology arms positioned in between the first and the second nucleic acid inserts and in between the second and third nucleic acid inserts.

The first and the third LTVECs also comprise either a 5' or a 3' homology arm that is homologous to a region of DNA within or near a target genomic locus, which allows recombination and integration of the single contiguous nucleic acid segment. Thus, by means of a four-way recombination event, a large nucleic acid modification (i.e., deletion, insertion, and/or replacement) can be made at a target locus in a single targeting step.

The four recombination events can occur in any order. In one embodiment, the recombination event between the overlapping sequences of the three LTVECs occurs before the homologous recombination with the target locus. In another embodiment, the recombination with the target locus occurs before the recombination between the three LTVECs. In yet another embodiment, the four recombination events can occur simultaneously.

In one embodiment, a method for modifying a target genomic locus in a cell is provided. Such a method comprises introducing a first large targeting vector (LTVEC) comprising a first nucleic acid insert flanked by a first 5' homology arm and a first 3' homology arm, a second LTVEC comprising a second nucleic acid insert flanked by a second 5' homology arm and a second 3' homology arm, and a third LTVEC comprising a third nucleic acid insert flanked by a third 5' homology arm and a third 3' homology arm, wherein the first 3' homology arm of the first LTVEC has an overlapping sequence homologous to the second 5' homology arm of the second LTVEC, the second 3' homology arm of the second LTVEC has an overlapping sequence homologous to the third 5' homology arm of the third LTVEC, and the first 5' homology arm of the first LTVEC and the third 3' homology arm of the third LTVEC are homologous to corresponding genomic segments within the target genomic locus; wherein the target genomic locus is modified by integration of the first, the second, and the third nucleic acid inserts between the corresponding genomic segments. The method further comprises selecting a targeted cell comprising the first nucleic acid insert, the second nucleic acid insert, and the third nucleic acid insert integrated in the target genomic locus.

C. Targeting with Multiple LTVECs

The targeting methods provided herein for creating a genetic modification in a single targeting step provide new possibilities and enhanced efficiencies for targeted gene modifications beyond those achieved with a single LTVEC targeting method. Targeting with two, three, or more LTVECs that are capable of recombining with each other allows for the modification of a larger segment of DNA. The recombination events can occur in any order. For example, the recombination event between the overlapping sequences of the LTVECs can occur before the homologous recombination with the target locus. Alternatively, the recombination with the target locus can occur before the recombination among the LTVECs or the recombination events can occur simultaneously.

The targeting methods described herein provide several advantages over existing single LTVEC targeting methods including an increased targeting efficiency, an increase in the achievable size of the genetic modification, and a reduction in the number of targeting steps needed to obtain large genomic modifications, which saves time and maintains the pluripotency of modified embryonic stem cells. This is of particular importance for large genomic modifications as the methods allow for the modification of the genomic locus with a combination of nucleic acid inserts from two, three, or more LTVECs in a single step. Thus, such modifications can allow for very large (e.g., >50 kb) deletions, replacements and insertions within the targeted genomic locus.

For example, the time required to use three LTVECs in a sequential manner to modify a target genomic locus and screen for and confirm the targeted modification is approximately nine months, whereas the same modification can be made and confirmed with three LTVECs simultaneously in only about four months.

Sequential modifications also create a higher risk of loss of pluripotency and germline transmission potential when pluripotent cells such as embryonic stem cells are modified. As the number of passages in culture increases and the number of electroporations increases, chromosomal and karyotypic abnormalities accumulate and can cause a loss of germline competence. See, e.g., Buehr et al. (2008) *Cell* 135:1287-1298; Li et al. (2008) *Cell* 135(7): 1299-1310; and Liu et al. (1997) *Dev. Dyn.* 209:85-91, each of which is herein incorporated by reference in its entirety for all purposes. Targeting using multiple LTVECs simultaneously instead of sequentially reduces the number of passages and number of electroporations and thereby increases the ability to perform genetic manipulations in pluripotent cells such as embryonic stem cells while retaining their germline competency.

In particular embodiments, the genetic modification comprises a modification of one or more endogenous nucleic acids, a substitution of one or more endogenous nucleic acids, a replacement of an endogenous nucleic acid with a heterologous nucleic acid, a knockout, or a knock-in. In specific examples, the genetic modification is introduced by introducing at least two large targeting vectors (LTVECs) into a cell. In another example, the genetic modification is introduced by introducing at least three large targeting vectors (LTVECs) into a cell. In such examples, the LTVECs can comprise DNA to be inserted into the target genomic locus of the cell.

In some embodiments, the methods for modifying a target genomic locus comprise introducing a genetic modification into mammalian cells. Likewise, the invention provides mammalian cells that comprise a genetic modification.

Various methods for making targeted genetic modifications in cells can be used. For example, as described above, the targeted genetic modification employs a system that will generate a targeted genetic modification via a homologous recombination event. In other instances, a cell can be modified using nuclease agents that generate a single or double strand break at a targeted genomic locus. The single or double-strand break is then repaired by the non-homologous end joining pathway (NHEJ). Exemplary methods for generating such targeted genetic modifications are discussed in detail elsewhere herein, including, for example, the use of large targeting vectors. See also Wang et al. (2013) Cell 153:910-918, Mandalos et al. (2012) PLOS ONE 7:e45768: 1-9, and Wang et al. (2013) Nat Biotechnol. 31:530-532, each of which is herein incorporated by reference.

Targeted gene modification by homologous recombination between a targeting vector and a target locus can be very inefficient, especially in cell types other than rodent embryonic stem cells. Use of a targeting vector in combination with a nuclease-directed double-strand DNA break at the target locus can greatly enhance targeting efficiency for modifications, such as deletions or insertions. Similarly, use of a targeting vector in combination with a nuclease-directed single-strand DNA break at the target locus can greatly enhance targeting efficiency for modifications.

In some embodiments, the LTVECs can be employed in combination with nuclease agents that make a single or double-strand break within a target genomic locus. Such a method further comprises introducing a nuclease agent into a cell. In one embodiment, the nuclease agent is a zinc-finger nuclease (ZFN). In another embodiment, the nuclease agent is a Clustered Regularly Interspersed Short Palindromic Repeats (CRISPR)/CRISPR-associated (Cas) system.

In one embodiment, a method is provided for modifying a target genomic locus in a cell by utilizing multiple LTVECs. Such a method comprises (a) introducing into a cell a nuclease agent that makes a single or double-strand break within a target genomic locus; (b) introducing a first large targeting vector (LTVEC) comprising a first nucleic acid insert flanked by a first 5' homology arm and a first 3' homology arm, and a second LTVEC comprising a second nucleic acid insert flanked by a second 5' homology arm and a second 3' homology arm, wherein the first 5' homology arm of the first LTVEC and the second 3' homology arm of the second LTVEC are homologous to corresponding genomic segments within the target genomic locus and the first 3' homology arm of the first LTVEC and the second 5' arm of the second LTVEC are homologous to each other or respectively to further 5' and 3' homology arms of one or more further LTVECs, each comprising a further nucleic acid insert flanked by a further 5' homology arm and a further 3' homology arm; wherein the target genomic locus is modified by integration of the first nucleic acid insert, the one or more further nucleic acid inserts of the one or more further LTVECs (if present), and the second nucleic acid insert between the corresponding genomic segments; and (c) selecting a targeted cell comprising the first nucleic acid insert, the one or more further nucleic acid inserts (if present), and the second nucleic acid insert integrated in the target genomic locus. In such methods, the further LTVECs are one or more other LTVECs that, when present, are inserted between the first and the second LTVEC.

In one embodiment, a double targeting method is provided for modifying a target genomic locus in a cell, the method comprising: (a) introducing into a cell a nuclease agent that makes a single or double-strand break within a target genomic locus; (b) introducing a first large targeting vector (LTVEC) comprising a first nucleic acid insert flanked by a first 5' homology arm and a first 3' homology arm, and a second LTVEC comprising a second nucleic acid insert flanked by a second 5' homology arm and a second 3' homology arm, wherein the first 3' homology arm of the first LTVEC has an overlapping sequence homologous to the second 5' homology arm of the second LTVEC and the first 5' homology arm of the first LTVEC and the second 3' homology arm of the second LTVEC are homologous to corresponding genomic segments within the target genomic locus; wherein the target genomic locus is modified by integration of the first and second nucleic acid inserts between the corresponding genomic segments; and (c) selecting a targeted cell comprising the first nucleic acid insert and the second nucleic acid insert integrated in the target genomic locus. In such methods, the first nucleic insert and the first 3' homology arm and the second nucleic acid insert and second 5' homology arm are overlapping fragments of a contiguous nucleic acid, which is reformed by integration of the first nucleic acid insert and the second nucleic acid insert into the target genomic locus.

In one embodiment a triple targeting method is provided for modifying a target genomic locus in a cell, the method comprising: (a) introducing into a cell a nuclease agent that makes a single or double-strand break within a target genomic locus; (b) introducing a first large targeting vector (LTVEC) comprising a first nucleic acid insert flanked by a first 5' homology arm and a first 3' homology arm, a second LTVEC comprising a second nucleic acid insert flanked by a second 5' homology arm and a second 3' homology arm, and a third LTVEC comprising a third nucleic acid insert flanked by a third 5' homology arm and a third 3' homology arm, wherein the first 3' homology arm of the first LTVEC has an overlapping sequence homologous to the second 5' homology arm of the second LTVEC, the second 3' homology arm of the second LTVEC has an overlapping sequence homologous to the third 5' homology arm of the third LTVEC, and the first 5' homology arm of the first LTVEC and the third 3' homology arm of the third LTVEC are homologous to corresponding genomic segments within the target genomic locus; wherein the target genomic locus is modified by integration of the first, the second, and the third nucleic acid inserts between the corresponding genomic segments; and (c) selecting a targeted cell comprising the first nucleic acid insert, the second nucleic acid insert, and the third nucleic acid insert integrated in the target genomic locus. In such triple targeting methods, the first nucleic insert and the first 3' homology arm and the second nucleic acid insert and second 5' homology arm are overlapping fragments of a contiguous nucleic acid, and the second nucleic insert and the second 3' homology arm and the third nucleic acid insert and third 5' homology arm are overlapping fragments of a contiguous nucleic acid, which is reformed by integration of the first nucleic acid insert, the second nucleic acid insert and the third nucleic acid insert into the target genomic locus.

In some cases, the two, three, or more LTVECs can be introduced simultaneously. Alternatively, the two, three, or more LTVECs can be introduced sequentially or can be introduced at different times.

The various components of the targeting system may include, for example, targeting vectors, nuclease agents, a target genomic locus, nucleic acid inserts, polynucleotides of interest, and/or other components, each of which is described in detail elsewhere herein.

D. Targeting with Multiple Overlapping Nucleic Acids

The targeting methods provided herein for creating a genetic modification in a single targeting step provide new possibilities and enhanced efficiencies for targeted gene modifications beyond those achieved with a single nucleic acid. Targeting with two, three, or more nucleic acids that are capable of recombining with each other allows for the modification of a larger segment of DNA and can provide enhanced targeting efficiencies over single nucleic acids alone, even in the absence of nuclease agents. Such methods without nuclease agents can be advantageous over those employing nuclease agents because the screening required for methods using nucleases is more complicated and time-consuming, involving the additional screening steps of confirming cleavage and checking for off-targeted effects. Nucleic acids (e.g., LTVECs) with overlapping regions of sufficient length can enhance homologous recombination at a target genomic locus even in the absence of a targeted nuclease. As an example, use of two nucleic acids with an overlapping region of sufficient length can enhance homologous recombination at a target genomic locus compared to use of a single nucleic acid. Although an understanding of mechanism is not required for practice, it is believed that homologous recombination is enhanced under such circumstances by the loading of recombination machinery (e.g., ExoI, Rad51, BRCA2, and so forth) onto the nucleic acids (e.g., LTVECs), thereby facilitating recruitment of the recombination machinery to the target locus.

Methods are provided herein for modifying a target genomic locus or enhancing homologous recombination at a target genomic locus in a cell, comprising introducing into the cell first and second nucleic acids, wherein the first and the second nucleic acids comprise an overlapping sequence. The first and second nucleic acids can be, for example, linear nucleic acids. Such methods can also comprise introducing into the cell three or more nucleic acids that are capable of recombining with each other. For example, the first and second nucleic acids can have a first overlapping sequence, and the second and third nucleic acids can have a second overlapping sequence. In some methods, the target genomic locus is modified, or homologous recombination at the target genomic locus is enhanced, without the assistance of a nuclease. In other methods, the target genomic locus is modified, or homologous recombination at the target genomic locus is enhanced, with the assistance of a nuclease that makes a single or double strand break at or near the target genomic locus, such as a zinc finger nuclease, a TALEN, a meganuclease, or Cas9 and a guide RNA.

The method can enhance homologous recombination of the first nucleic acid at the target genomic locus, can enhance homologous recombination of the second nucleic acid at the target genomic locus, or can enhance homologous recombination of both the first and the second nucleic acids at the target genomic locus. As an example, the homologous recombination of the first nucleic acid at the target genomic locus can be enhanced compared to methods in which the first nucleic acid is introduced without the second nucleic acid. Likewise, the homologous recombination of the second nucleic acid at the target genomic locus can be enhanced compared to methods in which the second nucleic acid is introduced without the first nucleic acid. The enhancement of the homologous recombination can be, for example, at least 1.5-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold. In some methods, the enhancement without a nuclease can be comparable to the enhancement with a nuclease. For example, the fold change in enhancement with a nuclease can be 0.5-fold, 0.6-fold, 0.7-fold, 0.8-fold, 0.9-fold, 1.0-fold, 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, or 10-fold when compared to enhancement without a nuclease. In some cases, the enhancement without a nuclease can be the same as or greater than the enhancement with a nuclease.

The overlapping sequence of the first nucleic acid can be homologous to the overlapping sequence of the second nucleic acid. For example, the overlapping sequence of the first nucleic acid can be at least 70%, 75%, 80%, 85%, 90%, 95%, 96%, 97%, 98%, 99%, 99.5%, or 99.9% identical to the overlapping sequence of the second nucleic acid. Alternatively, the overlapping sequence of the first nucleic acid can be 100% identical to the overlapping sequence of the second nucleic acid.

The overlapping sequence can be, for example, from about 1 kb to about 70 kb or more. For example, the overlapping sequence can be from about 1 kb to about 5 kb, from about 5 kb to about 10 kb, from about 10 kb to about 15 kb, from about 15 kb to about 20 kb, from about 20 kb to about 25 kb, from about 25 kb to about 30 kb, from about 30 kb to about 35 kb, from about 35 kb to about 40 kb, from about 40 kb to about 45 kb, from about 45 kb to about 50 kb, from about 50 kb to about 55 kb, from about 55 kb to about 60 kb, from about 60 kb to about 65 kb, from about 65 kb to about 70 kb, from about 70 kb to about 80 kb, from about 80 kb to about 90 kb, from about 90 kb to about 100 kb, from about 100 kb to about 120 kb, from about 120 kb to about 140 kb, from about 140 kb to about 160 kb, from about 160 kb to about 180 kb, from about 180 kb to about 200 kb, from about 200 kb to about 220 kb, from about 220 kb to about 240 kb, from about 240 kb to about 260 kb, from about 260 kb to about 280 kb, or about 280 kb to about 300 kb. As an example, the overlapping sequence can be from about 20 kb to about 60 kb. Alternatively, the overlapping sequence can be at least 1 kb, at least 5 kb, at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 80 kb, at least 90 kb, at least 100 kb, at least 120 kb, at least 140 kb, at least 160 kb, at least 180 kb, at least 200 kb, at least 220 kb, at least 240 kb, at least 260 kb, at least 280 kb, or at least 300 kb.

The overlapping sequence can be located anywhere within the first and second nucleic acids. For example, the overlapping sequence can be located at the 3' end of the first nucleic acid and the 5' end of the second nucleic acid. Alternatively, the overlapping sequence can be located at the 5' end of the first nucleic acid and at the 3' end of the second nucleic acid.

In some methods, the first nucleic acid is a targeting vector comprising a first nucleic acid insert flanked by a first 5' homology arm and a first 3' homology arm. The second nucleic acid can be any nucleic acid comprising an overlapping sequence, such as a plasmid, a targeting vector, or a large targeting vector. In some methods, the second nucleic acid does not comprise a nucleotide sequence that is homologous to the target genomic locus except for the overlapping sequence. For example, the second nucleic acid can consist essentially of or consist of the overlapping sequence.

In some methods, the first nucleic acid is a targeting vector comprising a first nucleic acid insert flanked by a first 5' homology arm and a first 3' homology arm, and the second nucleic acid is a second targeting vector comprising a second nucleic acid insert flanked by a second 5' homology arm and a second 3' homology arm.

The first targeting vector can be of any size. Likewise, the second targeting vector can be of any size. For example, the first and/or second targeting vectors can be from about 1 kb to about 2 kb, from about 2 kb to about 5 kb, or from about 5 kb to about 10 kb. The first targeting vector can also be a large targeting vector (LTVEC). Likewise, the second targeting vector can be an LTVEC. Exemplary sizes of LTVECs are disclosed elsewhere herein. For example, the first and/or second LTVECs can be from about 20 kb to about 40 kb, from about 40 kb to about 60 kb, from about 60 kb to about 80 kb, from about 80 kb to about 100 kb, from about 100 kb to about 120 kb, from about 120 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 450 kb, from about 450 kb to about 500 kb, from about 500 kb to about 550 kb, from about 550 kb to about 600 kb, about 600 kb to about 650 kb, from about 650 kb to about 700 kb, from about 700 kb to about 750 kb, of from about 750 kb to about 800 kb.

In some methods, the first nucleic acid is an LTVEC, and the second nucleic acid is a smaller nucleic acid comprising an overlapping sequence, such as a plasmid or a targeting vector. In some methods, the second nucleic acid does not comprise a nucleotide sequence that is homologous to the target genomic locus except for the overlapping sequence. For example, the second nucleic acid can consist essentially of or consist of the overlapping sequence.

In some methods, the first nucleic acid insert and the second nucleic acid insert are overlapping fragments of a contiguous nucleic acid. In some methods, the first and/or second nucleic acid inserts can be from a different species than the species of the cell. For example, the first and/or second nucleic acid inserts can be human nucleic acids.

The methods can result in integration of the first and/or second nucleic acid inserts into the target genomic locus. The integration can result in addition of a sequence at the target genomic locus, deletion of a sequence at the target genomic locus, or replacement of a sequence at the target genomic locus. For example, the integration can result in addition of an exogenous sequence at the target genomic locus, deletion of an endogenous sequence at the target genomic locus, or replacement of an endogenous sequence with an exogenous sequence at the target genomic locus. The first nucleic acid insert, the second nucleic acid insert, or the combination of the first and second nucleic acid inserts that are inserted at the target genomic locus can be, for example, from about 5 kb to about 500 kb. Other exemplary nucleic acid insert and insertion sizes are disclosed elsewhere herein. The deletion at the target genomic locus can be, for example, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, or from about 700 kb to about 800 kb. Other exemplary deletion sizes are disclosed elsewhere herein.

The targeted cell can be any of the cell types provided herein, and the target genomic locus can be any DNA within the cell. For example, the target genomic locus can be in the genome of the cell, or it can be on extrachromosomal DNA within the cell.

II. Nucleic Acid Inserts and Targeting Vectors

A. Nucleic Acid Insert

One or more nucleic acid inserts can be employed in the methods disclosed herein, and they can be introduced into a cell via separate targeting vectors or on the same targeting vector. Nucleic acid inserts include segments of DNA to be integrated at genomic target loci. Integration of a nucleic acid insert at a target locus can result in addition of a nucleic acid sequence of interest to the target locus, deletion of a nucleic acid sequence of interest at the target locus, and/or replacement of a nucleic acid sequence of interest at the target locus.

The methods provide for the modification of a genomic locus with nucleic acid inserts that are larger in size than can be achieved using conventional single targeting techniques (i.e., a single LTVEC). In such methods, the nucleic acid inserts are included on two, three, or more LTVECs. The LTVECs are designed such that they are capable of recombining with each other to form a single large segment of DNA comprising the combined nucleic acid inserts from the two, three, or more LTVECs.

In such methods, the nucleic acid inserts are flanked by 5' and 3' homology arms. The 3' homology arm flanking the first nucleic acid insert and the 5' homology arm flanking the second nucleic acid insert are overlapping fragments of the same contiguous nucleic acid which is then reformed by recombination between the overlapping fragments of the homology arms. In such methods, the recombination between the two LTVECs results in a contiguous nucleic acid insert with the overlapping sequence of the homology arms positioned in between the first and the second nucleic acid inserts. Triple targeting methods involve an additional recombination between the second LTVEC and the third LTVEC in which the 3' homology arm flanking the second nucleic acid insert and the 5' homology arm flanking the third nucleic acid insert are overlapping fragments of the same contiguous nucleic acid which is then reformed by recombination between the overlapping fragments of the homology arms. In such triple targeting methods, the recombination between the three LTVECs results in a contiguous nucleic acid insert with the overlapping sequence of the homology arms positioned in between the first, the second and the third nucleic acid inserts. In one embodiment, the overlapping sequence of the homology arms comprises a portion of the nucleic acid insert.

As such, these methods allow for a modification of a genomic locus with nucleic acid inserts from two, three or more LTVECs in a single targeting step, thus effectively increasing the total size of the nucleic acid insert while at the same time reducing the number of targeting steps.

The nucleic acid insert or the corresponding nucleic acid at the target locus being replaced can be a coding region, an intron, an exon, an untranslated region, a regulatory region, a promoter, an enhancer, or any combination thereof. Moreover, the size of the nucleic acid insert (i.e., the combined nucleic acid inserts from the two, three or more LTVECs) or the corresponding nucleic acid at the target locus being replaced can be of any desired length, including, for example, between 10-100 nucleotides in length, 100-500 nucleotides in length, 500 nucleotides-1 kb in length, 1 kb to 1.5 kb in length, 1.5 kb to 2 kb in length, 2 kb to 2.5 kb in length, 2.5 kb to 3 kb in length, 3 kb to 5 kb in length, 5 kb to 8 kb in length, 8 kb to 10 kb in length or more. In other cases, the length can be from about 50 kb to about 700 kb, from about 50 kb to about 500 kb, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb, from about 275 kb to about 300 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 450 kb, from about 450 kb to about 500 kb, from about 500 kb to about 550 kb, from about 550 kb to about 600 kb, from about 600 kb to about 650 kb, from about 650 kb to about 700 kb, from about 700 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, or from about 2.8 Mb to about 3 Mb. Alternatively, the combined nucleic acid inserts from the two, three, or more LTVECs or the corresponding nucleic acid at the target locus being replaced can be from about 3 Mb to about 4 Mb, from about 4 Mb to about 5 Mb, from about 5 Mb to about 6 Mb, from about 6 Mb to about 7 Mb, from about 7 Mb to about 8 Mb, from about 8 Mb to about 9 Mb, or from about 9 Mb to about 10 Mb. In yet other cases, the length can be at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater. For example, the combined nucleic acid inserts from the two, three or more LTVECs) or the corresponding nucleic acid at the target locus being replaced can be at least 20 kb, at least 40 kb, at least 60 kb, at least 80 kb, at least 100 kb, at least 150 kb, at least 200 kb, at least 250 kb, at least 300 kb, at least 350 kb, at least 400 kb, at least 450 kb, at least 500 kb, at least 550 kb, at least 600 kb, at least 650 kb, at least 700 kb, at least 750 kb, at least 800 kb, at least 850 kb, at least 900 kb, at least 950 kb, at least 1 Mb, at least 1.5 Mb, at least 2 Mb, at least 2.5 Mb, at least 3 Mb, at least 4 Mb, at least 5 Mb, at least 6 Mb, at least 7 Mb, at least 8 Mb, at least 9 Mb, at least 10 Mb. In one embodiment, the size of the nucleic acid insert is from about 5 kb to about 700 kb. In one embodiment the size of the nucleic acid insert is from about 5 kb to about 500 kb. In another embodiment, the size of the nucleic acid insert is from about 100 kb to about 700 kb. In another embodiment the size of the nucleic acid insert is from about 100 kb to about 500 kb. In a specific embodiment, the nucleic acid insert is about 140 kb. In another specific embodiment, the nucleic acid insert is about 370 kb. In another specific embodiment, the nucleic acid insert is about 300 kb. In another specific embodiment, the nucleic acid insert is about 400 kb.

In some individual targeting vectors (i.e., prior to recombination with another targeting vector), the nucleic acid insert can be between 10-100 nucleotides in length, 100-500 nucleotides in length, 500 nucleotides-1 kb in length, 1 kb to 1.5 kb in length, 1.5 kb to 2 kb in length, 2 kb to 2.5 kb in length, 2.5 kb to 3 kb in length, or 3 kb to 5 kb in length. In other cases the length can be from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. Alternatively, the nucleic acid insert can be from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. Alternatively, the nucleic acid insert can be from about 400 kb to about 450 kb, from about 450 kb to about 500 kb, from about 500 kb to about 550 kb, from about 550 kb to about 600 kb, about 600 kb to about 650 kb, from about 650 kb to about 700 kb, from about 700 kb to about 750 kb, or from about 750 kb to about 800 kb.

In some cases, the replacement of the nucleic acid at the target locus results in the deletion of a nucleic acid sequence ranging from about 1 kb to about 200 kb, from about 2 kb to about 20 kb, or from about 0.5 kb to about 3 Mb. In some cases, the extent of the deletion is greater than a total length of the 5' homology arm and the 3' homology arm.

In some cases, the extent of the deletion of the nucleic acid sequence ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. Alternatively, the deletion can be from about 3 Mb to about 4 Mb, from about 4 Mb to about 5 Mb, from about 5 Mb to about 10 Mb, from about 10 Mb to about 20 Mb, from about 20 Mb to about 30 Mb, from about 30 Mb to about 40 Mb, from about 40 Mb to about 50 Mb, from about 50 Mb to about 60 Mb, from about 60 Mb to about 70 Mb, from about 70 Mb to about 80 Mb, from about 80 Mb to about 90 Mb, or from about 90 Mb to about 100 Mb.

In other cases, the nucleic acid insert or the corresponding nucleic acid at the target locus being replaced can be at least 10 kb, at least 20 kb, at least 30 kb, at least 40 kb, at least 50 kb, at least 60 kb, at least 70 kb, at least 80 kb, at least 90 kb, at least 100 kb, at least 120 kb, at least 150 kb, at least 200 kb, at least 250 kb, at least 300 kb, at least 350 kb, at least 400 kb, at least 450 kb, at least 500 kb, at least 550 kb, at least 600 kb, at least 650 kb, at least 700 kb or greater.

The nucleic acid insert can comprise genomic DNA or any other type of DNA. For example, the nucleic acid insert can be from a prokaryote, a eukaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest.

The nucleic acid insert and/or the nucleic acid at the target locus can comprise a coding sequence or a non-coding sequence, such as a regulatory element (e.g., a promoter, an enhancer, or a transcriptional repressor-binding element). For example, the nucleic acid insert can comprise a knock-in allele of at least one exon of an endogenous gene, or a knock-in allele of the entire endogenous gene (i.e., "gene-swap knock-in"). For example, the nucleic acid insert can be homologous or orthologous to a sequence being targeted for deletion at the genomic target locus. The homologous or orthologous nucleic acid insert can replace the sequence being targeted for deletion at the genomic locus of interest. This can result in humanization of a locus if insertion of the nucleic acid insert results in replacement of a non-human nucleic acid sequence with a homologous or orthologous human nucleic acid sequence (i.e., the nucleic acid insert is inserted in place of the corresponding non-human DNA sequence at its endogenous genomic locus).

The nucleic acid insert can also comprise a conditional allele. The conditional allele can be a multifunctional allele, as described in US 2011/0104799, which is incorporated by reference in its entirety. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, for example, US 2011/0104799, which is incorporated by reference in its entirety. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See US 2011/0104799.

Some nucleic acid inserts comprise a polynucleotide encoding a selection marker. The selection marker can be contained in a selection cassette. Such selection markers include, but are not limited, to neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

In some targeting vectors, the nucleic acid insert comprises a reporter gene. Examples of reporter genes are genes encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, alkaline phosphatase, and a combination thereof. Such reporter genes can be operably linked to a promoter active in a cell being targeted. Examples of promoters are described elsewhere herein.

In some targeting vectors, the nucleic acid insert comprises one or more expression cassettes or deletion cassettes. A given cassette can comprise a nucleotide sequence of interest, a nucleic acid encoding a selection marker, and/or a reporter gene, along with various regulatory components that influence expression. Examples of selectable markers and reporter genes that can be included are discussed in detail elsewhere herein.

In some targeting vectors, the nucleic acid insert comprises a nucleic acid flanked by site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, and a combination thereof. In one example, the site-specific recombination sites flank a polynucleotide encoding a selection marker and/or a reporter gene contained within the nucleic acid insert. Following integration of the nucleic acid insert at a targeted locus, the sequences between the site-specific recombination sites can be removed.

B. Polynucleotides of Interest

Any polynucleotide of interest may be contained in the various nucleic acid inserts and thereby integrated at the target genomic locus. The methods disclosed herein, provide for at least 1, 2, 3, 4, 5, 6 or more polynucleotides of interest to be integrated into the targeted genomic locus.

The polynucleotide of interest within the nucleic acid insert when integrated at the target genomic locus can introduce one or more genetic modifications into the cell. The genetic modification can comprise a deletion of an endogenous nucleic acid sequence and/or the addition of an exogenous or heterologous or orthologous polynucleotide into the target genomic locus. In one embodiment, the genetic modification comprises a replacement of an endogenous nucleic acid sequence with an exogenous polynucleotide of interest at the target genomic locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof in a target genomic locus. Such modifications may occur upon integration of the first, second, third, fourth, fifth, six, seventh, or any subsequent nucleic acid inserts into the target genomic locus.

The polynucleotide of interest within the nucleic acid insert and/or integrated at the target genomic locus can comprise a sequence that is native or homologous to the cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. "Homologous" in reference to a sequence includes a sequence that is native to the cell. "Heterologous" in reference to a sequence includes a sequence that originates from a foreign species, or, if from the same species, is substantially modified from its native form in composition and/or genomic locus by deliberate human intervention. "Exogenous" in reference to a sequence includes a sequence that originates from a foreign species. "Orthologous" includes a polynucleotide from one species that is functionally equivalent to a known reference sequence in another species (i.e., a species variant). The polynucleotide of interest can be from any organism of interest including, but not limited to, non-human, a rodent, a hamster, a mouse, a rat, a human, a monkey, an avian, an agricultural mammal or a non-agricultural mammal. The polynucleotide of interest can further comprise a coding region, a non-coding region, a regulatory region, or a genomic DNA. Thus, the $1^{st}$, $2^{nd}$, $3^{rd}$, $4^{th}$, $5^{th}$, $6^{th}$, $7^{th}$, and/or any of the subsequent nucleic acid inserts can comprise such sequences.

In one embodiment, the polynucleotide of interest within the nucleic acid insert and/or integrated at the target genomic locus is homologous to a human nucleic acid. In still further embodiments, the polynucleotide of interest integrated at the target locus is a fragment of a genomic nucleic acid. In one embodiment, the genomic nucleic acid is a mouse genomic nucleic acid, a human genomic nucleic acid, a non-human nucleic acid, a rodent nucleic acid, a rat nucleic acid, a hamster nucleic acid, a monkey nucleic acid, an agricultural mammal nucleic acid or a non-agricultural mammal nucleic acid or a combination thereof.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 700 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 300 kb, from about 300 kb to about 400 kb, from about 400 kb to about 500 kb, from about 500 kb to about 600 kb or from about 600 kb to about 700 kb.

The polynucleotide of interest within the nucleic acid insert and/or inserted at the target genomic locus can encode a polypeptide, can encode an miRNA, can encode a long non-coding RNA, or it can comprise any regulatory regions or non-coding regions of interest including, for example, a regulatory sequence, a promoter sequence, an enhancer sequence, a transcriptional repressor-binding sequence, or a deletion of a non-protein-coding sequence, but does not comprise a deletion of a protein-coding sequence. In addition, the polynucleotide of interest within the nucleic acid insert and/or inserted at the target genomic locus can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof.

The polynucleotide of interest within the nucleic acid insert and/or integrated at the target genomic locus can comprise a genetic modification in a coding sequence. Such genetic modifications include, but are not limited to, a deletion mutation of a coding sequence or the fusion of two coding sequences.

The polynucleotide of interest within the nucleic acid insert and/or integrated at the target genomic locus can comprise a polynucleotide encoding a mutant protein. In one embodiment, the mutant protein is characterized by an altered binding characteristic, altered localization, altered expression, and/or altered expression pattern. In one embodiment, the polynucleotide of interest within the nucleic acid insert and/or integrated at the genomic target locus comprises at least one disease allele. In such instances, the disease allele can be a dominant allele or the disease allele is a recessive allele. Moreover, the disease allele can comprise a single nucleotide polymorphism (SNP) allele. The polynucleotide of interest encoding the mutant protein can be from any organism, including, but not limited to, a mammal, a non-human mammal, rodent, mouse, rat, a human, a monkey, an agricultural mammal or a domestic mammal polynucleotide encoding a mutant protein.

The polynucleotide of interest within the nucleic acid insert and/or integrated at the target genomic locus can also comprise a regulatory sequence, including for example, a promoter sequence, an enhancer sequence, a transcriptional repressor-binding sequence, or a transcriptional terminator sequence. In specific embodiments, the polynucleotide of interest within the nucleic acid insert and/or integrated at the target genomic locus comprises a polynucleotide having a deletion of a non-protein-coding sequence, but does not comprise a deletion of a protein-coding sequence. In one embodiment, the deletion of the non-protein-coding sequence comprises a deletion of a regulatory sequence. In another embodiment, the deletion of the regulatory element comprises a deletion of a promoter sequence. In one embodiment, the deletion of the regulatory element comprises a deletion of an enhancer sequence. Such a polynucleotide of interest can be from any organism, including, but not limited to, a mammal, a non-human mammal, rodent, mouse, rat, a human, a monkey, an agricultural mammal or a domestic mammal polynucleotide encoding a mutant protein.

A targeted genetic modification can comprise a targeted alteration to a polynucleotide of interest. Such targeted modifications include, but are not limited to, additions of one or more nucleotides, deletions of one or more nucleotides, substitutions of one or more nucleotides, a knockout of the polynucleotide of interest or a portion thereof, a knock-in of the polynucleotide of interest or a portion thereof, a replacement of an endogenous nucleic acid sequence with a heterologous nucleic acid sequence, or a combination thereof. In specific embodiments, at least 1, 2, 3, 4, 5, 7, 8, 9, 10, 100, 500, or more nucleotides or at least 10 kb to 500 kb or more are changed to form the targeted genomic modification.

C. Targeting Vectors

Targeting vectors can be employed to introduce the nucleic acid insert into a genomic target locus and comprise the nucleic acid insert and homology arms that flank the nucleic acid insert. Targeting vectors can be in linear form or in circular form, and they can be single-stranded or double-stranded. Targeting vectors can be deoxyribonucleic acid (DNA) or ribonucleic acid (RNA). For ease of reference, the homology arms are referred to herein as 5' and 3' (i.e., upstream and downstream) homology arms. This terminology relates to the relative position of the homology arms to the nucleic acid insert within the targeting vector. The 5' and 3' homology arms correspond to regions within the targeted locus or to a region within another targeting vector, which are referred to herein as "5' target sequence" and "3' target sequence," respectively. In some cases, the homology arms can also function as a 5' or a 3' target sequence.

The present methods employ two, three or more targeting vectors which are capable of recombining with each other. In various embodiments, the targeting vectors are large targeting vectors (LTVEC) as described elsewhere herein. In such methods, the first, the second, and third targeting vectors each comprise a 5' and a 3' homology arm. The 3' homology arm of the first targeting vector comprises a sequence that overlaps with the 5' homology arm of the second targeting vector (i.e., overlapping sequences), which allows for homologous recombination between the first and the second LTVEC.

In the case of double targeting methods the 5' homology arm of the first targeting vector and the 3' homology arm of the second targeting vector are homologous to corresponding segments within the target genomic locus (i.e., the target sequence) which promotes homologous recombination of the first and the second targeting vectors with the corresponding genomic segments and modifies the target genomic locus.

In the case of triple targeting methods, the 3' homology arm of the second targeting vector comprises a sequence that overlaps with the 5' homology arm of the third targeting vector (i.e., overlapping sequences), which allows for homologous recombination between the second and the third LTVEC. The 5' homology arm of the first targeting vector and the 3' homology arm of the third targeting vector are homologous to corresponding segments within the target genomic locus (i.e., the target sequence) which promotes homologous recombination of the first and the third targeting vectors with the corresponding genomic segments and modifies the target genomic locus.

A homology arm and a target sequence or two homology arms "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found on the targeting vector (i.e., overlapping sequence) or between two homology arms can be any degree of sequence identity that allows for homologous recombination to occur. For example, the amount of sequence identity shared by the homology arm of the targeting vector (or a fragment thereof) and the target sequence of another targeting vector or a target sequence of the target genomic locus (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination.

Moreover, a corresponding region of homology between the homology arm and the corresponding target sequence can be of any length that is sufficient to promote homologous recombination at the target genomic locus. For example, a given homology arm and/or corresponding target sequence can comprise corresponding regions of homology that are at least about 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or more (such as described in the LTVEC vectors described elsewhere herein) such that the homology arm has sufficient homology to undergo homologous recombination with the corresponding target sequences within the target genomic locus of the cell or within another targeting vector.

The overlapping sequences of the 3' homology arm of the first targeting vector and the 5' homology arm of the second targeting vector or of the 3' homology arm of the second targeting vector and the 5' homology arm of the third targeting vector can be of any length that is sufficient to promote homologous recombination between the targeting vectors. For example, a given overlapping sequence of a homology arm can comprise corresponding overlapping regions that are at least about 1-5 kb, 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or more such that the overlapping sequence of the homology arm has sufficient homology to undergo homologous recombination with the corresponding overlapping sequence within another targeting vector. In one embodiment, the overlapping sequence is from 1-5 kb. In one embodiment, the overlapping sequence is from about 1 kb to about 70 kb. In one embodiment, the overlapping sequence is from about 10 kb to about 70 kb. In another embodiment, the overlapping sequence is from about 10 kb to about 50 kb. In one embodiment, the overlapping sequence is at least 10 kb. In another embodiment, the overlapping sequence is at least 20 kb. For example, the overlapping sequence can be from about 1 kb to about 5 kb, from about 5 kb to about 10 kb, from about 10 kb to about 15 kb, from about 15 kb to about 20 kb, from about 20 kb to about 25 kb, from about 25 kb to about 30 kb, from about 30 kb to about 35 kb, from about 35 kb to about 40 kb, from about 40 kb to about 45 kb, from about 45 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 120 kb, from about 120 kb to about 140 kb, from about 140 kb to about 160 kb, from about 160 kb to about 180 kb, from about 180 kb to about 200 kb, from about 200 kb to about 220 kb, from about 220 kb to about 240 kb, from about 240 kb to about 260 kb, from about 260 kb to about 280 kb, or about 280 kb to about 300 kb. As an example, the overlapping sequence can be from about 20 kb to about 60 kb. Alternatively, the overlapping sequence can be at least 1 kb, at least 5 kb, at least 10 kb, at least 15 kb, at least 20 kb, at least 25 kb, at least 30 kb, at least 35 kb, at least 40 kb, at least 45 kb, at least 50 kb, at least 60 kb, at least 70 kb, at least 80 kb, at least 90 kb, at least 100 kb, at least 120 kb, at least 140 kb, at least 160 kb, at least 180 kb, at least 200 kb, at least 220 kb, at least 240 kb, at least 260 kb, at least 280 kb, or at least 300 kb.

The homology arms can correspond to a locus that is native to a cell (e.g., the targeted locus), or alternatively they can correspond to a region of a heterologous or exogenous segment of DNA that was integrated into the genome of the cell, including, for example, transgenes, expression cassettes, or heterologous or exogenous regions of DNA. Alternatively, the homology arms can correspond to a region on a targeting vector in a cell. The homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library. In certain instances, the homology arms of the targeting vector correspond to a locus that is native, heterologous, or exogenous to a prokaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest. In some cases, the homology arms correspond to a locus of the cell that is not targetable using a conventional method or that can be targeted only incorrectly or only with significantly low efficiency in the absence of a nick or double-strand break induced by a nuclease agent (e.g., a Cas protein). In some cases, the homology arms are derived from synthetic DNA.

In some targeting vectors, one of the 5' or 3' homology arms corresponds to a targeted genomic locus while the other of the 5' or 3' homology arms corresponds to a region on another targeting vector.

In some targeting vectors, the 5' and 3' homology arms correspond to a targeted genome. Alternatively, the homology arms can be from a related genome. For example, the targeted genome is a mouse genome of a first strain, and the targeting arms are from a mouse genome of a second strain, wherein the first strain and the second strain are different. In certain instances, the homology arms are from the genome of the same animal or are from the genome of the same strain, e.g., the targeted genome is a mouse genome of a first strain, and the targeting arms are from a mouse genome from the same mouse or from the same strain.

A homology arm of a targeting vector can be of any length that is sufficient to promote a homologous recombination event with a corresponding target sequence, including, for example, at least 1-5 kb, 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or greater. As described in further detail below, large targeting vectors can employ targeting arms of greater length.

Nuclease agents (e.g., CRISPR/Cas systems) can be employed in combination with targeting vectors to aid in the modification of a target locus. Such nuclease agents may promote homologous recombination between the targeting vector and the target locus. When nuclease agents are employed in combination with a targeting vector, the targeting vector can comprise 5' and 3' homology arms corresponding to 5' and 3' target sequences located in sufficient proximity to a nuclease cleavage site so as to promote the occurrence of a homologous recombination event between the target sequences and the homology arms upon a nick or double-strand break at the nuclease cleavage site. The term "nuclease cleavage site" includes a DNA sequence at which a nick or double-strand break is created by a nuclease agent (e.g., a Cas9 cleavage site). The target sequences within the targeted locus that correspond to the 5' and 3' homology arms of the targeting vector are "located in sufficient proximity" to a nuclease cleavage site if the distance is such as to promote the occurrence of a homologous recombination event between the 5' and 3' target sequences and the homology arms upon a nick or double-strand break at the recognition site. Thus, in specific instances, the target sequences corresponding to the 5' and/or 3' homology arms of the targeting vector are within at least 1 nucleotide of a given recognition site or are within at least 10 nucleotides to about 14 kb of a given recognition site. In some cases, the nuclease cleavage site is immediately adjacent to at least one or both of the target sequences.

The spatial relationship of the target sequences that correspond to the homology arms of the targeting vector and the nuclease cleavage site can vary. For example, target sequences can be located 5' to the nuclease cleavage site, target sequences can be located 3' to the recognition site, or the target sequences can flank the nuclease cleavage site.

Combined use of the targeting vector (including, for example, a large targeting vector) with a nuclease agent can result in an increased targeting efficiency compared to use of the targeting vector alone. For example, when a targeting vector is used in conjunction with a nuclease agent, targeting efficiency of the targeting vector can be increased by at least two-fold, at least three-fold, at least 4-fold, at least 10-fold or within a range formed from these integers, such as 2-10-fold when compared to use of the targeting vector alone.

D. Large Targeting Vectors

Some targeting vectors are "large targeting vectors" or "LTVECs," which includes targeting vectors that comprise homology arms that correspond to and are derived from nucleic acid sequences larger than those typically used by other approaches intended to perform homologous recombination in cells. An LTVEC can be, for example, at least 10 kb in length, or the sum total of the 5' homology arm and the 3' homology arm can be, for example, at least 10 kb. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

The methods provided herein employ two or three LTVECs that are capable of recombining with each other and with the target genomic locus in a three-way or a four-way recombination event as described elsewhere herein. These methods make possible the modification of large loci that cannot be achieved using a single LTVEC.

Examples of LTVECs include vectors derived from a bacterial artificial chromosome (BAC), a human artificial chromosome, or a yeast artificial chromosome (YAC). Examples of LTVECs and methods for making them are described, e.g., in U.S. Pat. Nos. 6,586,251; 6,596,541; 7,105,348; and WO 2002/036789 (PCT/US01/45375), each of which is herein incorporated by reference. LTVECs can be in linear form or in circular form.

LTVECs can be of any length, including, for example, from about 20 kb to about 300 kb, from about 20 kb to about 50 kb, from about 50 kb to about 75 kb, from about 75 kb to about 100 kb, from about 100 kb to 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb or from about 275 kb to about 300 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR.

In some cases, an LTVEC comprises a nucleic acid insert ranging from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In other cases, the nucleic acid insert can range from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. In some cases, an LTVEC comprises a nucleic acid insert ranging from about 400 kb to about 450 kb, from about 450 kb to about 500 kb, from about 500 kb to about 550 kb, from about 550 kb to about 600 kb, about 600 kb to about 650 kb, from about 650 kb to about 700 kb, from about 700 kb to about 750 kb, or from about 750 kb to about 800 kb.

In some LTVECS, the sum total of the 5' homology arm and the 3' homology arm is at least 10 kb. In other LTVECs, the 5' homology arm ranges from about 1 kb to about 100 kb and/or the 3' homology arm ranges from about 1 kb to about 100 kb. The sum total of the 5' and 3' homology arms can be, for example, from about 1 kb to about 5 kb, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. Alternatively, each homology arm can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb.

In some cases, the LTVEC and nucleic acid insert are designed to allow for a deletion of the endogenous sequence at the target locus from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, from about 700 kb to about 800 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. Alternatively, the deletion can be from about 3 Mb to about 4 Mb, from about 4 Mb to about 5 Mb, from about 5 Mb to about 10 Mb, from about 10 Mb to about 20 Mb, from about 20 Mb to about 30 Mb, from about 30 Mb to about 40 Mb, from about 40 Mb to about 50 Mb, from about 50 Mb to about 60 Mb, from about 60 Mb to about 70 Mb, from about 70 Mb to about 80 Mb, from about 80 Mb to about 90 Mb, or from about 90 Mb to about 100 Mb. Alternatively, the deletion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In other cases, the LTVEC and nucleic acid insert are designed to allow for an insertion into the target locus of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. Alternatively, the insertion can be from about 400 kb to about 450 kb, from about 450 kb to about 500 kb, from about 500 kb to about 550 kb, from about 550 kb to about 600 kb, about 600 kb to about 650 kb, from about 650 kb to about 700 kb, from about 700 kb to about 750 kb, or from about 750 kb to about 800 kb. Alternatively, the insertion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In yet other cases, the nucleic acid insert and/or the region of the endogenous locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

E. Genomes and Target Genomic Loci

A genome or genomic target locus modified by the methods disclosed herein can include any segment or region of DNA within a cell. The genome or genomic target locus can be native to the cell, can be a heterologous or exogenous segment of DNA that was integrated into the genome of the cell, or can be a combination thereof. Such heterologous or exogenous segments of DNA can include transgenes, expression cassettes, polynucleotide encoding selection makers, or heterologous or exogenous regions of genomic DNA.

The genome or genomic target locus can also include extrachromosomal DNA within the cell, such as a yeast artificial chromosome (YAC), a bacterial artificial chromosome (BAC), a human artificial chromosome, or any other engineered genomic region contained in an appropriate host cell.

III. Nuclease Agents

The methods and compositions for modifying a target genomic locus provided herein can employ a nuclease agent that induces a nick or double-strand break into a desired recognition site.

The term "recognition site for a nuclease agent" includes a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desired to be positioned at the target locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary and includes, for example, recognition sites that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break into a desired recognition site can be used in the methods and compositions disclosed herein. A naturally occurring or native nuclease agent can be employed so long as the nuclease agent induces a nick or double-strand break in a desired recognition site. Alternatively, a modified or engineered nuclease agent can be employed. An "engineered nuclease agent" includes a nuclease that is engineered (modified or derived) from its native form to specifically recognize and induce a nick or double-strand break in the desired recognition site. Thus, an engineered nuclease agent can be derived from a native, naturally occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art (e.g., TAQMAN® qPCR assay, Frendewey D. et al., Methods in Enzymology, 2010, 476: 295-307, which is incorporated by reference herein in its entirety).

The recognition site of the nuclease agent can be positioned anywhere in or near the target locus. The recognition site can be located within a coding region of a gene, or within regulatory regions that influence the expression of the gene. A recognition site of the nuclease agent can be located in an intron, an exon, a promoter, an enhancer, a regulatory region, or any non-protein coding region. In specific embodiments, the recognition site is positioned within the polynucleotide encoding the selection marker. Such a position can be located within the coding region of the selection marker or within the regulatory regions, which influence the expression of the selection marker. Thus, a recognition site of the nuclease agent can be located in an intron of the selection marker, a promoter, an enhancer, a regulatory region, or any non-protein-coding region of the polynucleotide encoding the selection marker. In specific embodiments, a nick or double-strand break at the recognition site disrupts the activity of the selection marker. Methods to assay for the presence or absence of a functional selection marker are known.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148; all of which are herein incorporated by reference.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1 (each hereby incorporated by reference). In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 33-35 TAL repeats that recognize a single base pair via two hypervariable residues. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domains recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, for example, US20060246567; US20080182332; US20020081614; US20030021776; WO/2002/057308A2; US20130123484; US20100291048; WO/2011/017293A2; and Gaj et al. (2013) Trends in Biotechnology, 31(7):397-405, each of which is herein incorporated by reference.

In still another embodiment, the nuclease agent is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long recognition sites, and for tolerating some sequence polymorphisms in their DNA substrates. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002)

Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-DmoI.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.).

The nuclease agent employed in the various methods and compositions can also comprise a Clustered Regularly Interspersed Short Palindromic Repeats (CRISPR)/CRISPR-associated (Cas) system or components of such a system. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded. A Cas protein can have full cleavage activity and create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In some instances, a Cas protein is from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Cas9 proteins can also be from *Staphylococcus aureus*. Additional examples of the Cas9 family members include those described in WO 2014/131833, herein incorporated by reference in its entirety. In a specific example, the Cas9 protein is a Cas9 protein from *S. pyogenes* or is derived therefrom. The amino acid sequence of a Cas9 protein from *S. pyogenes* can be found, for example, in the SwissProt database under accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, hereby incorporated by reference in its entirety.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single strand break at a target sequence within a double-stranded DNA but not a double strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null Cas protein). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety. Such mutations can be generated using well-known methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference.

Cas proteins can also be fusion proteins. For example, a Cas protein can be fused to a cleavage domain, an epigenetic modification domain, a transcriptional activation domain, or a transcriptional repressor domain. See WO 2014/089290, incorporated herein by reference in its entirety. Cas proteins can also be fused to a heterologous polypeptide providing increased or decreased stability. The fused domain or heterologous polypeptide can be located at the N-terminus, the C-terminus, or internally within the Cas protein.

One example of a Cas fusion protein is a Cas protein fused to a heterologous polypeptide that provides for subcellular localization. Such sequences can include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105. A Cas protein can comprise, for example, one or more nuclear localization signals (e.g., two nuclear localization signals). Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also comprise a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism.

When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include, for example, promoters active in a pluripotent rat, eukaryotic, mammalian, non-human mammalian, human, rodent, mouse, or hamster cell. Examples of other promoters are described elsewhere herein.

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference. The terms "guide RNA" and "gRNA" are inclusive, including both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. The crRNA additionally provides the single stranded DNA-targeting segment that hybridizes to a target sequence. If used for modification within a cell, the exact sequence of a given crRNA or tracrRNA molecule can be designed to be specific to the species in which the RNA molecules will be used. See, for example, Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of *S. pyogenes*, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (target sequence) of the target DNA can have a length at least about 12 nt. For example, the DNA-targeting sequence (i.e., the sequence within the DNA-targeting segment that is complementary to a target sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at about 20 nt.

TracrRNAs can be in any form (e.g., full-length tracrRNAs or active partial tracrRNAs) and of varying lengths.

They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from *S. pyogenes* include 171-nucleotide, 89-nucleotide, 75-nucleotide, and 65-nucleotide versions. See, for example, Deltcheva et al. (2011) *Nature* 471:602-607; WO 2014/093661, each of which is incorporated herein by reference in their entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, incorporated herein by reference in its entirety.

The percent complementarity between the DNA-targeting sequence and the target sequence within the target DNA can be at least 60% (e.g., at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the target sequence within the target DNA is at least 60% over about 20 contiguous nucleotides. In one example, the percent complementarity between the DNA-targeting sequence and the target sequence within the target DNA is 100% over the 14 contiguous nucleotides at the 5' end of the target sequence within the complementary strand of the target DNA and as low as 0% over the remainder. In such a case, the DNA-targeting sequence can be considered to be 14 nucleotides in length. In another example, the percent complementarity between the DNA-targeting sequence and the target sequence within the target DNA is 100% over the seven contiguous nucleotides at the 5' end of the target sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activa-tors, transcriptional repressors, DNA methyltransferases, DNA demethylases, hi stone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively. Alternatively, the DNA encoding the gRNA can be provided as one DNA molecule.

When a DNA encoding a gRNA is introduced into a cell, the gRNA can be transiently, conditionally, or constitutively expressed in the cell. DNAs encoding gRNAs can be stably integrated in the genome of the cell and operably linked to a promoter active in the cell. Alternatively, DNAs encoding gRNAs can be operably linked to a promoter in an expression construct. For example, the DNA encoding the gRNA can be in a vector comprising a nucleic acid encoding a Cas protein. Alternatively, it can be in a vector or a plasmid that is separate from the vector comprising the nucleic acid encoding the Cas protein. Promoters that can be used in such expression constructs include promoters active, for example, in a pluripotent rat, eukaryotic, mammalian, non-human mammalian, human, rodent, mouse, or hamster cell. Such promoters can be, for example, conditional promoters, inducible promoters, constitutive promoters, or tissue-specific promoters. In some instances, the promoter is an RNA polymerase III promoter, such as a human U6 promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

A target sequence for a CRISPR/Cas system includes nucleic acid sequences present in a target DNA to which a DNA-targeting segment of a gRNA will bind, provided sufficient conditions for binding exist. For example, target sequences include sequences to which a guide RNA is designed to have complementarity, where hybridization between a target sequence and a DNA targeting sequence promotes the formation of a CRISPR complex. Full complementarity is not necessarily required, provided there is sufficient complementarity to cause hybridization and promote formation of a CRISPR complex. Target sequences also include cleavage sites for Cas proteins, described in more detail below. A target sequence can comprise any polynucleotide, which can be located, for example, in the nucleus or cytoplasm of a cell or within an organelle of a cell, such as a mitochondrion or chloroplast.

The target sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of a nucleic acid sequence present in a target DNA to which a DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a target sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence present in a target DNA to which a DNA-targeting segment of a gRNA will bind, the cleavage site is still considered to be within the "target sequence." The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins which produce a single-strand break at different cleavage sites on different strands, thereby producing a double-strand break. For example, a first nickase can create a single strand break on the first strand of double stranded DNA (dsDNA), while a second nickase can create a single strand break on the second strand of dsDNA such that overhanging sequences are created. In some cases, the target sequence of the nickase on the first strand is separated from the target sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the target sequence. Optionally, the target sequence can be flanked on the 3' end by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the target sequence of the non-complementary strand of the target DNA. As such, the PAM sequence of the complementary strand would be 5'-$CCN_2$-3', where $N_2$ is any DNA nucleotide and is immediately 5' of the target sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A).

Examples of target sequences include a DNA sequence complementary to the DNA-targeting segment of a gRNA, or such a DNA sequence in addition to a PAM sequence. One example of a target sequence comprises the nucleotide sequence of GNNNNNNNNNNNNNNNNNNNNG ($GN_{1-20}GG$; SEQ ID NO: 1). The guanine at the 5' end can facilitate transcription by RNA polymerase in cells. Other examples of target sequences can include two guanine nucleotides at the 5' end to facilitate efficient transcription by T7 polymerase in vitro. See, e.g., WO 2014/065596, herein incorporated by reference in its entirety for all purposes. Other target sequences can have between 4-22 nucleotides in length of SEQ ID NO: 1, including the 5' G and the 3' GG. Yet other target sequences can have between 14 and 20 nucleotides in length of SEQ ID NO: 1.

The target sequence can be any nucleic acid sequence endogenous or exogenous to a cell. The target sequence can be a sequence coding a gene product (e.g., a protein) or a non-coding sequence (e.g., a regulatory sequence or junk DNA) or can include both.

Active variants and fragments of nuclease agents (i.e. an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

The nuclease agent may be introduced into the pluripotent cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally, or constitutively expressed within the cell. Thus, the polynucleotide encoding the nuclease agent can be contained in an expression cassette and be operably linked to a conditional promoter, an inducible promoter, a constitutive promoter, or a tissue-specific promoter. Alternatively, the nuclease agent is introduced into the cell as an mRNA encoding a nuclease agent.

In specific embodiments, the polynucleotide encoding the nuclease agent is stably integrated in the genome of the cell and operably linked to a promoter active in the cell. In other embodiments, the polynucleotide encoding the nuclease agent is in the same targeting vector comprising the nucleic acid insert, while in other instances the polynucleotide encoding the nuclease agent is in a vector or a plasmid that is separate from the targeting vector comprising the nucleic acid insert.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring polynucleotide sequence.

The various methods set forth above can be sequentially repeated to allow for the targeted integration of any number of nucleic acid inserts into a given targeted genomic locus on a chromosome. Thus, the various methods provide for the insertion of at least 1, 2, 3, 4, 5, 6, 7, 8, 9, 10, 11, 12, 13, 14, 15, 16, 17, 18, 19, 20 or more nucleic acid inserts into the target genomic locus on a chromosome. In particular embodiments, such sequential tiling methods allow for the reconstruction of large genomic regions from an animal cell or from a mammalian cell (i.e., a human, a non-human, a rodent, a mouse, a monkey, a rat, a hamster, a domesticated mammal or an agricultural animal) into a targeted genomic locus on a chromosome. In such instances, the transfer and reconstruction of genomic regions that include both coding and non-coding regions allow for the complexity of a given region to be preserved by retaining, at least in part, the coding regions, the non-coding regions and the copy number variations found within the native genomic region. Thus, the various methods provide, for example, methods to generate "heterologous" or "exogenous" genomic regions within a cell.

IV. Selection Markers

The various methods and compositions provided herein can employ the nuclease agents and their corresponding recognition sites in combination with selection markers. As discussed herein, the position of the recognition site in the polynucleotide encoding the selection marker allows for an efficient method by which to identify integration events at the target locus. Moreover, various methods are provided herein wherein alternating selection markers having the nuclease recognition site are employed to improve the efficiency and efficacy through which multiple polynucleotides of interest are integrated within a given targeted locus.

Various selection markers can be used in the methods and compositions disclosed herein. Such selection markers can, for example, impart resistance to an antibiotic such as G418, hygromycin, blasticidin, neomycin, or puromycin. Such selection markers include neomycin phosphotransferase ($neo^r$), hygromycin B phosphotransferase ($hyg^r$), puromycin-N-acetyltransferase ($puro^r$), and blasticidin S deaminase ($bsr^r$). In still other embodiments, the selection marker is operably linked to an inducible promoter and the expression of the selection marker is toxic to the cell. Non-limiting examples of such selection markers include xanthine/guanine phosphoribosyl transferase (gpt), hypoxanthine-guanine phosphoribosyltransferase (HGPRT) or herpes simplex virus thymidine kinase (HSV-TK).

In one embodiment, the nuclease recognition site is positioned within a gene encoding a selection marker. In a specific embodiment, the nuclease recognition site is positioned within a hygromycin gene.

The polynucleotide encoding the selection markers are operably linked to a promoter active in the cell. Such expression cassettes and their various regulatory components are discussed in further detailed elsewhere herein.

V. Promoters

Various nucleic acid sequences described herein can be operably linked to promoters. Such promoters can be active, for example, in a pluripotent, eukaryotic, mammalian, non-human mammalian, human, rodent, mouse, or hamster cell. A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

A promoter can also be selected based on cell type. For example, various known promoters find use in a eukaryotic cell, a mammalian cell, a non-human cell, a non-human mammalian cell, a pluripotent cell, a non-human pluripotent cell, a human pluripotent cell, a human ES cell, a human adult stem cell, a developmentally-restricted human progenitor cell, a human iPS cell, a human cell, a rodent cell, a rat cell, a mouse cell, a hamster cell, a fibroblast, or a CHO cell.

VI. Expression Cassettes

Provided herein are polynucleotides or nucleic acid molecules comprising the various components of the targeting system provided herein (i.e. nuclease agents, recognition sites, nucleic acid inserts, polynucleotides of interest, targeting vectors (i.e., LTVECs), selection markers and other components).

Further provided are recombinant polynucleotides comprising the various components of the targeting system. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Genetic elements required to successfully transform, select, and propagate host cells and comprising any of the isolated nucleic acid fragments are provided herein. Screening may be accomplished by Southern analysis of DNA, Northern analysis of mRNA expression, immunoblotting analysis of protein expression, or phenotypic analysis, among others.

In specific embodiments, one or more of the components of the targeting system described herein can be provided in an expression cassette for expression in a prokaryotic cell, a eukaryotic cell, a bacterial, a yeast cell, a mammalian cell or other organism or cell type of interest. The cassette can include 5' and 3' regulatory sequences operably linked to a polynucleotide provided herein. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation.

The cassette may additionally contain at least one additional polynucleotide of interest to be co-introduced into the organism. Alternatively, the additional polynucleotide of interest can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

The expression cassette containing the polynucleotides provided herein can also comprise a selection marker gene for the selection of transformed cells. Selection marker genes are utilized for the selection of transformed cells or tissues.

Where appropriate, the sequences employed in the methods and compositions (i.e., the polynucleotide of interest, the nuclease agent, etc.) may be optimized for increased expression in the cell. That is, the genes can be synthesized using codons preferred in a given cell of interest including, for example, mammalian-preferred codons, human-preferred codons, rodent-preferred codon, mouse-preferred codons, rat-preferred codons, etc. for improved expression.

In one embodiment, the nuclease agent is expressed from an expression construct comprising a nucleic acid sequence encoding a nuclease and the nucleic acid is operably linked to a promoter active in the cell.

VII. Methods of Making Genetically Modified Non-Human Animals

Genetically modified non-human animals can be generated employing the various methods disclosed herein. In some cases, the method of producing a genetically modified non-human animal comprises: (1) modifying the genome of a pluripotent cell using the methods described herein; (2) selecting the genetically modified pluripotent cell; (3) introducing the genetically modified pluripotent cell into a host embryo; and (4) implanting the host embryo comprising the genetically modified pluripotent cell into a surrogate mother. A progeny from the genetically modified pluripotent cell is generated. The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. The pluripotent cell can be an ES cell (e.g., a mouse ES cell or a rat ES cell) as discussed elsewhere herein. See, for example, U.S. Pat. No. 7,294,754, herein incorporated by reference.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of media known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

The methods can further comprise methods of producing an F0 generation non-human animal comprising: (1) identifying a non-human ES cell comprising the targeted modification; (2) introducing the non-human ES cell comprising the targeted modification into a non-human host embryo; and (3) gestating the non-human host embryo in a surrogate mother. The surrogate mother can then produce the F0 generation non-human animal comprising the targeted modification. The host embryo comprising the genetically modified pluripotent or totipotent cell (e.g., a non-human ES cell) can be incubated until the blastocyst stage and then implanted into a surrogate mother to produce an F0 animal. Animals bearing the genetically modified genomic locus can be identified via a modification of allele (MOA) assay as described herein.

The various methods provided herein allow for the generation of a genetically modified non-human F0 animal wherein the cells of the genetically modified F0 animal that comprise the targeted modification. It is recognized that depending on the method used to generate the F0 animal, the number of cells within the F0 animal that have the targeted genetic modification will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the targeted genetic modification. In specific instances, at least 50%, 60%, 65%, 70%, 75%, 85%, 86%, 87%, 88%, 89%, 90%, 91%, 92%, 93%, 94%, 95%, 96%, 97%, 98%, 99% or 100% of the cellular contribution of the non-human F0 animal comprises a cell population having the targeted modification. In other instances, at least one or more of the germ cells of the F0 animal have the targeted modification.

In some instances, the cells of the genetically modified F0 animal are heterozygous or compound heterozygous for the targeted modification. For example, the cells of the genetically modified F0 animal can be hemizygous for the targeted modification. In other instances, the cells of the genetically modified F0 animal are homozygous for the targeted modification.

In some cases, the F0 animal generated by the methods and compositions disclosed herein can be bred to a wild-type animal to generate an F1 generation that is heterozygous for the targeted modification. Animals from the F1 generation can then be bred to each other to generate an F2 animal homozygous for the targeted modification. The F1 progeny can be genotyped using specific primers and/or probes to determine if the targeted genetic modification is present.

VIII. Methods of Introducing Nucleic Acids and Proteins into Cells

Various methods and compositions are provided herein to allow for introduction of a nucleic acid into a cell. In some cases, the system employed for introducing the nucleic acid allows for the targeted integration at a specific genomic locus. Such systems employ a variety of components and for ease of reference, the term "targeted genomic integration system" generically includes all the components required for an integration event (e.g., one or more nuclease agents, nuclease cleavage sites, nucleic acid inserts, targeting vectors, target genomic loci, and polynucleotides of interest).

The methods provided herein can comprise introducing into a cell one or more polynucleotides or polypeptide constructs comprising one or more components of a targeted genomic integration system. "Introducing" includes presenting to the cell the sequence (polypeptide or polynucleotide) in such a manner that the sequence gains access to the interior of the cell. The methods provided herein do not depend on a particular method for introducing a nucleic acid or protein into the cell, only that the nucleic acid or protein gains access to the interior of a least one cell. Methods for introducing nucleic acids and proteins into various cell types are known in the art and include, for example, stable transfection methods, transient transfection methods, and virus-mediated methods.

In some cases, the cells employed in the methods and compositions have a DNA construct stably incorporated into their genome. "Stably incorporated" or "stably introduced" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

Transfection protocols as well as protocols for introducing polypeptides or polynucleotide sequences into cells may vary. Transfection methods include chemical-based transfection methods using liposomes; nanoparticles; calcium phosphate (Graham et al. (1973) *Virology* 52 (2): 456-67, Bacchetti et al. (1977) *Proc Natl Acad Sci USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

In some cases, the introduction of nucleic acids or proteins into a cell is mediated by electroporation, by intracytoplasmic injection, by viral infection, by adenovirus, by lentivirus, by retrovirus, by transfection, by lipid-mediated transfection, or by Nucleofection™.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

When both nuclease agents and targeting vectors (e.g., LTVECs) are introduced into the cell, they can be introduced simultaneously. Alternatively, the nuclease agent can be introduced separately from the targeting vectors. For example, the nuclease agent can be introduced prior to the introduction of the targeting vectors, or it can be introduced following introduction of the targeting vectors. When two or more LTVECs are introduced into the cell, they can be introduced simultaneously, or alternatively, they can be introduced separately.

IX. Cells and Animals

Various compositions and methods provided herein employ cells, such as cells from an animal. Such cells can be non-human cells are can be from a non-human animal. Such cells can be eukaryotic cells, including, for example, fungal cells (e.g., yeast), plant cells, animal cells, mammalian cells, and human cells. A mammalian cell can be, for example, a non-human mammalian cell, a human cell, a rodent cell, a rat cell, a mouse cell, a hamster cell, a fibroblast, or a CHO cell. The eukaryotic cell can be a totipotent cell, a pluripotent cell, such as a non-human pluripotent cell (e.g., a mouse embryonic stem (ES) cell or a rat ES cell) or a human pluripotent cell, or a non-pluripotent cell. Totipotent cells include undifferentiated cells that can give rise to any cell type, and pluripotent cells include undifferentiated cells that possess the ability to develop into more than one differentiated cell type. Such pluripotent and/or totipotent cells can be, for example, embryonic stem (ES) cells or ES-like cells, such as an induced pluripotent stem (iPS) cells. Embryonic stem cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm). Such cells can also be hematopoietic stem cells or neuronal stem cells.

A eukaryotic cell can also be a cell that is not a primary somatic cell. Somatic cells can include any cell that is not a gamete, germ cell, gametocyte, or undifferentiated stem cell.

Eukaryotic cells also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Eukaryotic cells also include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells), and mouse embryonic fibroblast cells (e.g., 3T3 cells). Numerous types of immortalized cells are well known in the art.

Immortalized or primary cells include cells that are typically used for culturing or for expressing recombinant genes or proteins.

The term "animal," in reference to cells, pluripotent and/or totipotent cells, ES cells, donor cells, and/or host embryos, includes mammals, fishes, and birds. Mammals include, for example, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, for example, chickens, turkeys, ostrich, geese, ducks, etc. Domesticated animals and agricultural animals are also included. The term "non-human animal" excludes humans.

Mouse pluripotent and/or totipotent cells can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2. See, for example, Festing et al. (1999) *Mammalian Genome* 10:836). Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Mouse pluripotent and/or totipotent cells can also be from a mix of an aforementioned 129 strain and an aforementioned C57BL/6 strain (e.g., 50% 129 and 50% C57BL/6). Likewise, mouse pluripotent and/or totipotent calls can be from a mix of aforementioned 129 strains or a mix of aforementioned BL/6 strains (e.g., the 129S6 (129/SvEvTac) strain) A specific example of a mouse ES cell is a VGF1 mouse ES cell. See, for example, Auerbach et al. (2000) *Biotechniques* 29, 1024-1028, 1030, 1032, herein incorporated by reference in its entirety.

A rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, the rat pluripotent and/or totipotent cell can be from a DA strain or an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of a rat ES cell line from a DA rat are the DA.2B rat ES cell line and the DA.2C rat ES cell line. In some cases, the rat pluripotent and/or totipotent cells are from an inbred rat strain. See, e.g., U.S. 2014/0235933 A1, filed on Feb. 20, 2014, and U.S. 2014/0310828 A1, filed on Apr. 16, 2014, both of which are herein incorporated by reference in their entirety.

Examples of human pluripotent cells include human ES cells, human adult stem cells, developmentally restricted human progenitor cells, and human induced pluripotent stem (iPS) cells, such as primed human iPS cells and naïve human iPS cells. See, e.g., U.S. patent application Ser. No. 14/515,503, filed on Oct. 15, 2014 and herein incorporated by reference in its entirety. Induced pluripotent stem cells include pluripotent stem cells that can be derived directly from a differentiated adult cell. Human iPS cells can be generated by introducing specific sets of reprogramming factors into a cell which can include, for example, Oct3/4, Sox family transcription factors (e.g., Sox1, Sox2, Sox3, Sox15), Myc family transcription factors (e.g., c-Myc, 1-Myc, n-Myc), Krüppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, e.g., Takahashi and Yamanaka (2006) Cell 126:663-676. Primed human ES cells and primed human iPS cells include cells that express characteristics similar to those of post-implantation epiblast cells and are committed for lineage specification and differentiation. Naïve human ES cells and naïve human iPS cells include cells that express characteristics similar to those of ES cells of the inner cell mass of a pre-implantation embryo and are not committed for lineage specification. See, e.g., Nichols and Smith (2009) Cell Stem Cell 4:487-492.

Cells that have been implanted into a host embryo can be referred to as "donor cells." The genetically modified pluripotent and/or totipotent cell can be from the same strain as the host embryo or from a different strain. Likewise, the surrogate mother can be from the same strain as the genetically modified pluripotent and/or totipotent cell and/or the host embryo, or the surrogate mother can be from a different strain as the genetically modified pluripotent and/or totipotent cell and/or the host embryo.

A variety of host embryos can be employed in the methods and compositions disclosed herein. For example, the pluripotent and/or totipotent cells having the targeted genetic modification can be introduced into a pre-morula stage embryo (e.g., an 8-cell stage embryo) from a corresponding organism. See, e.g., U.S. Pat. Nos. 7,576,259, 7,659,442, 7,294,754, and US 2008/0078000 A1, all of which are incorporated by reference herein in their entireties. In other cases, the donor ES cells may be implanted into a host embryo at a pre-morula stage, e.g., 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo, an uncompacted morula stage embryo, or a compacted morula stage embryo. When employing a mouse embryo, the host embryo stage can be a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York. For example, the Theiler Stage can be selected from TS1, TS2, TS3, and TS4. In some cases, the host embryo comprises a zona pellucida, and the donor cell is an ES cell that is introduced into the host embryo through a hole in the zona pellucida. In other cases, the host embryo is a zona-less embryo. In yet other cases, the morula-stage host embryo is aggregated.

X. Methods of Identifying Cells with a Modified Target Genomic Locus

Some of the above methods further comprise identifying a cell having a modified target genomic locus (e.g., a modified genome). Various methods can be used to identify cells having a targeted modification, such as a deletion or an insertion. Such methods can comprise identifying one cell having the targeted modification at a target locus. Screening can be done to identify such cells with modified genomic loci.

The screening step can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

In other instances, cells having the targeted genetic modification are selected using methods that include, for example, Southern blot analysis, DNA sequencing, PCR analysis, or phenotypic analysis. Such cells are then employed in the various methods and compositions described herein.

Other examples of suitable quantitative assays include fluorescence-mediated in situ hybridization (FISH), comparative genomic hybridization, isothermic DNA amplification, quantitative hybridization to an immobilized probe(s), Invader Probes®, MMP Assays®, TAQMAN® Molecular Beacon, or Eclipse™ probe technology (see, for example, US2005/0144655, which is incorporated by reference herein in its entirety).

The screening step generally also comprises arm-specific assays, which are assays used to distinguish between correct targeted insertions of a nucleic acid insert into a target genomic locus from random transgenic insertions of the nucleic acid insert into genomic locations outside of the target genomic locus and are also used to detect correct assembly of two or more overlapping LTVECs into a single construct. Conventional assays for screening for targeted modifications, such as long-range PCR or Southern blotting, link the inserted targeting vector to the targeted locus. Because of their large homology arm sizes, however, LTVECs do not permit screening by such conventional assays. To screen LTVEC targeting, modification-of-allele (MOA) assays including loss-of-allele (LOA) and gain-of-allele (GOA) assays can be used (see, e.g., US 2014/0178879 and Frendewey et al. (2010) Methods Enzymol. 476:295-307, herein incorporated by reference in its entirety for all purposes). The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells. For a GOA assay, another TAQMAN® probe can be used to determine the Ct of the nucleic acid insert that is replacing the targeted gene(s) or locus(loci) by successful targeting.

It can be useful augment standard LOA and GOA assays to verify correct targeting by LTVECs. For example, LOA and GOA assays alone may not distinguish correctly targeted cell clones from clones in which a Cas-induced deletion of the target genomic locus coincides with random integration of a LTVEC elsewhere in the genome. Because the selection pressure in the targeted cell is based on the selection cassette, random transgenic integration of the LTVEC elsewhere in the genome will generally include the selection cassette and adjacent regions of the LTVEC but may exclude more distal regions of the LTVEC. For example, if a portion of an LTVEC is randomly integrated into the genome, and the LTVEC comprises a nucleic acid insert of around 5 kb or more in length with a selection cassette adjacent to the 3' homology arm, in some cases the 3' homology arm but not the 5' homology arm will be transgenically integrated with the selection cassette. Alternatively, if the selection cassette adjacent to the 5' homology arm, in some cases the 5' homology arm but not the 3' homology arm will be transgenically integrated with the selection cassette. As an example, if LOA and GOA assays are used to assess targeted integration of the LTVEC, and the GOA assay utilizes probes against the selection cassette or any other unique (non-arm) region of the LTVEC, a heterozygous deletion at the target genomic locus combined with a random transgenic integration of the LTVEC will give the same readout as a heterozygous targeted integration of the LTVEC at the target genomic locus. To verify correct targeting by the LTVEC, arm-specific assays can be used in conjunction with LOA and/or GOA assays.

Arm-specific assays determine copy numbers of a DNA template in LTVEC homology arms. Such homology arms can include a homology arm of an LTVEC that does not overlap with another LTVEC but corresponds with a target sequence in the cell (e.g., homology arm overlapping with genomic target sequence in a mouse cell (mArm)). Such homology arms can also include an overlapping homology arm present in two overlapping LTVECs (e.g., overlapping human sequence in 3' homology arm of a first LTVEC and 5' homology arm of a second LTVEC (hArm)). For experiments in which multiple overlapping LTVECs are introduced into a cell, screening generally comprises LOA assays, GOA assays for all unique inserted sequences, and arm-specific assays for all regions of homology (i.e., between LTVEC and target sequence in cell and between two different overlapping LTVECs). As an example, in the case of three overlapping LTVECs introduced into a mouse cell to humanize a wild type mouse target locus, the expected copy numbers for heterozygous targeted insertion would be as follows: 2 copies of 5' mArm (homology arm overlapping with 5' mouse target sequence), 1 copy of hArm1 (overlapping sequence between LTVECs 1 and 2), 1 copy of hArm2 (overlapping sequence between LTVECs 2 and 3), and 2 copies of 3' mArm (homology arm overlapping with 3' mouse target sequence). In the above example, mArm copy numbers greater than two would generally indicate transgenic LTVEC integration randomly outside of the target genomic locus rather than at the target genomic locus, which is undesirable. Correctly targeted clones would retain mArm copy numbers of two. In addition, mArm copy numbers of less than two in such arm-specific assays would generally indicate large Cas-mediated deletions extending beyond the region targeted for deletion, which are also undesirable. Likewise, for heterozygous targeted modifications, copy numbers of 1 for hArm1 and hArm2 would generally indicate that all three LTVECs have been assembled into a single construct.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Targeting the TCR Alpha Locus with Two LTVECs in Combination with Zinc Finger Nucleases A double targeting system was designed such that two large targeting vectors (LTVECs) modify a genomic locus in a single targeting step. As depicted in FIG. 1, a cell having a heterozygous modification of the TCR alpha locus on mouse chromosome 14 comprising a hygromycin selection cassette was targeted by the double targeting system to generate ES cells comprising additional Igκ variable gene segments.

This double targeting approach, summarized in FIG. 1, involves double targeting or co-electroporation of two different large targeting vectors (LTVECs) together with nucleotide sequences that encode an endonuclease (e.g., zinc finger nucleases) that creates a double strand break at or near the target locus into ES cells.

In this approach, the first large targeting vector (labeled as MAID 1710) comprised a 3' 30 kb homology arm that included the sequence of the human Vκ1-5 and Vκ1-6 gene segments, a 120 kb sequence that comprised the human Vκ3-7 to Vκ3-15 gene segments, and a 5' 20 kb region ("overlap region") that comprised the human Vκ1-16 gene segment. The second large targeting vector (labeled as MAID 6600) comprised a 3' 20 kb overlap region (region comprising the human Vκ1-16 gene segment, same as in the first vector), a 140 kb sequence comprising the human Vκ1-17 to Vκ2-30 gene segments, a FRT-Ub-Neo-FRT selection cassette and a 15.5 kb 3' mouse TCR A homology arm.

Zinc finger nucleases (ZFN) were designed that recognize and cleave a target sequence within the hygromycin resistance gene in order to promote homologous recombination of the two LTVECs at the target TCR A locus. The ES cells generated in FIG. 1 (MAID 6548, heterozygous for all human Jκ segments and four functional human Vκ gene segments) were electroporated with the two large targeting vectors (MAID6600 and MAID 1700-trimmed) described above and two plasmids that express each half of the ZFN (1/2), which bind to recognition sequences in the hygromycin resistance gene and catalyze a double-strand break at the target site

```
                                    (SEQ ID NO: 2)
(TGCGATCGCTGCGGCCGAtcttagCCAGACGAGCGGGTTCGG;
``` with cleavage site in lower case letters) (see Table 1). Two additional ZFNs were designed to target hygromycin: ZFN (3/4) that targets the hygromycin gene at nucleotide sequence

```
                                    (SEQ ID NO: 3)
CGCTGCGGCCGATCTtagccaGACGAGCGGGTTCGG;
``` and ZFN(5/6) that targets the hygromycin gene at nucleotide sequence

```
                                    (SEQ ID NO: 4)
AGCGTGTCCGACCTGATGcagctcTCGGAGGGCGAAGAA
```

(see Table 1).

TABLE 1

Hygromycin Zinc Finger Nuclease Binding and Cleavage Sites
(complementary strand not shown)

| Zinc Finger Nuclease | Zinc Finger Half | Binding Sequence (5'-3') | Cleavage Site (5'-3') |
|---|---|---|---|
| Hyg-ZFN(1,2) | Hyg-ZF1 | TGCGATCGCTGCGGCCGA (SEQ ID NO: 5) | TCTTAG |
|  | Hyg-ZF2 | CCGAACCCGCTCGTCTGG (SEQ ID NO: 6) | (SEQ ID NO: 11) |
| Hyg-ZFN(3,4) | Hyg-ZF3 | CGCTGCGGCCGATCT (SEQ ID NO: 7) | TAGCCA |
|  | Hyg-ZF4 | CCGAACCCGCTCGTC (SEQ ID NO: 8) | (SEQ ID NO: 12) |
| Hyg-ZFN(5,6) | Hyg-ZF5 | AGCGTGTCCGACCTGATG (SEQ ID NO: 9) | CAGCTC |
|  | Hyg-ZF6 | TTCTTCGCCCTCCGA (SEQ ID NO: 10) | (SEQ ID NO: 13) |

The two large targeting vectors were inserted by homologous recombination into the DNA sequence replacing the region containing and surrounding the Hyg selection cassette. The resulting ES cells contained at the endogenous TCR A locus a human immunoglobulin variable domain comprising human Jκ1 to Jκ5 and Vκ4-1 to Vκ2-30 gene segments. Successful incorporation of the two large targeting vectors was confirmed using the TAQMAN® assays described above (Lie and Petropoulos, 1998. Curr. Opin. Biotechnology 9:43-48, incorporated herein by reference), using probes and primers indicated in FIG. 1 and listed in Table 2 below (GOA=gain of allele; LOA=loss of allele; copy number=check for copy number of sequence to trace transgenic integration vs. targeted integration; hArm1=30 kb 3' homology arm of the first large targeting vector (MAID 1710); hArm2=20 kb overlap of the first (MAID 1710) and the second (MAID 6600) large targeting vectors, mArm=15.5 kb 5' homology arm of the second targeting vector (MAID 6600), WT mouse control—sequences present at the mouse TCR A locus). Real-time PCR assays recognizing sequences in the homology arms of the LTVECs, referred to as arm-specific assays, were used to verify correct targeting of the LTVEC into the mouse genome. Determining the copy number of these arm-specific assays provided further clarification to help distinguish correctly targeted ES clones, which retain, e.g., an mArm copy number of two, from clones in which a Cas9-induced deletion of the target mouse locus coincides with random integration of the LTVECs elsewhere in the genome, in which case the mArm copy number would be three (or more).

TABLE 2

| Gene | Assay | Forward Primer | Probe | Reverse Primer |
|---|---|---|---|---|
| HYG | LOA | TGCGGCCGATCTTAGCC (SEQ ID NO: 14) | ACGAGCGGGTTCGGCCCATTC (SEQ ID NO: 15) | TTGACCGATTCCTTGCGG (SEQ ID NO: 16) |
| HYG-U | LOA | CGACGTCTGTCGAGAAGTTTCTG (SEQ ID NO: 17) | AGTTCGACAGCGTGTCCGACCTGA (SEQ ID NO: 18) | CACGCCCTCCTACATCGAA (SEQ ID NO: 19) |
| Hyg-D | LOA | TGTCGGGCGTACACAAATCG (SEQ ID NO: 20) | CCGTCTGGACCGATGGCTGTGT (SEQ ID NO: 21) | GGGCGTCGGTTTCCACTATC (SEQ ID NO: 22) |
| PGKp1 (Hyg Promoter) | LOA | CAAATGGAAGTAGCACGTCTCACT (SEQ ID NO: 23) | CTCGTGCAGATGGACAGCACCGC (SEQ ID NO: 24) | CCGCTGCCCCAAAGG (SEQ ID NO: 25) |
| hIgK6 | Copy number of hArm1 | GTCAAGCACTGCTGGCACAC (SEQ ID NO: 26) | AACCCTTGTGCTATTGAATTGCTATGCTGTCAG (SEQ ID NO: 27) | TGTTGTAGACCCTCCGCCAC (SEQ ID NO: 28) |
| hIgK12 (MAID 1710 insert) | GOA | TTGCCTTTCTCACACCTGCAG (SEQ ID NO: 29) | CAGCCCATCCTGTCACTTCGCTGGA (SEQ ID NO: 30) | TGGCCCAACAGTACAGCTCAG (SEQ ID NO: 31) |
| hIgK13 | Copy number of hArm2 | TCAGTCAATCACCTTTCCCAGC (SEQ ID NO: 32) | TCCCCAGGTAGCCTCATGAACCAATGTT (SEQ ID NO: 33) | CACATTACTGAGTCCCCACAGGG (SEQ ID NO: 34) |
| hIgK14 | Copy number of hArm2 | CATTGTCAAAGAAGCACTGGAAATG (SEQ ID NO: 35) | ACCATTGCAGTTTACCCACGGTTAGGATTTTT (SEQ ID NO: 36) | TCTTGCAATGGGATCATCAGATG (SEQ ID NO: 37) |
| Neo | GOA | GGTGGAGAGGCTATTCGGC (SEQ ID NO: 38) | TGGGCACAACAGACAATCGGCTG (SEQ ID NO: 39) | GAACACGGCGGCATCAG (SEQ ID NO: 40) |
| hIgK15 | GOA | CAGGTGCAAAGGTGACCACAG (SEQ ID NO: 41) | TGGGTCCTGCCCATCCATGCA (SEQ ID NO: 42) | GGCAGCCTGAGTGTCAGAGC (SEQ ID NO: 43) |
| hIgK25 | GOA | GTTCAGGCCCCACAGACTCTC (SEQ ID NO: 44) | TCCTCTCTGGAGCAACCATGAAGTTCCT (SEQ ID NO: 45) | CCTGAAGCCATGAGGGCAG (SEQ ID NO: 46) |
| hUbC-D (Neo Promoter) | GOA | AGGGTAGGCTCTCCTGAATCG (SEQ ID NO: 47) | ACAGGCGCCGGACCTCTGGT (SEQ ID NO: 48) | CCAAAGAAACTGACGCCTCAC (SEQ ID NO: 49) |
| TCRA Arm4 | Copy number of mArm | GCGCCACATGAATTTGACCAG (SEQ ID NO: 50) | TGTACCCAATCTTCCAAAGAAAGAGCTG (SEQ ID NO: 51) | GGCATCCTGTCCTCCCTTC (SEQ ID NO: 52) |
| Parental 1540m1 | WT mouse control | CAGTAAGGGAAGAGACTACAACAGCAT (SEQ ID NO: 53) | TGCACACTGCTCACCACTGCAAGCTAT (SEQ ID NO: 54) | TGCTGGTGGCCCCATCT (SEQ ID NO: 55) |
| Parental 1540m3 | WT mouse control | GAACTCAGCTATGATAGTGTCGAATGTA (SEQ ID NO: 56) | CAGCCCAGCAGCTGTGGGTTCTC (SEQ ID NO: 57) | GCTCAGGGAGAACACAGAACTTAGA (SEQ ID NO: 58) |
| hIgK5 | MAID 6548 sequence | CCCCGTCCTCCTCCTTTTTC (SEQ ID NO: 59) | TCATGTCCATTAACCCATTTACCTTTTGCCCA (SEQ ID NO: 60) | TGCAAGTGCTGCCAGCAAG (SEQ ID NO: 61) |

The resulting targeted locus in ES cells had the following junction sequences, where mouse sequences are in parentheses, human sequences are in normal font, multiple cloning sites are bolded, and Frt sequences are italicized (Table 3).

TABLE 3

Junction Sequences of Locus Resulting from Double ES Cell Targeting

| Junction | Seq ID No | Sequence |
| --- | --- | --- |
| mouse Tcra/5' Frt | 62 | (GTCTTTTTTGTTCTTCACAGTTGAGCTTCA TCAAAGTCACATGGGTTAAACTCTATGGAG TAGTCAGAACACACTCTTCA)GAAGGGACTC CTGATTTCAAAGGGTACC_GAAGTTCCTATT CCGAAGTTCCTATTCTCTAGAAAGTATAGGAACTTC_ |
| 3' Frt/human IgK | 63 | _GAAGTTCCTATTCCGAAGTTCCTATTCTCTAG AAAGTATAGGAACTTC_CTAGGGTTTCACCG GTGGCGCGCCTAACAGAGAGGAAAGTCAAA TTATAAAGAATATGAGATTCAGAATTCTGA TTAACTGTGG |
| Human IgK/mouse Tcra | 64 | GATAAATTATTTTGTCAGACAACAATAA AAATCAATAGCACGCCCTAAGAGCGGCC GCCACCGCGGTGGAGCTC(AGGTTTCCG GTACTTAACAACAGAGCACAGATTTAGT GGTGAGGGACTCT) |

Modification of allele (MOA) screening of isolated ES cell colonies resulted in the identification of 27 correctly targeted clones among 960 colonies screened, for a targeting efficiency of 2.81%.

Figure 2:
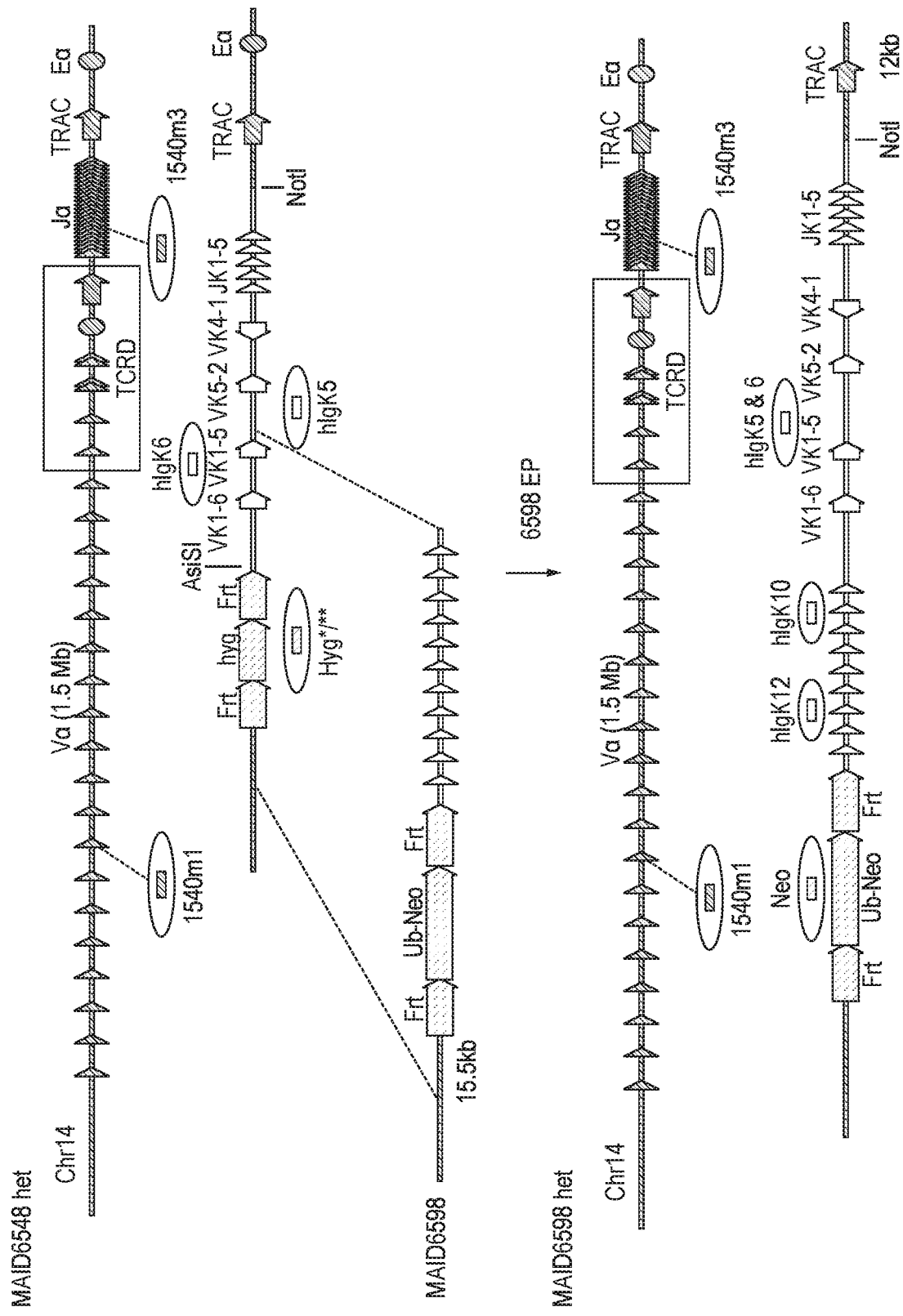
FIG. 2 provides a schematic for a single targeting event in which a cell having a heterozygous modification of the TCR alpha locus on mouse chromosome 14 comprising a hygromycin selection cassette is targeted with one large targeting vector comprising a neomycin selection cassette and 120 kb of human immunoglobulin kappa chain variable gene segments. The locations of the various probes used to confirm the targeting event are shown as encircled rectangles. Mouse sequence is represented by upward, diagonal hatching, human sequence is represented by no hatching, and recombination sites and selection cassettes are represented by downward, dashed, diagonal hatching. The schematic is not to scale and does not, for example, reflect the actual number of variable gene segments.

An alternative strategy for generating TCR A loci comprising additional immunoglobulin variable region gene segments involves serial targeting with successive large targeting vectors (see, e.g., FIG. 2). As such, ES cells heterozygous for all human Jκ gene segments and four functional human Vκ gene segments (MAID 6548) were electroporated with a large targeting vector comprising, from 5' to 3': a 15.5 kb 5' mouse homology arm, an Frt-Ub-Neo-Frt selection cassette, an 120 kb fragment comprising the Vκ3-7 to Vκ3-15 gene segments, and a 30 kb 3' human homology arm comprising the Vκ1-5 and Vκ1-6 gene segments (also present in MAID 6548 sequence). Successful incorporation was confirmed with TAQMAN® assays described above, using primers and probes that are listed in Table 2 above and indicated in FIG. 2: Hyg, hIgK5, hIgK6, hIgK12, Neo, parental 1540m3, parental 1540m1. In particular, the TCRA Arm4 and hIgK6 probes were used as arm-specific probes to validate correct genomic targeting of the LTVEC. An additional set of primers and probe, hIgK10, can also be used to confirm successful incorporation: Forward Primer—

CGATTATGACTGGTTAGGTAGAAAGGTG; (SEQ ID NO: 65)

Probe—

GCCACTGGTTTCTCCAAATGTTTTCAATCCAT; (SEQ ID NO: 66)

Reverse Primer—

GGGAGTACTTGGAGATCCCTAAGC. (SEQ ID NO: 67)

The resulting targeted locus in ES cells had the following junction sequences, where mouse sequences are in parentheses, human sequences are in normal font, multiple cloning sites are bolded, and Frt sequences are italicized (Table 4).

TABLE 4

Junction Sequence of Locus Resulting from Single ES Cell Targeting

| Junction | Seq ID No | Sequence |
| --- | --- | --- |
| mouse Tcra/ 5' FRt | 68 | (TTGAGCTTCATCAAAGTCACATGGGTTA AACTCTATGGAGTAGTCAGAACACACTCT TCA)GAAGGGACTCCTGATTTCAAAGGGT ACCG_AAGTTCCTATTCCGAAGTTCCTATT CTCTAGAAAGTATAGGAACTTC_ |
| 3' Frt/ human IgK | 69 | _GAAGTTCCTATTCCGAAGTTCCTATTCTC TAGAAAGTATAGGAACTTC_CTAGGGTTTC ACCGGTGGCGCGCCAGGACCCAGGCTCTG ACACTCAGGCTGCCAATACAATTGCCATG AAGACAGATGTTGATG |
| Human IgK/ mouse Tcra | 64 | GATAAATTATTTrGTCAGACAACAATAA AAATCAATAGCACGCCCTAAGAGCGGCC GCCACCGCGGTGGAGCTC(AGGTTTCCG GTACTTAACAACAGAGCACAGATTTAGT GGTGAGGGACTCT) |

MOA screening of isolated colonies resulted in the identification of 5 correctly targeted clones among 440 colonies screened (LTVEC alone), for a targeting efficiency of 1.1%. Results for screening of isolated colonies targeted with LTVEC+ZFN or LTVEC+CRISPR-Cas9 are shown in Table 9.

Upon completion of the single targeting depicted in FIG. 2, the ES cells may be successively targeted with large targeting vectors comprising additional Vκ in order to add up to the entire repertoire of functional human immunoglobulin Vκ gene segments.

In yet other alternative strategies, double or single targeting of successive additional human Ig Vκ gene segments may be accomplished using double (two large targeting vectors) or single (one large targeting vector) targeting schemes that involve zinc finger nuclease- or CRISPR-mediated destruction of a selection (e.g., hygromycin) cassette(s).

Targeted ES cells described above are used as donor ES cells and introduced into a pre-morula stage embryo, e.g., an 8-cell stage mouse embryo, by the VELOCIMOUSE® method (see, e.g., U.S. Pat. Nos. 7,576,259, 7,659,442, 7,294,754, and US 2008-0078000 A1). The mouse embryo comprising the donor ES cells is incubated until blastocyst stage and then implanted into a surrogate mother to produce an F0 mouse fully derived from the donor ES cells. F0 mice fully derived from the donor ES cell independently bearing a chimeric human IgK V-mouse Tcra C gene are identified by genotyping using a modification of allele assay that detects the presence of the unique gene sequences.

Example 2: Targeting Hygromycin Gene with Two LTVECs in Combination with CRISPR/Cas System The double targeting methods described in Example 1 utilizing zinc finger nucleases were also performed with a CRISPR/Cas9 system.

Various guide RNAs (gRNAs) were designed to recognize various target sequences within the hygromycin resistance gene (CRISPR recognition sequence). The CRISPR recognition sequences within the hygromycin gene were as follows: gRNA #1:

ACGAGCGGGTTCGGCCCATTCGG; (SEQ ID NO: 70)

gRNA #6:

CTTAGCCAGACGAGCGGGTTCGG; (SEQ ID NO: 71)

gRNA #10:

GCCGATCTTAGCCAGACGAGCGG; (SEQ ID NO: 72)

gRNA #16:

CGACCTGATGCAGCTCTCGGAGG. (SEQ ID NO: 73)

Figure 3:
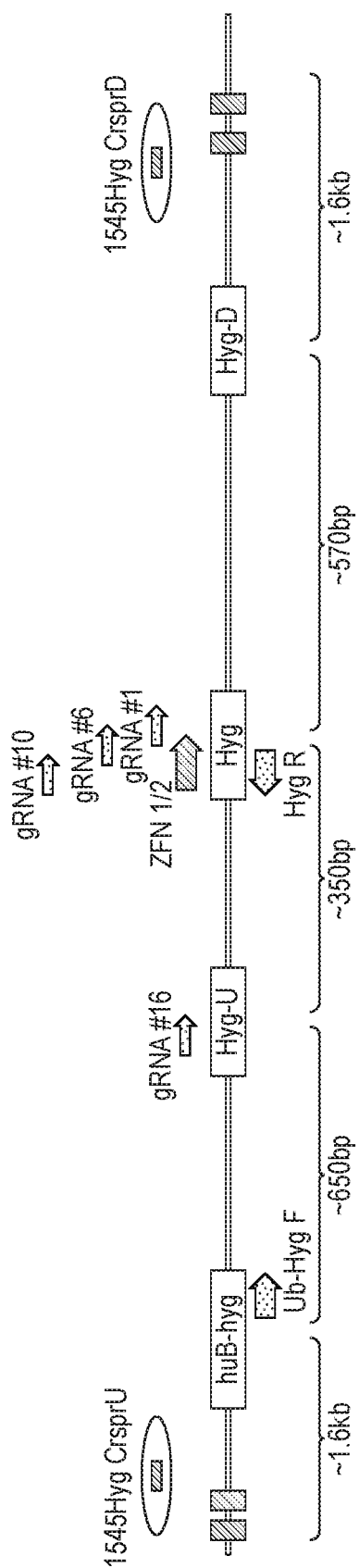
FIG. 3 provides a schematic for targeting and destruction of a hygromycin selection cassette using a CRISPR/Cas9 system and illustrates the position within the hygromycin gene of the CRISPR recognition sites for the various guide RNAs (gRNAs) that target different sequences in the hygromycin gene. The schematic is not to scale.

The locations of the recognition sequences within the hygromycin gene are depicted in FIG. 3, which depicts CRISPR/Cas-mediated destruction of the hygromycin in targeting vector MAID 1545. gRNA #1, gRNA #6, gRNA #10 and gRNA #16 were screened and were confirmed to specifically target the hygromycin gene (see FIG. 3). The results from primary screening using the various hygromycin specific gRNAs are provided in Table 5.

TABLE 5

Primary Screening Results Using Hygromycin-Specific gRNAs.

| gRNA/ZFN | Total # of Primary Candidates (2 Plates/Electroporation) | Positively Reconfirmed Candidates/ Total Reconfirmed |
|---|---|---|
| gRNA1 | 5 | 2/2 |
| gRNA6 | 6 | 1/1 |

TABLE 5-continued

Primary Screening Results Using Hygromycin-Specific gRNAs.

| gRNA/ZFN | Total # of Primary Candidates (2 Plates/Electroporation) | Positively Reconfirmed Candidates/ Total Reconfirmed |
|---|---|---|
| gRNA10 | 19 | 5/5 |
| gRNA16 | 91 | 8/8 |
| ZFN 1/2 | 10 | 4/4 |

ES cells, for example, the ES cell generated in FIG. 1 (MAID 6548, heterozygous for all human Jκ segments and four functional human Vκ gene segments) were electroporated with two large targeting vectors (described in Example 1), together with a single vector or with multiple vectors that encode Cas9 and a gRNA (for example, gRNA #1, gRNA #6, gRNA #10, or gRNA #16), which recognize and cleave a target site within the hygromycin resistance gene.

Two large targeting vectors were inserted by homologous recombination into the DNA sequence replacing the region containing and surrounding the Hyg selection cassette. Successful incorporation of the two large targeting vectors was confirmed using TAQMAN® assays.

The targeted ES cells described above will be used as donor ES cells and introduced into a pre-morula stage embryo, e.g., an 8-cell stage mouse embryo, by the VELOCIMOUSE® method (see, e.g., U.S. Pat. Nos. 7,576,259, 7,659,442, 7,294,754, and US 2008-0078000 A1). The mouse embryo comprising the genetically modified ES cells is incubated until blastocyst stage and then implanted into a surrogate mother to produce an F0 mouse fully derived from the donor ES cells. F0 mice fully derived from the donor ES cells will be identified by genotyping using a modification of allele assay that detects the presence of unique gene sequences.

Figure 4:
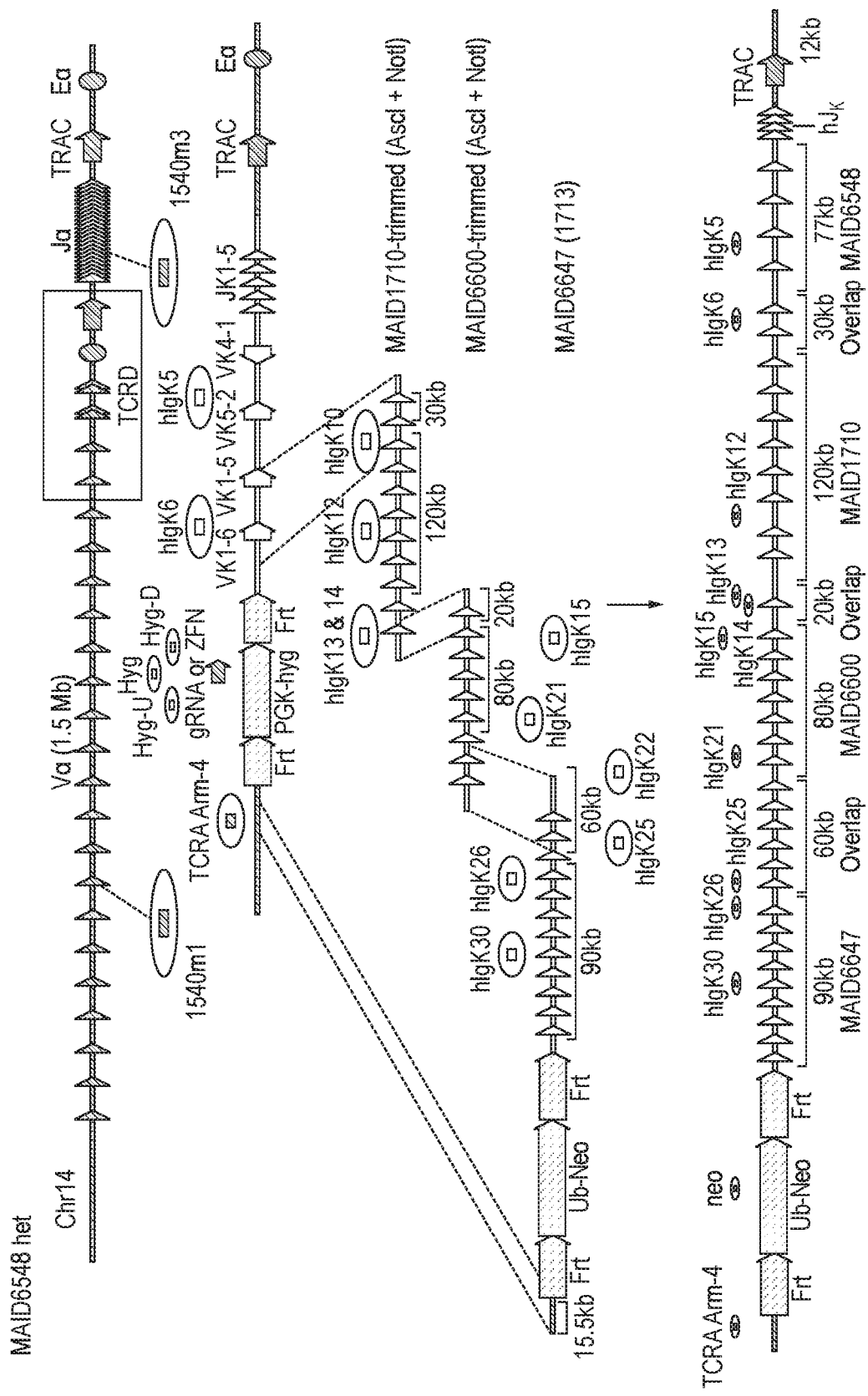
FIG. 4 provides a schematic for a genomic triple targeting event in which a cell having a heterozygous modification of the TCR alpha locus on mouse chromosome 14 comprising a hygromycin selection cassette is targeted. The hygromycin selection cassette is cleaved by a zinc finger nuclease (ZFN) or by a CRISPR/Cas complex and is targeted with three large targeting vectors comprising a neomycin selection cassette and about 370 kb of human immunoglobulin kappa chain variable gene segments. The large targeting vectors each comprise an overlapping sequence of about 20 kb to about 60 kb, which allows for homologous recombination between the large targeting vectors. The targeting event precisely inserted the human immunoglobulin kappa chain variable gene segments from all three targeting vectors in a single targeting step. The locations of the various probes used to confirm the targeting event are shown as encircled rectangles. Mouse sequence is represented by upward, diagonal hatching, human sequence is represented by no hatching, and recombination sites and selection cassettes are represented by downward, dashed, diagonal hatching. The schematic is not to scale and does not, for example, reflect the actual number of variable gene segments.

Example 3: Targeting the TCR Alpha Locus with Three LTVECs in Combination with Zinc Finger Nucleases A triple targeting system was designed such that three large targeting vectors (LTVECs) modify a genomic locus in a single targeting step. As depicted in FIG. 4, a cell having a heterozygous modification of the TCR alpha locus on mouse chromosome 14 comprising a hygromycin selection cassette was targeted by the triple targeting system to generate ES cells comprising additional Igκ variable gene segments.

This triple targeting approach, summarized in FIG. 4, involves triple targeting or co-electroporation of three different large targeting vectors (LTVECs) (MAID 6647, MAID 6600, and MAID 1710) together with nucleotide sequences that encode an endonuclease (e.g., zinc finger nucleases or Cas9 and gRNAs) that creates a double strand break at or near the target locus into ES cells.

In this approach, the first large targeting vector (labeled as MAID 1710) comprised a 3' 30 kb homology arm that includes the sequence of human Vκ1-5 and Vκ1-6 gene segments, a 120 kb sequence that comprised human Vκ3-7 to Vκ3-15 gene segments, and a 5' 20 kb region ("overlap region") that comprised human Vκ1-16 gene segment. The second large targeting vector (labeled as MAID 6600) comprised a 3' 20 kb overlap region (region comprising human Vκ1-16 gene segment, same as in the first vector), a 140 kb sequence comprising human Vκ1-17 to Vκ2-24 gene segments, and a 5' 60 kb region ("overlap region") that comprised human Vκ3-25 to Vκ2-30. The third large targeting vector (labeled as MAID 6647) comprised a 3' 60 kb overlap region (region comprising human Vκ3-25 to Vκ2-30, same as in the second vector), a 90 kb sequence comprising human Vκ3-31 to Vκ2-40, a FRT-Ub-Neo-FRT selection cassette and a 15.5 kb 5' mouse TCR A homology arm.

Zinc finger nucleases (ZFN) were designed that recognize and cleave a target sequence within the hygromycin resistance gene in order to promote homologous recombination of three LTVECs at the target TCR A locus. The ES cells generated in FIG. 4 (MAID 6548, heterozygous for all human Jκ segments and four functional human Vκ gene segments) were electroporated with the three large targeting vectors (MAID6600-trimmed, MAID 1700-trimmed and MAID6647) described above and two plasmids that express each half of the ZFN (1/2), which bind to recognition sequences in the hygromycin resistance gene and catalyze a double-strand break at the target site (SEQ ID NO: 2)
(TGCGATCGCTGCGGCCGAtcttagCCAGACGAGCGGGTTCGG;

with cleavage site in lower case letters) (see Table 1).

The three large targeting vectors were inserted by homologous recombination into the DNA sequence replacing the region containing and surrounding the Hyg selection cassette. The resulting ES cells contained at the endogenous TCR A locus a human immunoglobulin variable domain comprising human Jκ1 to Jκ5 and Vκ4-1 to Vκ2-40 gene segments. Successful incorporation of the three large targeting vectors was confirmed using the TAQMAN® assays described above (Lie and Petropoulos, 1998. Curr. Opin. Biotechnology 9:43-48, incorporated herein by reference), using probes and primers indicated in FIG. 4 and listed in Table 2 above and in Table 6 below (GOA=gain of allele; LOA=loss of allele; copy number=check for copy number of sequence to trace transgenic integration vs. targeted integration; hArm1=30 kb 3' homology arm of the first large targeting vector (MAID 1710); hArm2=20 kb overlap of the first (MAID 1710) and the second (MAID 6600) large targeting vectors, hArm3=60 kb overlap of the second (MAID 6600) and the third (MAID6647) targeting vectors, mArm=15.5 kb 5' homology arm of the third targeting vector (MAID 6647), WT mouse control—sequences present at the mouse TCR A locus). Real-time PCR assays recognizing sequences in the homology arms of the LTVECs, referred to as arm-specific assays, were used to verify correct targeting of the LTVEC into the mouse genome. Determining the copy number of these arm-specific assays provided further clarification to help distinguish correctly targeted ES clones, which retained a copy number of two for the mouse probe (mArm) and a copy number of one for the human probe (hArm1), from clones in which a Cas9-induced deletion of the target mouse locus coincides with random integration of the LTVECs elsewhere in the genome, in which case there would be a copy number of three (or more) for the mouse probe (mArm) and a copy number of two (or more) for the human probe (hArm1). To detect the correct assembly of the three LTVECs by homologous recombination into the desired locus, we utilized arm-specific TAQMAN® assays. The expected copy numbers, 1 for hArm2 and hArm3, indicated that all three LTVECs have been assembled into a single construct.

TABLE 6

TAQMAN Primers and Probes

| Gene | Assay | Forward Primer | Probe | Reverse Primer |
|---|---|---|---|---|
| HYG | LOA | TGCGGCCGATCTTAGC C (SEQIDNO: 14) | ACGAGCGGGTTCGGCCC ATTC (SEQ ID NO: 15) | TTGACCGATTCCTTGC GG (SEQ ID NO: 16) |
| HYG-U | LOA | CGACGTCTGTCGAGAA GTTTCTG (SEQ ID NO: 17) | AGTTCGACAGCGTGTCC GACCTGA (SEQ ID NO: 18) | CACGCCCTCCTACATC GAA (SEQ ID NO: 19) |
| Hyg-D | LOA | TGTCGGGCGTACACAA ATCG (SEQ ID NO: 20) | CCGTCTGGACCGATGGC TGTGT (SEQ ID NO: 21) | GGGCGTCGGTTTCCAC TATC (SEQ ID NO: 22) |
| hIgK6 | Copy number of hArm1 | GTCAAGCACTGCTGGC ACAC (SEQ ID NO: 26) | AACCCTTGTGCTATTGA ATTGCTATGCTGTCAG (SEQ ID NO: 27) | TGTTGTAGACCCTCCG CCAC (SEQ ID NO: 28) |
| hIK12 (MAID 1710 insert) | GOA | TTGCC11ICTCACACC TGCAG (SEQ ID NO: 29) | CAGCCCATCCTGTCACT TCGCTGGA (SEQ ID NO:30) | TGGCCCAACAGTACAG CTCAG (SEQ ID NO: 31) |
| hIgK13 | Copy number of hArm2 | TCAGTCAATCACCTTT CCCAGC (SEQ ID NO: 32) | TCCCCAGGTAGCCTCAT GAACCAATGTT (SEQ ID NO: 33) | CACATTACTGAGTCCC CACAGGG (SEQ ID NO: 34) |
| hIgK14 | Copy number of hArm2 | CATTGTCAAAGAAGCA CTGGAAATG(SEQ1D NO: 35) | ACCATTGCAGTTTACCC ACGGTTAGGA1TTTT (SEQ ID NO: 36) | TCTTGCAATGGGATCA TCAGATG (SEQ ID NO: 37) |
| Neo | GOA | GGTGGAGAGGCTATTC GGC (SEQ ID NO: 38) | TGGGCACAACAGACAAT CGGCTG (SEQ ID NO: 39) | GAACACGGCGGCATCA G (SEQ ID NO: 40) |
| hIgK15 | GOA | CAGGTGCAAAGGTGA CCACAG (SEQ ID NO: 41) | TGGGTCCTGCCCATCCA TGCA (SEQ ID NO: 42) | GGCAGCCTGAGTGTCA GAGC (SEQ ID NO: 43) |
| hIgK25 | Copy number of hArm3 | GTTCAGGCCCCACAGA CTCTC (SEQ ID NO: 44) | TCCTCTCTGGAGCAACC ATGAAGTTCCCT (SEQ ID NO: 45) | CCTGAAGCCATGAGGG CAG (SEQ ID NO: 46) |

TABLE 6-continued

TAQMAN Primers and Probes

| Gene | Assay | Forward Primer | Probe | Reverse Primer |
|------|-------|----------------|-------|----------------|
| TCRA Arm4 | Copy number of mArm | GCGCCACATGAATTTG ACCAG (SEQ ID NO: 50) | TGTACCCAATCTTCCAA AGAAAGAGCTG (SEQ ID NO: 51) | GGCATCCTGTCCTCCCT TC (SEQ ID NO: 52) |
| Parental 1540m1 | WT mouse control | CAGTAAGGGAAGAGA CTACAACAGCAT (SEQ ID NO: 53) | TGCACACTGCTCACCAC TGCAAGCTAT (SEQ ID NO: 54) | TGCTGGTGGCCCCATC T (SEQ ID NO: 55) |
| Parental 1540m3 | WT mouse control | GAACTCAGCTATGATA GTGTCGAATGTA (SEQ ID NO: 56) | CAGCCCAGCAGCTGTGG GTTCTC (SEQ ID NO: 57) | GCTCAGGGAGAACACA GAACTTAGA (SEQ ID NO: 58) |
| hIgK5 | MAID 6548 sequence (see Table 2) | CCCCGTCCTCCTCCTTT TTC (SEQ ID NO: 59) | TCATGTCCATTAACCCA TTTACCTTTTGCCCA (SEQ ID NO: 60) | TGCAAGTGCTGCCAGC AAG (SEQ ID NO: 51) |
| hIgK22 | Copy number of hArm | TGGCTCCAAGAACAGT TTGCC (SEQ ID NO: 74) | CCTGACTTTGCTGCTC AACTCACAGCC (SEQ ID NO: 75) | GGTCCAGTGGAATCTG CCATG (SEQ ID NO: 76) |
| hIgK21 | GOA | CATTTGGCTACATATC AAAGCCG (SEQ ID NO: 77) | CCTGAGCCAGGGAACA GCCCACTGATA (SEQ ID NO: 78) | ACATGGCTGAGGCAGA CACC (SEQ ID NO: 79) |
| hIgK26 | GOA | TGGGCCGTTATGCTAG TACCA (SEQ ID NO: 80) | TGGCTTTACCCCTTTTGA AGGGCCC (SEQ ID NO: 81) | CACAGCTGAAGCAGGA TGAGC (SEQ ID NO: 82) |
| hIgK230 | GOA | TCTCTGAGCAGCCATC CCC (SEQ ID NO: 83) | TTCTCCTTTGGTGTAGA GGGCACCAGC (SEQ ID NO: 84) | ACCAGGCATGGCAGAA AGG (SEQ ID NO: 85) |

The resulting targeted locus in ES cells had the following junction sequences, where mouse sequences are in parentheses, human sequences are in normal font, multiple cloning sites are bolded, and Frt sequences are italicized (Table 7).

TABLE 7

Junction Sequence of Locus Resulting from Triple ES Cell Targeting

| Junction | Seq ID No | Sequence |
|----------|-----------|----------|
| mouse Tcra/ 5' FRt | 62 | (GTCTTTTTTGTTCTTCACAGTTGAGCTTC ATCAAAGTCACATGGGTTAAACTCTATGG AGTAGTCAGAACACACTCTTCA) *GAAGGGA CTCCTGATTTCAAAGGGTACC*GAAGTTCC TATTCCGAAGTTCCTATTCTCTAGAAAGT ATAGGAACTTC |
| 3' Frt/ human IgK | 86 | *GAAGTTCCTATTCCGAAGTTCCTATTCTCT AGAAAGTATAGGAACTT*CTAGGGTTTCACC GGTGGCGCGCCTGAGTAGTGCTTTAGGTGT GTAATCACCAAAGATTTAGTGAAGTCCCTG TGCAAGGAG |
| Human IgK/ mouse Tcra | 64 | GATAAATTATTTrGTCAGACAACAATAA AAATCAATAGCACGCCCTAAGAGCGGCC GCCACCGCGGTGGAGCTC(AGGTTTCCG GTACTTAACAACAGAGCACAGATTTAGT GGTGAGGGACTCT) |

Modification of allele (MOA) screening of isolated ES cell colonies resulted in a targeting efficiency of 0.4% (see Table 8).

TABLE 8

Modification of Allele (MOA) Screening Results for Targeting with 3 LTVECs

| # LTVECs | Nuclease | Delete | Insert | Efficiency |
|----------|----------|--------|--------|------------|
| 3 LTVECs | ZFN | hyg | 370 kb human | 0.4% |
| 3 LTVECs | gRNA#16/ Cas9 | hyg | 370 kb human | 0.4% |
| 3 LTVECs | none | hyg | 370 kb human | 0% |

Targeted ES cells described above are used as donor ES cells and introduced into, a pre-morula stage embryo, e.g., an 8-cell stage mouse embryo by the VELOCIMOUSE® method (see, e.g., U.S. Pat. Nos. 7,576,259, 7,659,442, 7,294,754, and US 2008-0078000 A1). The mouse embryo comprising the donor ES cells is incubated until blastocyst stage and then implanted into a surrogate mother to produce an F0 mouse fully derived from the donor ES cells. F0 mice fully derived from the donor ES cell independently bearing a chimeric human IgK V-mouse Tcra C gene are identified by genotyping using a modification of allele assay that detects the presence of the unique gene sequences.

Example 4: Targeting Hygromycin Gene with Three LTVECs in Combination with CRISPR/Cas System The triple targeting methods described in Example 3 utilizing zinc finger nucleases was also performed with a CRISPR/Cas9 system.

Various guide RNAs (gRNAs) were designed to recognize various target sequences within the hygromycin resistance gene (CRISPR recognition sequence). The CRISPR recognition sequences within the hygromycin gene are as follows:
gRNA #1:

ACGAGCGGGTTCGGCCCATTCGG;   (SEQ ID NO: 70)

gRNA #6:

CTTAGCCAGACGAGCGGGTTCGG;   (SEQ ID NO: 71)

gRNA #10:

GCCGATCTTAGCCAGACGAGCGG;   (SEQ ID NO: 72)

gRNA #16:

CGACCTGATGCAGCTCTCGGAGG.   (SEQ ID NO: 73)

The locations of the recognition sequences within the hygromycin gene are depicted in FIG. 3. gRNA #1, gRNA #6, gRNA #10 and gRNA #16 were screened and were confirmed to specifically target the Hygromycin gene (see FIG. 3 and Table 5).

MAID 6548 ES cells (heterozygous for all human Jκ segments and four functional human Vκ gene segments) were electroporated with three large targeting vectors as described in Example 3, together with vectors that encode Cas9 and gRNA #16, which recognize and cleave a target site within the hygromycin resistance gene.

Three large targeting vectors were inserted by homologous recombination into the DNA sequence replacing the region containing and surrounding the Hyg selection cassette. Successful incorporation of the three large targeting vectors was confirmed using the TAQMAN® assays described in Example 3.

The resulting targeted locus in ES cells had the junction sequences shown in Table 7, where mouse sequences are in parentheses, human sequences are in normal font, multiple cloning sites are bolded, and Frt sequences are italicized.

Modification of allele (MOA) screening of isolated ES cell colonies resulted in a targeting efficiency of 0.4% (see Table 8).

The targeted ES cells described above will be used as donor ES cells and introduced into a pre-morula stage embryo, e.g., an 8-cell stage mouse embryo, by the VELOCIMOUSE® method (see, e.g., U.S. Pat. Nos. 7,576, 259, 7,659,442, 7,294,754, and US 2008-0078000 A1). The mouse embryo comprising the genetically modified ES cells is incubated until blastocyst stage and then implanted into a surrogate mother to produce an F0 mouse fully derived from the donor ES cells. F0 mice fully derived from the donor ES cells will be identified by genotyping using a modification of allele assay that detects the presence of unique gene sequences.

Example 5: Enhancement of LTVEC Targeting Via Overlapping Sequences Between Two LTVECs The double targeting system described in Example 1 was employed to modify a genomic locus in a single targeting step using two large targeting vectors (LTVECs). As depicted in FIG. 1, a cell having a heterozygous modification of the TCR alpha locus on mouse chromosome 14 comprising a hygromycin selection cassette was targeted by the double targeting system to generate ES cells comprising additional Igκ variable gene segments. The two different LTVECs were co-electroporated together into mouse embryonic stem (ES) cells. Optionally, a nucleic acid encoding an endonuclease (either a zinc finger nuclease (ZFN) or CRISPR-Cas9) was co-electroporated to create a double strand break at or near the target locus.

As in Example 1, the LTVEC (labeled as MAID 1710) comprised a 3' 30 kb homology arm that included the sequence of human Vκ1-5 and Vκ1-6 gene segments, a 120 kb sequence that comprised human Vκ3-7 to Vκ3-15 gene segments, and a 5' 20 kb region ("overlap region") that comprised a human Vκ1-16 gene segment. The second LTVEC (labeled as MAID 6600) comprised a 3' 20 kb overlap region (region comprising human Vκ1-16 gene segment, same as in the first vector), a 140 kb sequence comprising human Vκ1-17 to Vκ2-30 gene segments, a FRT-Ub-Neo-FRT selection cassette, and a 15.5 kb 3' mouse TCR A homology arm.

Successful targeting resulted in insertion of the two LTVECs by homologous recombination into the DNA sequence replacing the region containing and surrounding the Hyg selection cassette. The resulting ES cells contained at the endogenous TCR A locus a human immunoglobulin variable domain comprising human Jκ1 to Jκ5 and Vκ4-1 to Vκ2-30 gene segments. Successful incorporation of the two large targeting vectors was confirmed using the TAQMAN assays described above (Lie and Petropoulos, 1998. *Curr. Opin. Biotechnology* 9:43-48, incorporated herein by reference), using the probes and primers indicated in FIG. 1 and in Table 2.

As a comparison, the single LTVEC system described in Example 1 was also employed to modify the same genomic locus using a single LTVEC, either alone or in combination with a ZFN or CRISPR-Cas9 (see FIG. 2). Successful incorporation was confirmed by the TAQMAN assays described above, using primers and probes that are listed in Table 2 above and indicated in FIG. 2

Table 9 compares the targeting efficiencies in targeting experiments using the single LTVEC (alone, with ZFN, or with Cas9), using the two LTVECs simultaneously (alone, with ZFN, or with Cas9), or using the two LTVECs plus a third LTVEC simultaneously (alone, with ZFN, or with Cas9). The targeting efficiencies presented in Table 9 are the percentage of screened ESC clones that were determined to be correctly targeted through initial screening, confirmation screening, and reconfirmation screening using the TAQMAN primers and probes in Table 2. Targeting with a single LTVEC alone resulted in 1.1% correctly targeted clones. Cleavage with a ZFN increased the targeting efficiency of the single LTVEC to 4.4%, and cleavage with CRISPR-Cas9 increased the targeting efficiency of the single LTVEC to 5.5%. Surprisingly, targeting with 2 LTVECs having 20 kb in overlapping sequence resulted in a targeting efficiency of 1.4% even when no nuclease was used. The targeting efficiency increased to 2.81% when a ZFN was used and 1.6% when Cas9 was used.

TABLE 9

Targeting Efficiency of Co-Electroporated Tiled LTVECs

| | MAID 6598: | | | MAID 6600: 2nd & 3rd Insertions | | | MAID 6647: 2nd, 3rd, & 4th Insertions | | |
|---|---|---|---|---|---|---|---|---|---|
| | 2nd Insertion | | | 2 | 2 | | 3 | 3 | 3 |
| | LTVEC Alone | LTVEC + ZFN | LTVEC + Cas9 | LTVECs Alone | 2 LTVECs + ZFN | LTVECs + Cas9 | LTVECs Alone | LTVECS + ZFN | LTVECS + Cas9 |
| Targeting Efficiency | 5/440 (1.1%) | 17/384 (4.4%) | 21/384 (5.5%) | 13/960 (1.4%) | 27/960 (2.8%) | 15/960 (1.6%) | 0/960 (0%) | 4/960 (0.4%) | 4/960 (0.4%) |

We claim:

1. A method for modifying a target genomic locus on an endogenous chromosome in a mouse embryonic stem (ES) cell, comprising:
(a) introducing into the mouse ES cell a nuclease agent or a polynucleotide encoding the nuclease agent, wherein the nuclease agent is a zinc finger nuclease (ZFN), a Transcription Activator-Like Effector Nuclease (TALEN), or a Clustered Regularly Interspaced Short Palindromic Repeats (CRISPR)-associated (Cas) protein and a guide RNA (gRNA), and wherein the nuclease agent makes a single or double-strand break within the target genomic locus;
(b) introducing into the mouse ES cell a first large targeting vector (LTVEC) that comprises a first nucleic acid insert flanked by a first 5' homology arm and a first 3' homology arm, and a second LTVEC that comprises a second nucleic acid insert flanked by a second 5' homology arm and a second 3' homology arm,
wherein the sum total of the first 5' homology arm and the first 3' homology arm of the first LTVEC is from 10 kb to 150 kb, and the sum total of the second 5' homology arm and the second 3' homology arm of the second LTVEC is from 10 kb to 150 kb,
wherein the first 5' homology arm of the first LTVEC is at least 5 kb, and the second 3' homology arm of the second LTVEC is at least 5 kb,
wherein the combined size of the first nucleic acid insert and the second nucleic acid insert is from 100 kb to 500 kb,
wherein the first nucleic acid insert or the second nucleic acid insert comprises a nucleic acid encoding a selection marker,
wherein the first 3' homology arm of the first LTVEC has a first overlapping sequence with the second 5' homology arm of the second LTVEC, wherein the size of the first overlapping sequence is from 10 kb to 70 kb, and wherein the first 3' homology arm of the first LTVEC is identical to the second 5' homology arm of the second LTVEC, and
wherein the first 5' homology arm of the first LTVEC is homologous to a corresponding 5' target sequence within the target genomic locus, and the second 3' homology arm of the second LTVEC is homologous to a corresponding 3' target sequence within the target genomic locus,
wherein the method does not comprise introducing a separate expression construct comprising a selection marker not in conjunction with the first LTVEC or the second LTVEC, and
wherein the target genomic locus is modified by integration of the first nucleic acid insert and the second nucleic acid insert by homologous recombination between the first 5' homology arm of the first LTVEC and the 5' target sequence within the target genomic locus, between the first 3' homology arm of the first LTVEC and the second 5' homology arm of the second LTVEC, and between the second 3' homology arm of the second LTVEC and the 3' target sequence within the target genomic locus; and
(c) using the selection marker encoded by the nucleic acid in the first nucleic acid insert or the second nucleic acid insert to select a targeted mouse ES cell comprising the first nucleic acid insert and the second nucleic acid insert integrated into the target genomic locus, wherein the targeting efficiency is at least 1.6%.

2. The method of claim 1, wherein the first LTVEC and the second LTVEC comprise overlapping fragments of a contiguous nucleic acid, which is reformed by integration of the first nucleic acid insert and the second nucleic acid insert into the target genomic locus.

3. The method of claim 1, wherein the nuclease agent is the ZFN or the TALEN.

4. The method of claim 1, wherein the nuclease agent comprises the Cas protein and the gRNA.

5. The method of claim 4, wherein the Cas protein is Cas9.

6. The method of claim 1, wherein the first nucleic acid insert, the second nucleic acid insert, or both are from a species that is different from the species of the mouse ES cell.

7. The method of claim 6, wherein the first nucleic acid insert, the second nucleic acid insert, or both are human nucleic acids.

8. The method of claim 1, wherein the combined size of the first nucleic acid insert and the second nucleic acid insert is about 300 kb.

9. The method of claim 1, wherein integration of the first nucleic acid insert, the second nucleic acid insert, or both into the target genomic locus results in one or more of:
(a) an addition of an exogenous sequence at the target genomic locus;
(b) a deletion of an endogenous sequence at the target genomic locus; and
(c) a knock-in, a knockout, a point mutation, a domain swap, an exon swap, an intron swap, a regulatory sequence swap, a gene swap, or a combination thereof.

10. The method of claim 9, wherein integration of the first nucleic acid insert, the second nucleic acid insert, or both into the target genomic locus results in the deletion of the endogenous sequence at the target genomic locus, wherein the deletion is from about 5 kb to about 800 kb.

11. A method for producing an F0 generation mouse, comprising:
(a) introducing a mouse ES cell into a mouse host embryo, wherein the mouse ES cell was produced by the method of claim 1; and
(b) gestating the mouse host embryo in a mouse surrogate mother,
wherein the mouse surrogate mother produces the F0 generation mouse.

12. The method of claim 1, wherein the size of the first overlapping sequence is at least 20 kb.

13. The method of claim 1, wherein the combined size of the first nucleic acid insert and the second nucleic acid insert is at least 200 kb.

14. The method of claim 1, wherein the first LTVEC is at least 50 kb and the second LTVEC is at least 50 kb.

15. The method of claim 1, wherein the first LTVEC is at least 100 kb and the second LTVEC is at least 100 kb.

16. The method of claim 1, wherein the first LTVEC is a linear nucleic acid and/or the second LTVEC is a linear nucleic acid.

17. A method for modifying a target genomic locus on an endogenous chromosome in a mouse embryonic stem (ES) cell, comprising:
(a) introducing into the mouse ES cell a nuclease agent or a polynucleotide encoding the nuclease agent, wherein the nuclease agent is a zinc finger nuclease (ZFN), a Transcription Activator-Like Effector Nuclease (TALEN), or a Clustered Regularly Interspaced Short Palindromic Repeats (CRISPR)-associated (Cas) protein and a guide RNA (gRNA), and wherein the nuclease agent makes a single or double-strand break within the target genomic locus;
(b) introducing into the mouse ES cell a first large targeting vector (LTVEC) that comprises a first nucleic acid insert flanked by a first 5' homology arm and a first 3' homology arm, a second LTVEC that comprises a second nucleic acid insert flanked by a second 5' homology arm and a second 3' homology arm, and a third LTVEC that comprises a third nucleic acid insert flanked by a third 5' homology arm and a third 3' homology arm,
wherein the sum total of the first 5' homology arm and the first 3' homology arm of the first LTVEC is from 10 kb to 150 kb, the sum total of the second 5' homology arm and the second 3' homology arm of the second LTVEC is from 10 kb to 150 kb, and the sum total of the third 5' homology arm and the third 3' homology arm of the third LTVEC is from 10 kb to 150 kb,
wherein the first 5' homology arm of the first LTVEC is at least 5 kb, and the third 3' homology arm of the third LTVEC is at least 5 kb,
wherein the combined size of the first nucleic acid insert, the second nucleic acid insert, and the third nucleic acid insert from 100 kb to 700 kb,
wherein the first nucleic acid insert, the second nucleic acid insert, or the third nucleic acid insert comprises a nucleic acid encoding a selection marker,
wherein the first 3' homology arm of the first LTVEC has a first overlapping sequence with the second 5' homology arm of the second LTVEC, the second 3' homology arm of the second LTVEC has a second overlapping sequence with the third 5' homology arm of the third LTVEC, and the first 5' homology arm of the first LTVEC is homologous to a corresponding 5' target sequence within the target genomic locus, and the third 3' homology arm of the third LTVEC is homologous to a corresponding 3' target sequence within the target genomic locus,
wherein the first 3' homology arm of the first LTVEC is identical to the second 5' homology arm of the second LTVEC, and wherein the second 3' homology arm of the second LTVEC is identical to the third 5' homology arm of the third LTVEC, wherein the size of the first overlapping sequence is from 10 kb to 70 kb, and wherein the size of the second overlapping sequence is from 10 kb to 70 kb, wherein the method does not comprise introducing a separate expression construct comprising a selection marker not in conjunction with the first LTVEC, the second LTVEC, or the third LTVEC, and wherein the target genomic locus is modified by integration of the first nucleic acid insert, the second nucleic acid insert, and the third nucleic acid insert by homologous recombination between the first 5' homology arm of the first LTVEC and the 5' target sequence within the target genomic locus, between the first 3' homology arm of the first LTVEC and the second 5' homology arm of the second LTVEC, between the second 3' homology arm of the second LTVEC and the third 5' homology arm of the third LTVEC, and between the third 3' homology arm of the third LTVEC and the 3' target sequence within the target genomic locus; and (c) using the selection marker encoded by the nucleic acid in the first nucleic acid insert, the second nucleic acid insert, or the third nucleic acid insert to select a targeted mouse ES cell comprising the first nucleic acid insert, the second nucleic acid insert, and the third nucleic acid insert integrated into the target genomic locus, wherein the targeting efficiency is at least 0.4%.

18. A method for producing an F0 generation mouse, comprising:
(a) introducing a mouse ES cell into a mouse host embryo, wherein the mouse ES cell was produced by the method of claim 17; and
(b) gestating the mouse host embryo in a mouse surrogate mother,
wherein the mouse surrogate mother produces the F0 generation mouse.

19. The method of claim 17, wherein the first LTVEC, the second LTVEC, and the third LTVEC comprise overlapping fragments of a contiguous nucleic acid, which is reformed by integration of the first nucleic acid insert, the second nucleic acid insert, and the third nucleic acid insert into the target genomic locus.

20. The method of claim 17, wherein the nuclease agent is the ZFN or the TALEN.

21. The method of claim 17, wherein the nuclease agent comprises the Cas protein and the gRNA.

22. The method of claim 21, wherein the Cas protein is Cas9.

23. The method of claim 17, wherein one or more of the first nucleic acid insert, the second nucleic acid insert, and the third nucleic acid insert are from a species that is different from the species of the mouse ES cell.

24. The method of claim 23, wherein one or more of the first nucleic acid insert, the second nucleic acid insert, and the third nucleic acid insert are human nucleic acids.

25. The method of claim 17, wherein the combined size of the first nucleic acid insert, the second nucleic acid insert, and the third nucleic acid insert is about 400 kb.

26. The method of claim 17, wherein integration of one or more of the first nucleic acid insert, the second nucleic acid insert, and the third nucleic acid insert into the target genomic locus results in one or more of:
(a) an addition of an exogenous sequence at the target genomic locus;
(b) a deletion of an endogenous sequence at the target genomic locus; and
(c) a knock-in, a knockout, a point mutation, a domain swap, an exon swap, an intron swap, a regulatory sequence swap, a gene swap, or a combination thereof.

27. The method of claim 26, wherein integration of one or more of the first nucleic acid insert, the second nucleic acid insert, and the third nucleic acid insert into the target genomic locus results in the deletion of the endogenous sequence at the target genomic locus, wherein the deletion is from about 5 kb to about 800 kb.

28. The method of claim 17, wherein the size of the first overlapping sequence is at least 20 kb, and/or the size of the second overlapping sequence is at least 20 kb.

29. The method of claim 17, wherein the combined size of the first nucleic acid insert, the second nucleic acid insert, and the third nucleic acid insert is at least 200 kb.

30. The method of claim 17, wherein the first LTVEC is at least 50 kb, the second LTVEC is at least 50 kb, and the third LTVEC is at least 50 kb.

31. The method of claim 17, wherein the first LTVEC is at least 100 kb, the second LTVEC is at least 100 kb, and the third LTVEC is at least 100 kb.

32. The method of claim 17, wherein the first LTVEC is a linear nucleic acid, and/or the second LTVEC is a linear nucleic acid, and/or the third LTVEC is a linear nucleic acid.

* * * * *